US012071632B2

(12) United States Patent
Munir et al.

(10) Patent No.: US 12,071,632 B2
(45) Date of Patent: Aug. 27, 2024

(54) CHIMERIC VECTORS

(71) Applicant: The United States of America,as represented by the Secretary,Department of Health and Human Services, Bethesda, MD (US)

(72) Inventors: Shirin Munir, Potomac, MD (US); Linda G. Brock, Wyckoff, NJ (US); Ursula J. Buchholz, Silver Spring, MD (US); Peter L. Collins, Silver Spring, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 555 days.

(21) Appl. No.: 17/049,916

(22) PCT Filed: Apr. 23, 2019

(86) PCT No.: PCT/US2019/028771
§ 371 (c)(1),
(2) Date: Oct. 22, 2020

(87) PCT Pub. No.: WO2019/209859
PCT Pub. Date: Oct. 31, 2019

(65) Prior Publication Data

US 2021/0189425 A1 Jun. 24, 2021

Related U.S. Application Data

(60) Provisional application No. 62/661,320, filed on Apr. 23, 2019.

(51) Int. Cl.

| | |
|---|---|
| ***C12N 15/86*** | (2006.01) |
| ***A61K 39/155*** | (2006.01) |
| ***A61P 31/14*** | (2006.01) |
| *A61K 39/00* | (2006.01) |

(52) U.S. Cl.
CPC ............ *C12N 15/86* (2013.01); *A61K 39/155* (2013.01); *A61P 31/14* (2018.01); *A61K 2039/5256* (2013.01); *A61K 2039/543* (2013.01); *C12N 2760/18534* (2013.01); *C12N 2760/18544* (2013.01); *C12N 2760/18551* (2013.01)

(58) Field of Classification Search
None
See application file for complete search history.

(56) References Cited

U.S. PATENT DOCUMENTS

| | | | | |
|---|---|---|---|---|
| 9,193,780 B2 * | 11/2015 | Hultberg | ............ | C07K 16/1018 |
| 2005/0053919 A1 | 3/2005 | De Jong et al. | | |

FOREIGN PATENT DOCUMENTS

| | | | | |
|---|---|---|---|---|
| JP | 2008-518602 A | 6/2008 | | |
| WO | WO 2001/004335 A2 | 1/2001 | | |
| WO | WO-0104335 A2 * | 1/2001 | ............ | A61K 39/12 |
| WO | WO 2006/050280 A2 | 5/2006 | | |
| WO | WO 2016/118642 A1 | 7/2016 | | |

OTHER PUBLICATIONS

SEQ ID# 56 vs. 61 (Year: 2023).*
Brock et al., J of Virology, vol. 86, No. 10, pp. 5829-5843 (Year: 2012).*
Bennett et al., "Immunization strategies for the prevention of pneumovirus infections," *Expert Rev. Vaccines*, 6(2): 169-182 (2007).
Bernstein et al., "Phase 1 Study of the Safety and Immunogenicity of a Live, Attenuated Respiratory Syncytial Virus and Parainfluenza Virus Type 3 Vaccine in Seronegative Children," The Pediatric Infectious Disease Journal, 31(2): 109-114 (2012).
Brock et al., "Evaluation of Pneumonia Virus of Mice as a Possible Human Pathogen," *Journal of Virology*, 86(10): 5829-5843 (2012).
Brock et al., "Murine Pneumonia Virus Expressing the Fusion Glycoprotein of Human Respiratory Syncytial Virus from an Added Gene Is Highly Attenuated and Immunogenic in Rhesus Macaques," *Journal of Virology*, 92(17): e00723-18 (2018).
Chen, "Parainfluenza virus 5-vectored vaccines against human and animal infectious diseases," *Rev. Med. Virol.*, 28: e1965 (2018).
Collins et al., "Production of infectious human respiratory syncytial virus from cloned cDNA confirms an essential role for the transcription elongation factor from the 5' proximal open reading frame of the M2 mRNA in gene expression and provides a capability for vaccine development," *Proc. Natl. Acad. Sci. USA*, 92: 11563-11567 (1995).
European Patent Office, International Search Report in International Patent Application No. PCT/US2019/028771, mailed Apr. 23, 2018.
European Patent Office, Written Opinion in International Patent Application No. PCT/US2019/028771, mailed Apr. 23, 2018.
Frantz et al., "Measles-derived vaccines to prevent emerging viral diseases," *Microbes and Infection*, 20(9-10): 493-500 (2018).
Geisbert et al., "Recombinant Vesicular Stomatitis Virus-Based Vaccines Against Ebola and Marburg Virus Infections," *JID*, 204(Suppl. 3): S1075-S1081 (2011).
Haller et al., "Bovine parainfluenza virus type 3 (PIV3) expressing the respiratory syncytial virus (RSV) attachment and fusion proteins protects hamsters from challenge with human PIV3 and RSV," *Journal of General Virology*, 84: 2153-2162 (2003).
Joyce et al., "Iterative structure-based improvement of a fusion-glycoprotein vaccine against RSV," *Nature Structural & Molecular Biology*, 23(9): 811-820 (2016).

(Continued)

*Primary Examiner* — Shanon A. Foley
*Assistant Examiner* — Myron G Hill
(74) *Attorney, Agent, or Firm* — Leydig, Voit & Mayer, Ltd.

(57) ABSTRACT

Disclosed are live, chimeric non-human Mononegavirales vectors that allow a cell to express at least one protein from at least one human pathogen. In addition, compositions comprising the vectors, methods and kits for eliciting an immune response in a host, and methods of making the vectors are disclosed, in accordance with embodiments of the invention.

19 Claims, 7 Drawing Sheets

Figure 1:
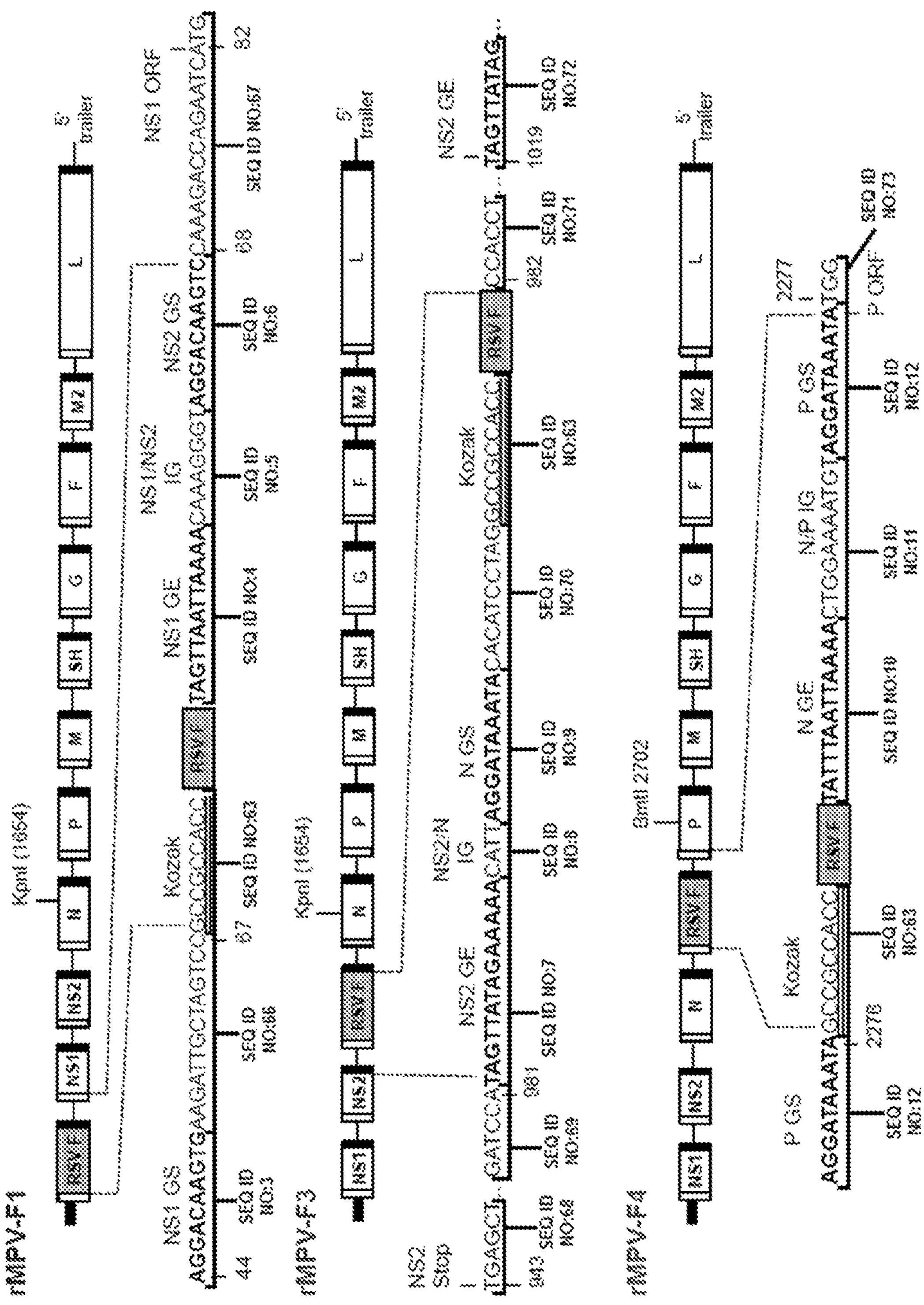

Specification includes a Sequence Listing.

(56) References Cited

OTHER PUBLICATIONS

Krempl et al., "Identification of a Novel Virulence Factor in Recombinant Pneumonia Virus of Mice," *Journal of Virology*, 81(17): 9490-9501 (2007).
Liang et al., "Chimeric Bovine/Human Parainfluenza Virus Type 3 Expressing Respiratory Syncytial Virus (RSV) F Glycoprotein: Effect of Insert Position on Expression, Replication, Immunogenicity, Stability, and Protection against RSV Infection," *Journal of Virology*, 88(8): 4237-4250 (2014).
Liang et al., "Enhanced Neutralizing Antibody Response Induced by Respiratory Syncytial Virus Prefusion F Protein Expressed by a Vaccine Candidate," *Journal of Virology*, 89(18): 9499-9510 (2015).
Llang et al., "Improved Prefusion Stability, Optimized Codon Usage, and Augmented Virion Packaging Enhance the Immunogenicity of Respiratory Syncytial Virus Fusion Protein in a Vectored-Vaccine Candidate," *Journal of Virology*, 91(15): e00189-17 (2017).
Mackow et al., "Attenuated Human Parainfluenza Virus Type 1 (HPIV1) Expressing the Fusion Glycoprotein of Human Respiratory Syncytial Virus (RSV) as a Bivalent HPIV1/RSV Vaccine," *Journal of Virology*, 89(20): 10319-10332 (2015).
McLellan et al., "Structure of RSV Fusion Glycoprotein Trimer Bound to a Prefusion-Specific Neutralizing Antibody," *Science*, 340: 1113-1117 (2013).
McLellan et al., "Structure-Based Design of a Fusion Glycoprotein Vaccine for Respiratory Syncytial Virus," *Science*, 342: 592-598 (2013).
Mok et al., "Evaluation of Measles Vaccine Virus as a Vector to Deliver Respiratory Syncytial Virus Fusion Protein or Epstein-Barr Virus Glycoprotein gp350," *The Open Virology Journal*, 6: 12-22 (2012).
Nakaya et al., "Recombinant Newcastle Disease Virus as a Vaccine Vector," *Journal of Virology*, 75(23): 11868-11873 (2001).
Ramezanpour et al., "Vector-based genetically modified vaccines: Exploiting Jenner's legacy," *Vaccine*, 34: 6436-6448 (2016).
Skiadopoulos et al., "Determinants of the Host Range Restriction of Replication of Bovine Parainfluenza Virus Type 3 in Rhesus Monkeys Are Polygenic," *Journal of Virology*, 77(2): 1141-1148 (2003).
Spann et al., "Genetic Recombination during Coinfection of Two Mutants of Human Respiratory Syncytial Virus," *Journal of Virology*, 77(20): 11201-11211 (2003).
Taylor et al., "Animal models of respiratory syncytial virus infection," *Vaccine*, 35: 469-480 (2017).
Yang et al., "Implication of respiratory syncytial virus (RSV) F transgene sequence heterogeneity observed in Phase 1 evaluation of MEDI-534, a live attenuated parainfluenza type 3 vectored RSV vaccine," *Vaccine*, 31: 2822-2827 (2013).
Buchholz et al., "Mucosal prime-boost immunization with live murine pneumonia virus-vectored SARS-CoV-2 vaccine is protective in macaques," *Research Square* preprint, rs.3.rs-3278289 (2023).
Kaiser et al., "Intranasal murine pneumonia virus-vectored SARS-CoV-2 vaccine induces mucosal and serum antibodies in macaques," *iScience*, 26: 108490 (2023), 17 pp.

* cited by examiner

```
                         SEQUENCE LISTING


<160> NUMBER OF SEQ ID NOS: 73

<210> SEQ ID NO 1
<211> LENGTH: 43
<212> TYPE: DNA
<213> ORGANISM: Pneumonia virus of mice

<400> SEQUENCE: 1

acgcgaaaaa atgcataaca aaactatcaa cctgaaaaaa gtt                          43


<210> SEQ ID NO 2
<211> LENGTH: 91
<212> TYPE: DNA
<213> ORGANISM: Pneumonia virus of mice

<400> SEQUENCE: 2

ttgatatctc acaggttgta aacatagttc ttttataatt attgttagtt aaactattgt      60

gtttgacttc ctttgggtat ttttttcccg t                                     91


<210> SEQ ID NO 3
<211> LENGTH: 10
<212> TYPE: DNA
<213> ORGANISM: Pneumonia virus of mice

<400> SEQUENCE: 3

aggacaagtg                                                             10


<210> SEQ ID NO 4
<211> LENGTH: 13
<212> TYPE: DNA
<213> ORGANISM: Pneumonia virus of mice

<400> SEQUENCE: 4

tagttaatta aaa                                                         13


<210> SEQ ID NO 5
<211> LENGTH: 8
<212> TYPE: DNA
<213> ORGANISM: Pneumonia virus of mice

<400> SEQUENCE: 5

caaagggt                                                                8
```

-continued

<210> SEQ ID NO 6
<211> LENGTH: 10
<212> TYPE: DNA
<213> ORGANISM: Pneumonia virus of mice

<400> SEQUENCE: 6
aggacaagtc 10

<210> SEQ ID NO 7
<211> LENGTH: 14
<212> TYPE: DNA
<213> ORGANISM: Pneumonia virus of mice

<400> SEQUENCE: 7
tagttataga aaaa 14

<210> SEQ ID NO 8
<211> LENGTH: 4
<212> TYPE: DNA
<213> ORGANISM: Pneumonia virus of mice

<400> SEQUENCE: 8 catt 4

<210> SEQ ID NO 9
<211> LENGTH: 10
<212> TYPE: DNA
<213> ORGANISM: Pneumonia virus of mice

<400> SEQUENCE: 9
aggataaata 10

<210> SEQ ID NO 10
<211> LENGTH: 13
<212> TYPE: DNA
<213> ORGANISM: Pneumonia virus of mice

<400> SEQUENCE: 10
tatttaatta aaa 13

<210> SEQ ID NO 11
<211> LENGTH: 11
<212> TYPE: DNA
<213> ORGANISM: Pneumonia virus of mice

<400> SEQUENCE: 11
ctggaaaatg t 11

<210> SEQ ID NO 12
<211> LENGTH: 10
<212> TYPE: DNA
<213> ORGANISM: Pneumonia virus of mice

<400> SEQUENCE: 12
aggataaata 10

<210> SEQ ID NO 13
<211> LENGTH: 13
<212> TYPE: DNA
<213> ORGANISM: Pneumonia virus of mice

<400> SEQUENCE: 13

-continued tagttaatta aaa 13

<210> SEQ ID NO 14
<211> LENGTH: 7
<212> TYPE: DNA
<213> ORGANISM: Pneumonia virus of mice

<400> SEQUENCE: 14 taacaac 7

<210> SEQ ID NO 15
<211> LENGTH: 10
<212> TYPE: DNA
<213> ORGANISM: Pneumonia virus of mice

<400> SEQUENCE: 15
aggacaaata 10

<210> SEQ ID NO 16
<211> LENGTH: 13
<212> TYPE: DNA
<213> ORGANISM: Pneumonia virus of mice

<400> SEQUENCE: 16
tagttaaata aaa 13

<210> SEQ ID NO 17
<211> LENGTH: 2
<212> TYPE: DNA
<213> ORGANISM: Pneumonia virus of mice

<400> SEQUENCE: 17 tc 2

<210> SEQ ID NO 18
<211> LENGTH: 10
<212> TYPE: DNA
<213> ORGANISM: Pneumonia virus of mice

<400> SEQUENCE: 18
aggataaata 10

<210> SEQ ID NO 19
<211> LENGTH: 14
<212> TYPE: DNA
<213> ORGANISM: Pneumonia virus of mice

<400> SEQUENCE: 19
tagttaacaa aaaa 14

<210> SEQ ID NO 20
<211> LENGTH: 5
<212> TYPE: DNA
<213> ORGANISM: Pneumonia virus of mice

<400> SEQUENCE: 20 ccggt 5

<210> SEQ ID NO 21
<211> LENGTH: 15
<212> TYPE: DNA
<213> ORGANISM: Pneumonia virus of mice

<400> SEQUENCE: 21
aggataagta ctatc 15

<210> SEQ ID NO 22
<211> LENGTH: 13
<212> TYPE: DNA
<213> ORGANISM: Pneumonia virus of mice

<400> SEQUENCE: 22
tagttaatga aaa 13

<210> SEQ ID NO 23
<211> LENGTH: 17
<212> TYPE: DNA
<213> ORGANISM: Pneumonia virus of mice

<400> SEQUENCE: 23
ctaagctttg atataat 17

<210> SEQ ID NO 24
<211> LENGTH: 10
<212> TYPE: DNA
<213> ORGANISM: Pneumonia virus of mice

<400> SEQUENCE: 24
aggacaaata 10

<210> SEQ ID NO 25
<211> LENGTH: 14
<212> TYPE: DNA
<213> ORGANISM: Pneumonia virus of mice

<400> SEQUENCE: 25
tagttaatta aaaa 14

<210> SEQ ID NO 26
<211> LENGTH: 3
<212> TYPE: DNA
<213> ORGANISM: Pneumonia virus of mice

<400> SEQUENCE: 26 ctt 3

<210> SEQ ID NO 27
<211> LENGTH: 11
<212> TYPE: DNA
<213> ORGANISM: Pneumonia virus of mice

<400> SEQUENCE: 27
aggataagtg a 11

<210> SEQ ID NO 28
<211> LENGTH: 16
<212> TYPE: DNA
<213> ORGANISM: Pneumonia virus of mice

<400> SEQUENCE: 28
tagttatata aaaaaa 16

<210> SEQ ID NO 29
<211> LENGTH: 10
<212> TYPE: DNA
<213> ORGANISM: Pneumonia virus of mice

<400> SEQUENCE: 29
tattcgaatt 10

<210> SEQ ID NO 30
<211> LENGTH: 10
<212> TYPE: DNA
<213> ORGANISM: Pneumonia virus of mice

<400> SEQUENCE: 30
aggatcaata 10

<210> SEQ ID NO 31
<211> LENGTH: 14
<212> TYPE: DNA
<213> ORGANISM: Pneumonia virus of mice

<400> SEQUENCE: 31
tagttaacaa aaaa 14

<210> SEQ ID NO 32
<211> LENGTH: 342
<212> TYPE: DNA
<213> ORGANISM: Pneumonia virus of mice

<400> SEQUENCE: 32
atgggctgta atgtgatgat ggagcttgat tatggtggac gagctgcatg gctggcattc 60
cacataacca actttgatag gtcagatttg gaaactatcc taagaggtgc tagggtgtgc 120
aatacatggc aagatcagag actctccgtg taccttgtgg gaagggattg caatttgtta 180
agaccatttg tgcaagctgc caaatttatc cataatacta ggagaggcca aacattaaca 240
cattggttca caaaaaatat cgtgtttagt tctacagggc aagagacaga gcctcccatt 300
gaccccacat gtgagctgtt ggtagagctg atcagtggtt aa 342

<210> SEQ ID NO 33
<211> LENGTH: 113
<212> TYPE: PRT
<213> ORGANISM: Pneumonia virus of mice

<400> SEQUENCE: 33

Met Gly Cys Asn Val Met Met Glu Leu Asp Tyr Gly Gly Arg Ala Ala
1 5 10 15

Trp Leu Ala Phe His Ile Thr Asn Phe Asp Arg Ser Asp Leu Glu Thr
20 25 30

Ile Leu Arg Gly Ala Arg Val Cys Asn Thr Trp Gln Asp Gln Arg Leu
35 40 45

Ser Val Tyr Leu Val Gly Arg Asp Cys Asn Leu Leu Arg Pro Phe Val
50 55 60

Gln Ala Ala Lys Phe Ile His Asn Thr Arg Arg Gly Gln Thr Leu Thr
65 70 75 80

His Trp Phe Thr Lys Asn Ile Val Phe Ser Ser Thr Gly Gln Glu Thr
85 90 95

Glu Pro Pro Ile Asp Pro Thr Cys Glu Leu Leu Val Glu Leu Ile Ser
100 105 110

Gly

<210> SEQ ID NO 34
<211> LENGTH: 471
<212> TYPE: DNA

<213> ORGANISM: Pneumonia virus of mice

<400> SEQUENCE: 34
atgtccacag ctatgaacaa gttcactcag accatctcta aacctgccac tatcttgaat 60
atttcagaca gtgaagagtc gggcgatgag gcaggggtgg gcaaggtgtc ccgtaccaca 120
cagagctcag agaggtggct tgatttgctc attgaaaagt tccagccgag cctacaaaac 180
atcactagat acatcaactg gaacttcatc aggatctgca atgataggct taaaaaagaa 240
aaaatggggt acattgaggc caagcaatat gtggaagaca tggcttggat ggtgatagca 300
tctgaggcag acagcattga gtggaagtgc ataaggaggc aggagaaagt gactggggtg 360
aaatacccaa agttcttctt tgtacaacac aaagaggact ggattgagtg cacaggatgc 420
attccgtacc caggccatga cttgatctat gatgaggatg atgatgactg a 471

<210> SEQ ID NO 35
<211> LENGTH: 156
<212> TYPE: PRT
<213> ORGANISM: Pneumonia virus of mice

<400> SEQUENCE: 35

Met Ser Thr Ala Met Asn Lys Phe Thr Gln Thr Ile Ser Lys Pro Ala
1 5 10 15

Thr Ile Leu Asn Ile Ser Asp Ser Glu Glu Ser Gly Asp Glu Ala Gly
20 25 30

Val Gly Lys Val Ser Arg Thr Thr Gln Ser Ser Glu Arg Trp Leu Asp
35 40 45

Leu Leu Ile Glu Lys Phe Gln Pro Ser Leu Gln Asn Ile Thr Arg Tyr
50 55 60

Ile Asn Trp Asn Phe Ile Arg Ile Cys Asn Asp Arg Leu Lys Lys Glu
65 70 75 80

Lys Met Gly Tyr Ile Glu Ala Lys Gln Tyr Val Glu Asp Met Ala Trp
85 90 95

Met Val Ile Ala Ser Glu Ala Asp Ser Ile Glu Trp Lys Cys Ile Arg
100 105 110

Arg Gln Glu Lys Val Thr Gly Val Lys Tyr Pro Lys Phe Phe Phe Val
115 120 125

Gln His Lys Glu Asp Trp Ile Glu Cys Thr Gly Cys Ile Pro Tyr Pro
130 135 140

Gly His Asp Leu Ile Tyr Asp Glu Asp Asp Asp Asp
145 150 155

<210> SEQ ID NO 36
<211> LENGTH: 1182
<212> TYPE: DNA
<213> ORGANISM: Pneumonia virus of mice

<400> SEQUENCE: 36
atgtctctag acagattgaa gctcaatgat gtctcaaaca aggatagcct gctgtccaac 60
tgcaaataca gtgttaccag atccacaggc gatgtaacca gtgtgtctgg tcatgctatg 120
cagaaagccc ttgcaaggac actcggcatg ttcttactta ctgccttcaa ccgttgcgaa 180
gaagtggcag aaatagggct ccaatatgcc atgtccttgc taggcagaga tgatagcatc 240
aagatattaa gagaagccgg ctacaatgta aaatgtgtgg acacacagct caaggacttt 300
acaatcaaat tacaaggaaa ggaatacaaa atacaagtcc tagatatagt gggaatagat 360
gcagccaatt tagctgatct agagatacaa gccagaggag tggtagcaaa agaactcaaa 420

-continued

```
acaggagcca ggctacctga caatcggagg catgatgcac cagattgtgg tgtgatagtt    480

ctctgtattg cagcattagt tgtttccaaa ttagctgcag gggacagggg aggacttgat    540

gctgtggaaa gaagggcttt aaatgtgctg aaagccgaga aagccaggta ccccaacatg    600

gaggtcaagc agatagctga aagtttttat gatctgtttg aaaggaagcc ttattacatt    660

gatgtcttca tcacttttgg cctggcccag tctagtgtca agggaggcag caaagttgag    720

gggctgtttt caggtctctt catgaatgca tacggggcag gacaagttat gctgaggtgg    780

ggtttactgg caaaatctgt caagaacatc atgctaggcc atgctagtgt acaagctgag    840

atggaacagg tggttgaggt ttacgaatat gctcagaagc aaggagggga ggcaggattc    900

tatcacatca gaaataatcc aaaagcttca cttctctctt tgaccaattg tcctaatttc    960

accagtgttg tgcttggcaa tgctgcaggt ttaggcatca tagggtcata taagggtgct   1020

cctaggaata gagaactctt tgatgctgcc aaagattatg cagaaagatt aaaggacaac   1080

aatgtaatta actacagtgc attaaacttg actgcagaag aaagagagct gatcagccag   1140

cagctgaaca ttgttgatga cactcctgat gatgatattt aa                      1182
```

```
<210> SEQ ID NO 37
<211> LENGTH: 393
<212> TYPE: PRT
<213> ORGANISM: Pneumonia virus of mice

<400> SEQUENCE: 37

Met Ser Leu Asp Arg Leu Lys Leu Asn Asp Val Ser Asn Lys Asp Ser
1               5                   10                  15

Leu Leu Ser Asn Cys Lys Tyr Ser Val Thr Arg Ser Thr Gly Asp Val
            20                  25                  30

Thr Ser Val Ser Gly His Ala Met Gln Lys Ala Leu Ala Arg Thr Leu
        35                  40                  45

Gly Met Phe Leu Leu Thr Ala Phe Asn Arg Cys Glu Glu Val Ala Glu
    50                  55                  60

Ile Gly Leu Gln Tyr Ala Met Ser Leu Leu Gly Arg Asp Asp Ser Ile
65                  70                  75                  80

Lys Ile Leu Arg Glu Ala Gly Tyr Asn Val Lys Cys Val Asp Thr Gln
                85                  90                  95

Leu Lys Asp Phe Thr Ile Lys Leu Gln Gly Lys Glu Tyr Lys Ile Gln
            100                 105                 110

Val Leu Asp Ile Val Gly Ile Asp Ala Ala Asn Leu Ala Asp Leu Glu
        115                 120                 125

Ile Gln Ala Arg Gly Val Val Ala Lys Glu Leu Lys Thr Gly Ala Arg
    130                 135                 140

Leu Pro Asp Asn Arg Arg His Asp Ala Pro Asp Cys Gly Val Ile Val
145                 150                 155                 160

Leu Cys Ile Ala Ala Leu Val Val Ser Lys Leu Ala Ala Gly Asp Arg
                165                 170                 175

Gly Gly Leu Asp Ala Val Glu Arg Arg Ala Leu Asn Val Leu Lys Ala
            180                 185                 190

Glu Lys Ala Arg Tyr Pro Asn Met Glu Val Lys Gln Ile Ala Glu Ser
        195                 200                 205

Phe Tyr Asp Leu Phe Glu Arg Lys Pro Tyr Tyr Ile Asp Val Phe Ile
    210                 215                 220

Thr Phe Gly Leu Ala Gln Ser Ser Val Lys Gly Gly Ser Lys Val Glu
225                 230                 235                 240
```

-continued

```
Gly Leu Phe Ser Gly Leu Phe Met Asn Ala Tyr Gly Ala Gly Gln Val
                245                 250                 255

Met Leu Arg Trp Gly Leu Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Gln Gly Gly Glu Ala Gly Phe Tyr His Ile Arg
    290                 295                 300

Asn Asn Pro Lys Ala Ser Leu Leu Ser Leu Thr Asn Cys Pro Asn Phe
305                 310                 315                 320

Thr Ser Val Val Leu Gly Asn Ala Ala Gly Leu Gly Ile Ile Gly Ser
                325                 330                 335

Tyr Lys Gly Ala Pro Arg Asn Arg Glu Leu Phe Asp Ala Ala Lys Asp
            340                 345                 350

Tyr Ala Glu Arg Leu Lys Asp Asn Asn Val Ile Asn Tyr Ser Ala Leu
        355                 360                 365

Asn Leu Thr Ala Glu Glu Arg Glu Leu Ile Ser Gln Gln Leu Asn Ile
    370                 375                 380

Val Asp Asp Thr Pro Asp Asp Asp Ile
385                 390

<210> SEQ ID NO 38
<211> LENGTH: 888
<212> TYPE: DNA
<213> ORGANISM: Pneumonia virus of mice

<400> SEQUENCE: 38

atggagaaat tcgcccccga atttgttggc gaggatgcta acaagaaggc agaggagttt     60

ctcaaacata gatccttccc ttcggaaaaa ccactagctg gtataccgaa cactgccact    120

catgtcacca aatataacat gccccctata ttgcgtagct cattcaaact cccttccccg    180

agagttgctg caaatcttac tgaaccctct gctcccccta ccactccacc acccacacct    240

ccccagaaca aggaagagca gcccaaagag tctgatgttg acattgagac tatgcatgtc    300

tgtaaggttc ctgacaatcc ggaacacagc aagaagccat gctgctcaga tgataccgat    360

actaagaaaa ctaggaagcc gatggtcacc tttgtggaac ccgaggagaa atttgtcgga    420

ttgggagcta gcttgtacag ggagaccatg cagacctttg ctgctgatgg ttatgatgaa    480

gaaagcaacc tatcgtttga ggagactaac caagagccgg gttcttcatc tgtagaacaa    540

agactagata gaatagagga gaaattgtcc tacataatag gcctttttaa caccataatg    600

gtagcgactg ctggacctac cactgctaga gatgagatta gagatgccct tataggcact    660

agagaagaac ttattgagat gatcaagtct gacatcttga ctgtcaatga cagaatagtg    720

gccatggaga agctcagaga tgaggaatgc tccagagctg acactgatga tggatcagcc    780

tgttatttaa cagacagagc aaggatacta gataagatag tgtccagcaa tgctgaagag    840

gctaaggaag atttggatgt tgatgacatc atgggcatta atttttag                 888

<210> SEQ ID NO 39
<211> LENGTH: 295
<212> TYPE: PRT
<213> ORGANISM: Pneumonia virus of mice

<400> SEQUENCE: 39

Met Glu Lys Phe Ala Pro Glu Phe Val Gly Glu Asp Ala Asn Lys Lys
1               5                   10                  15
```

-continued

```
Ala Glu Glu Phe Leu Lys His Arg Ser Phe Pro Ser Glu Lys Pro Leu
            20                  25                  30

Ala Gly Ile Pro Asn Thr Ala Thr His Val Thr Lys Tyr Asn Met Pro
        35                  40                  45

Pro Ile Leu Arg Ser Ser Phe Lys Leu Pro Ser Pro Arg Val Ala Ala
    50                  55                  60

Asn Leu Thr Glu Pro Ser Ala Pro Pro Thr Thr Pro Pro Pro Thr Pro
65                  70                  75                  80

Pro Gln Asn Lys Glu Glu Gln Pro Lys Glu Ser Asp Val Asp Ile Glu
                85                  90                  95

Thr Met His Val Cys Lys Val Pro Asp Asn Pro Glu His Ser Lys Lys
            100                 105                 110

Pro Cys Cys Ser Asp Asp Thr Asp Thr Lys Lys Thr Arg Lys Pro Met
        115                 120                 125

Val Thr Phe Val Glu Pro Glu Glu Lys Phe Val Gly Leu Gly Ala Ser
    130                 135                 140

Leu Tyr Arg Glu Thr Met Gln Thr Phe Ala Ala Asp Gly Tyr Asp Glu
145                 150                 155                 160

Glu Ser Asn Leu Ser Phe Glu Glu Thr Asn Gln Glu Pro Gly Ser Ser
                165                 170                 175

Ser Val Glu Gln Arg Leu Asp Arg Ile Glu Glu Lys Leu Ser Tyr Ile
            180                 185                 190

Ile Gly Leu Leu Asn Thr Ile Met Val Ala Thr Ala Gly Pro Thr Thr
        195                 200                 205

Ala Arg Asp Glu Ile Arg Asp Ala Leu Ile Gly Thr Arg Glu Glu Leu
    210                 215                 220

Ile Glu Met Ile Lys Ser Asp Ile Leu Thr Val Asn Asp Arg Ile Val
225                 230                 235                 240

Ala Met Glu Lys Leu Arg Asp Glu Glu Cys Ser Arg Ala Asp Thr Asp
                245                 250                 255

Asp Gly Ser Ala Cys Tyr Leu Thr Asp Arg Ala Arg Ile Leu Asp Lys
            260                 265                 270

Ile Val Ser Ser Asn Ala Glu Glu Ala Lys Glu Asp Leu Asp Val Asp
        275                 280                 285

Asp Ile Met Gly Ile Asn Phe
    290                 295
```

<210> SEQ ID NO 40
<211> LENGTH: 774
<212> TYPE: DNA
<213> ORGANISM: Pneumonia virus of mice

<400> SEQUENCE: 40

```
atggaggcct acttggtaga gatgtaccat ggtgtcccat atacagctgc agtacagcta     60

aacttggttg aaaaacattc agccaacata tcactaactg tgtggatacc gatgtttcaa    120

acatctctac caaagaactc cgttatggac ctgctacatg atgttacagt catttgtaca    180

cagatatcaa cagtgcatgg tcccatgatc aaggtagatc tgagctcttc caatgcaggt    240

ttagctacca tgccaaggca attcttgata aatgctatca tagctttgga tgactggggc    300

aacatggatt acgaagtgcc tgttgctttt gataaaaaga gcttctgtgt gacaattctt    360

aagcctaaaa acatgcttta cactgtaccc agcattactc ccactaatcg acctactcat    420

gagctgatag ctgtctgctc tttccataac agggtaacat taaagtcatt caatatacct    480
```

-continued

```
gtcttcatca gagcactgtc tatcagacag caggaccttg atagtgtgga gcaggctata    540

agctccgatg tggaccatgc tataacaaca gctagggtgg ctccctatgc agggcttaca    600

cttgtgatca acatcacatc caccaaagga gcattcaaac tgctaaaggc aggtagtcag    660

attcttgcag aactgggtcc ctatctgacg caggtgagcc tacatgatgt gattatgaac    720

tggaaacata caggcacttc ctacatactc aagagctcct caacaagtgg atga          774


<210> SEQ ID NO 41
<211> LENGTH: 257
<212> TYPE: PRT
<213> ORGANISM: Pneumonia virus of mice

<400> SEQUENCE: 41

Met Glu Ala Tyr Leu Val Glu Met Tyr His Gly Val Pro Tyr Thr Ala
1               5                   10                  15

Ala Val Gln Leu Asn Leu Val Glu Lys His Ser Ala Asn Ile Ser Leu
            20                  25                  30

Thr Val Trp Ile Pro Met Phe Gln Thr Ser Leu Pro Lys Asn Ser Val
        35                  40                  45

Met Asp Leu Leu His Asp Val Thr Val Ile Cys Thr Gln Ile Ser Thr
    50                  55                  60

Val His Gly Pro Met Ile Lys Val Asp Leu Ser Ser Ser Asn Ala Gly
65                  70                  75                  80

Leu Ala Thr Met Pro Arg Gln Phe Leu Ile Asn Ala Ile Ile Ala Leu
                85                  90                  95

Asp Asp Trp Gly Asn Met Asp Tyr Glu Val Pro Val Ala Phe Asp Lys
            100                 105                 110

Lys Ser Phe Cys Val Thr Ile Leu Lys Pro Lys Asn Met Leu Tyr Thr
        115                 120                 125

Val Pro Ser Ile Thr Pro Thr Asn Arg Pro Thr His Glu Leu Ile Ala
    130                 135                 140

Val Cys Ser Phe His Asn Arg Val Thr Leu Lys Ser Phe Asn Ile Pro
145                 150                 155                 160

Val Phe Ile Arg Ala Leu Ser Ile Arg Gln Gln Asp Leu Asp Ser Val
                165                 170                 175

Glu Gln Ala Ile Ser Ser Asp Val Asp His Ala Ile Thr Thr Ala Arg
            180                 185                 190

Val Ala Pro Tyr Ala Gly Leu Thr Leu Val Ile Asn Ile Thr Ser Thr
        195                 200                 205

Lys Gly Ala Phe Lys Leu Leu Lys Ala Gly Ser Gln Ile Leu Ala Glu
    210                 215                 220

Leu Gly Pro Tyr Leu Thr Gln Val Ser Leu His Asp Val Ile Met Asn
225                 230                 235                 240

Trp Lys His Thr Gly Thr Ser Tyr Ile Leu Lys Ser Ser Ser Thr Ser
                245                 250                 255

Gly


<210> SEQ ID NO 42
<211> LENGTH: 279
<212> TYPE: DNA
<213> ORGANISM: Pneumonia virus of mice

<400> SEQUENCE: 42

atggatccta acatgacctc acaccagatc accctcgaga tcaacatgac cagcagccgt     60

attggcacat acactacacc agccccaaca gctcttctcc ttgcatgtgc cgtcatcaac    120
```

-continued

```
acagtgtgtg cgctgataat ggcctgcagc agtagaagca ctgccacatc aggcattgtc    180

agcagccaat gcacagttca tcccaatcac cctccaccaa gttatggcgt caatgtaact    240

ggtctgccgg gtaacctata ctcaaggaac actacataa                           279


<210> SEQ ID NO 43
<211> LENGTH: 92
<212> TYPE: PRT
<213> ORGANISM: Pneumonia virus of mice

<400> SEQUENCE: 43

Met Asp Pro Asn Met Thr Ser His Gln Ile Thr Leu Glu Ile Asn Met
1               5                   10                  15

Thr Ser Ser Arg Ile Gly Thr Tyr Thr Thr Pro Ala Pro Thr Ala Leu
            20                  25                  30

Leu Leu Ala Cys Ala Val Ile Asn Thr Val Cys Ala Leu Ile Met Ala
        35                  40                  45

Cys Ser Ser Arg Ser Thr Ala Thr Ser Gly Ile Val Ser Ser Gln Cys
    50                  55                  60

Thr Val His Pro Asn His Pro Pro Pro Ser Tyr Gly Val Asn Val Thr
65                  70                  75                  80

Gly Leu Pro Gly Asn Leu Tyr Ser Arg Asn Thr Thr
                85                  90


<210> SEQ ID NO 44
<211> LENGTH: 1191
<212> TYPE: DNA
<213> ORGANISM: Pneumonia virus of mice

<400> SEQUENCE: 44

atgggaagga acttagaagt gagtggcagc attaccaatt tgaactttga gagaactcag     60

catcctgaca catttaggac tgttgtaaaa gtgaaccaaa tgtgtaagct tattgcaggt    120

gtgctcacaa gtgctgctgt ggcagtttgt gtgggggtca taatgtattc tgttttcaca    180

tcaaaccaca aggccaactc cacgcagaat gccacgaccc ggaacagcac atccacccct    240

ccccaaccaa ccgccggtct gcccaccaca gagcaaggga ccatccccag attcaccaaa    300

ccccccacca aaaccgccac ccaccatgag atcacagagc ccgtcaaaat ggcaacacct    360

tcagaggatc cctaccaatg ctccagcaat ggttatttgg accgacctga tttacctgaa    420

aatttcaaac tcgtattgga tgttatatgc aagcctccag gtcctgaaca tcacaacacc    480

agctgttatg agaaacgtga aatcaaccca ggaagtgttt gccctgatct tgtaacaatg    540

aaggcaaaca tgggcttaaa caatggtggt ggggaggatg ctgcacctta tatagaggtt    600

accacccttt ctacgtactc caacaaaagg gcaatgtgtg tccacaatgg gtgtgatcaa    660

ggcttctgtt tcttcctttc tggtttaagc actgatcagg agagagctgt gctagagctt    720

ggaggtcaac aggctatcat ggagttgcat tatgattcct actggaaaca ctattggagt    780

aactctaatt gtgttgttcc cagaacaaac tgcaacctga cagaccaaac tgagattttg    840

tttcctaggt ttaacaacaa gaatcagtct cagtgtacca cctgtgcaga ttcagctggc    900

ctagataaca aattttatct cacatgtgat gggcttttaa gaaccctccc tctagttgga    960

ctacccagcc taagtcctca ggcttacaaa gctgtaccca cacaaactac aggcaccacc   1020

acggcaccaa catcagagac gaggcaccca acccctgcac ccaggaggtc caaacctctc   1080

agtcggaaga agagagcttt atgtggtgta gactcaagca gagaacccaa accaacaatg   1140
```

-continued ccttactggt gtcctatgct ccaattattt ccaaggaggt ctaattctta a 1191

<210> SEQ ID NO 45
<211> LENGTH: 396
<212> TYPE: PRT
<213> ORGANISM: Pneumonia virus of mice

<400> SEQUENCE: 45

Met Gly Arg Asn Leu Glu Val Ser Gly Ser Ile Thr Asn Leu Asn Phe
1 5 10 15

Glu Arg Thr Gln His Pro Asp Thr Phe Arg Thr Val Val Lys Val Asn
20 25 30

Gln Met Cys Lys Leu Ile Ala Gly Val Leu Thr Ser Ala Ala Val Ala
35 40 45

Val Cys Val Gly Val Ile Met Tyr Ser Val Phe Thr Ser Asn His Lys
50 55 60

Ala Asn Ser Thr Gln Asn Ala Thr Thr Arg Asn Ser Thr Ser Thr Pro
65 70 75 80

Pro Gln Pro Thr Ala Gly Leu Pro Thr Thr Glu Gln Gly Thr Ile Pro
85 90 95

Arg Phe Thr Lys Pro Pro Thr Lys Thr Ala Thr His His Glu Ile Thr
100 105 110

Glu Pro Val Lys Met Ala Thr Pro Ser Glu Asp Pro Tyr Gln Cys Ser
115 120 125

Ser Asn Gly Tyr Leu Asp Arg Pro Asp Leu Pro Glu Asn Phe Lys Leu
130 135 140

Val Leu Asp Val Ile Cys Lys Pro Pro Gly Pro Glu His His Asn Thr
145 150 155 160

Ser Cys Tyr Glu Lys Arg Glu Ile Asn Pro Gly Ser Val Cys Pro Asp
165 170 175

Leu Val Thr Met Lys Ala Asn Met Gly Leu Asn Asn Gly Gly Gly Glu
180 185 190

Asp Ala Ala Pro Tyr Ile Glu Val Thr Thr Leu Ser Thr Tyr Ser Asn
195 200 205

Lys Arg Ala Met Cys Val His Asn Gly Cys Asp Gln Gly Phe Cys Phe
210 215 220

Phe Leu Ser Gly Leu Ser Thr Asp Gln Glu Arg Ala Val Leu Glu Leu
225 230 235 240

Gly Gly Gln Gln Ala Ile Met Glu Leu His Tyr Asp Ser Tyr Trp Lys
245 250 255

His Tyr Trp Ser Asn Ser Asn Cys Val Val Pro Arg Thr Asn Cys Asn
260 265 270

Leu Thr Asp Gln Thr Glu Ile Leu Phe Pro Arg Phe Asn Asn Lys Asn
275 280 285

Gln Ser Gln Cys Thr Thr Cys Ala Asp Ser Ala Gly Leu Asp Asn Lys
290 295 300

Phe Tyr Leu Thr Cys Asp Gly Leu Leu Arg Thr Leu Pro Leu Val Gly
305 310 315 320

Leu Pro Ser Leu Ser Pro Gln Ala Tyr Lys Ala Val Pro Thr Gln Thr
325 330 335

Thr Gly Thr Thr Thr Ala Pro Thr Ser Glu Thr Arg His Pro Thr Pro
340 345 350

Ala Pro Arg Arg Ser Lys Pro Leu Ser Arg Lys Lys Arg Ala Leu Cys
355 360 365

-continued

```
Gly Val Asp Ser Ser Arg Glu Pro Lys Pro Thr Met Pro Tyr Trp Cys
    370                 375                 380

Pro Met Leu Gln Leu Phe Pro Arg Arg Ser Asn Ser
385                 390                 395
```

<210> SEQ ID NO 46
<211> LENGTH: 1614
<212> TYPE: DNA
<213> ORGANISM: Pneumonia virus of mice

<400> SEQUENCE: 46

```
atgattcctg gcaggatctt tctagtcctt ctggtgatct tcaacaccaa gccaattcac      60

ccaaatacat taacagaaaa attctatgag tccacatgta gtgttgagac tgcaggttat     120

aagagtgccc ttagaacagg ttggcatatg acagttatgt caattaagtt gtctcaaata     180

aatattgagt catgcaagag cagcaactcg ttattggctc atgagcttgc aatctatagt     240

agtgcagtgg atgaattgag aacgttatca tccaatgcct tgaagtccaa aaggaagaag     300

aggttcctcg gtttgattct tggtctcgga gctgcagtca ctgccggggt ggctttagcc     360

aagacagtgc aacttgaaag tgagattgca ttgattagag atgcagtgag aaatacaaat     420

gaggctgttg ttagcctaac caacggcatg tcagtgttgg ctaaagtggt ggatgatttg     480

aaaaacttca tatctaaaga attactccca aaaataaacc gagtctcttg tgatgtgcac     540

gacatcactg ccgtcattag attccaacag ctcaacaaaa gacttttgga agtatctcgt     600

gaattttcat ctaatgcagg attaacacac actgtttcat cttttatgtt aacagaccgg     660

gaactcacct ccattgtagg cggcatggct gtttcagcag gccaaaaaga gataatgcta     720

tctagcaaag ctataatgag aagaaatggg ttagcaatat taagttcagt caacgctgac     780

acactggttt atgtaataca actcccatta tttggtgtta tggacacaga ttgttgggta     840

ataagaagtt ctatagactg tcataacata gcagacaagt atgcttgttt ggctagagct     900

gataatggct ggtattgtca caatgctggc tcattatcat acttcccgtc gccaacggat     960

tgtgagatcc acaatgggta tgctttctgt gacactctaa aagtctaac  tgtacctgta    1020

acatcacgag aatgcaactc aaacatgtat accactaact acgattgtaa gatttccaca    1080

agtaaaactt atgtgagtac agcggtactg actacaatgg gttgcttggt atcttgttat    1140

ggtcataaca gttgcacagt catcaataat gacaaaggta taataaggac tctgccagat    1200

ggttgccact acatctccaa caaaggtgtg gacagggttc aagtaggtaa cactgtttac    1260

tatcttagca aagaagttgg caagtcaatt gttgtcagag gggaaccatt ggtcttgaaa    1320

tatgaccctt tgagtttccc tgacgataaa tttgatgttg ctataagaga tgtggagcat    1380

agcatcaatc agacacgcac attcttgaag gcctctgatc agttattgga cttaagtgaa    1440

aacagagaga ataaaaattt aaacaagtca tatatactaa caactctgct cttcgttgta    1500

atgcttatta taataatggc tgtcataggg ttcattctgt ataaggtatt gaaaatgatc    1560

agagacaaca agttgaaatc caaaagtaca cctggcctca cagttttatc atga          1614
```

<210> SEQ ID NO 47
<211> LENGTH: 537
<212> TYPE: PRT
<213> ORGANISM: Pneumonia virus of mice

<400> SEQUENCE: 47

```
Met Ile Pro Gly Arg Ile Phe Leu Val Leu Leu Val Ile Phe Asn Thr
1               5                   10                  15
```

-continued

```
Lys Pro Ile His Pro Asn Thr Leu Thr Glu Lys Phe Tyr Glu Ser Thr
            20                  25                  30

Cys Ser Val Glu Thr Ala Gly Tyr Lys Ser Ala Leu Arg Thr Gly Trp
        35                  40                  45

His Met Thr Val Met Ser Ile Lys Leu Ser Gln Ile Asn Ile Glu Ser
    50                  55                  60

Cys Lys Ser Ser Asn Ser Leu Leu Ala His Glu Leu Ala Ile Tyr Ser
65                  70                  75                  80

Ser Ala Val Asp Glu Leu Arg Thr Leu Ser Ser Asn Ala Leu Lys Ser
                85                  90                  95

Lys Arg Lys Lys Arg Phe Leu Gly Leu Ile Leu Gly Leu Gly Ala Ala
            100                 105                 110

Val Thr Ala Gly Val Ala Leu Ala Lys Thr Val Gln Leu Glu Ser Glu
        115                 120                 125

Ile Ala Leu Ile Arg Asp Ala Val Arg Asn Thr Asn Glu Ala Val Val
    130                 135                 140

Ser Leu Thr Asn Gly Met Ser Val Leu Ala Lys Val Val Asp Asp Leu
145                 150                 155                 160

Lys Asn Phe Ile Ser Lys Glu Leu Leu Pro Lys Ile Asn Arg Val Ser
                165                 170                 175

Cys Asp Val His Asp Ile Thr Ala Val Ile Arg Phe Gln Gln Leu Asn
            180                 185                 190

Lys Arg Leu Leu Glu Val Ser Arg Glu Phe Ser Ser Asn Ala Gly Leu
        195                 200                 205

Thr His Thr Val Ser Ser Phe Met Leu Thr Asp Arg Glu Leu Thr Ser
    210                 215                 220

Ile Val Gly Gly Met Ala Val Ser Ala Gly Gln Lys Glu Ile Met Leu
225                 230                 235                 240

Ser Ser Lys Ala Ile Met Arg Arg Asn Gly Leu Ala Ile Leu Ser Ser
                245                 250                 255

Val Asn Ala Asp Thr Leu Val Tyr Val Ile Gln Leu Pro Leu Phe Gly
            260                 265                 270

Val Met Asp Thr Asp Cys Trp Val Ile Arg Ser Ser Ile Asp Cys His
        275                 280                 285

Asn Ile Ala Asp Lys Tyr Ala Cys Leu Ala Arg Ala Asp Asn Gly Trp
    290                 295                 300

Tyr Cys His Asn Ala Gly Ser Leu Ser Tyr Phe Pro Ser Pro Thr Asp
305                 310                 315                 320

Cys Glu Ile His Asn Gly Tyr Ala Phe Cys Asp Thr Leu Lys Ser Leu
                325                 330                 335

Thr Val Pro Val Thr Ser Arg Glu Cys Asn Ser Asn Met Tyr Thr Thr
            340                 345                 350

Asn Tyr Asp Cys Lys Ile Ser Thr Ser Lys Thr Tyr Val Ser Thr Ala
        355                 360                 365

Val Leu Thr Thr Met Gly Cys Leu Val Ser Cys Tyr Gly His Asn Ser
    370                 375                 380

Cys Thr Val Ile Asn Asn Asp Lys Gly Ile Ile Arg Thr Leu Pro Asp
385                 390                 395                 400

Gly Cys His Tyr Ile Ser Asn Lys Gly Val Asp Arg Val Gln Val Gly
                405                 410                 415

Asn Thr Val Tyr Tyr Leu Ser Lys Glu Val Gly Lys Ser Ile Val Val
            420                 425                 430

Arg Gly Glu Pro Leu Val Leu Lys Tyr Asp Pro Leu Ser Phe Pro Asp
```

```
        435                 440                 445

Asp Lys Phe Asp Val Ala Ile Arg Asp Val Glu His Ser Ile Asn Gln
    450                 455                 460

Thr Arg Thr Phe Leu Lys Ala Ser Asp Gln Leu Leu Asp Leu Ser Glu
465                 470                 475                 480

Asn Arg Glu Asn Lys Asn Leu Asn Lys Ser Tyr Ile Leu Thr Thr Leu
                485                 490                 495

Leu Phe Val Val Met Leu Ile Ile Ile Met Ala Val Ile Gly Phe Ile
            500                 505                 510

Leu Tyr Lys Val Leu Lys Met Ile Arg Asp Asn Lys Leu Lys Ser Lys
        515                 520                 525

Ser Thr Pro Gly Leu Thr Val Leu Ser
    530                 535


<210> SEQ ID NO 48
<211> LENGTH: 531
<212> TYPE: DNA
<213> ORGANISM: Pneumonia virus of mice

<400> SEQUENCE: 48

atgagtgtga gaccttgcaa atttgaggtt caagggtttt gttccagagg gaggaattgc      60

aagtatagtc ataaatattg ggaatggcct ttgaaaactc ttatgctcag gcagaactac     120

atgcttaata ggatttatag gttcctcgac accaacacag atgcaatgtc agatgtcagc     180

ggatttgatg caccacaaag gactgctgag tatgccttgg gaaccatagg tgtgctgaaa     240

agttacctgg aaaaaactaa caacatcact aaatcaatag cttgtggcag tttgatcact     300

gtattgcaga acttggatgt tggtctagta atacaagcaa gagatagcaa cactgaggac     360

accaattact tgagaagttg caacactata ctgtcttata tagacaagat acacaagaag     420

agacaaatta ttcacattct caaaagactg ccagtaggag tactatgcaa tctgatccaa     480

tctgtcatct ccatcgagga gaagataaat tcttctatga aaacagaatg a              531


<210> SEQ ID NO 49
<211> LENGTH: 176
<212> TYPE: PRT
<213> ORGANISM: Pneumonia virus of mice

<400> SEQUENCE: 49

Met Ser Val Arg Pro Cys Lys Phe Glu Val Gln Gly Phe Cys Ser Arg
1               5                   10                  15

Gly Arg Asn Cys Lys Tyr Ser His Lys Tyr Trp Glu Trp Pro Leu Lys
            20                  25                  30

Thr Leu Met Leu Arg Gln Asn Tyr Met Leu Asn Arg Ile Tyr Arg Phe
        35                  40                  45

Leu Asp Thr Asn Thr Asp Ala Met Ser Asp Val Ser Gly Phe Asp Ala
    50                  55                  60

Pro Gln Arg Thr Ala Glu Tyr Ala Leu Gly Thr Ile Gly Val Leu Lys
65                  70                  75                  80

Ser Tyr Leu Glu Lys Thr Asn Asn Ile Thr Lys Ser Ile Ala Cys Gly
                85                  90                  95

Ser Leu Ile Thr Val Leu Gln Asn Leu Asp Val Gly Leu Val Ile Gln
            100                 105                 110

Ala Arg Asp Ser Asn Thr Glu Asp Thr Asn Tyr Leu Arg Ser Cys Asn
        115                 120                 125

Thr Ile Leu Ser Tyr Ile Asp Lys Ile His Lys Lys Arg Gln Ile Ile
```

130 135 140

His Ile Leu Lys Arg Leu Pro Val Gly Val Leu Cys Asn Leu Ile Gln
145 150 155 160

Ser Val Ile Ser Ile Glu Glu Lys Ile Asn Ser Ser Met Lys Thr Glu
165 170 175

<210> SEQ ID NO 50
<211> LENGTH: 297
<212> TYPE: DNA
<213> ORGANISM: Pneumonia virus of mice

<400> SEQUENCE: 50
atgcaatctg atccaatctg tcatctccat cgaggagaag ataaattctt ctatgaaaac 60
agaatgataa ggctgcctaa atactatcca gccatactgc ataagatgta tattattaga 120
gtaaatagaa acctcactta cgatgggtct ggaccatcca caataataga tgcaggaaag 180
tctgtggtgt ggaatcgtgt tgatgtgata gcttgtgtga aagaggcctt gtgctgcata 240
gaattcagct ggaataacca agtgatcata gactttgatt atagccaggc cagatga 297

<210> SEQ ID NO 51
<211> LENGTH: 98
<212> TYPE: PRT
<213> ORGANISM: Pneumonia virus of mice

<400> SEQUENCE: 51

Met Gln Ser Asp Pro Ile Cys His Leu His Arg Gly Glu Asp Lys Phe
1 5 10 15

Phe Tyr Glu Asn Arg Met Ile Arg Leu Pro Lys Tyr Tyr Pro Ala Ile
20 25 30

Leu His Lys Met Tyr Ile Ile Arg Val Asn Arg Asn Leu Thr Tyr Asp
35 40 45

Gly Ser Gly Pro Ser Thr Ile Ile Asp Ala Gly Lys Ser Val Val Trp
50 55 60

Asn Arg Val Asp Val Ile Ala Cys Val Lys Glu Ala Leu Cys Cys Ile
65 70 75 80

Glu Phe Ser Trp Asn Asn Gln Val Ile Ile Asp Phe Asp Tyr Ser Gln
85 90 95

Ala Arg

<210> SEQ ID NO 52
<211> LENGTH: 6123
<212> TYPE: DNA
<213> ORGANISM: Pneumonia virus of mice

<400> SEQUENCE: 52
atggatccta ttgatgaaca agaagttaat gtgtacttgc cggatagcta cttaaagggt 60
gttatatctt ttagtgaaac taatgctctt ggcagctgta tcattggtag acctttcttg 120
aaggatgact ttactgccac tacttcaatc cgtaaccccc taattgaaca taaaagaata 180
agggacacta aattagtaaa aaatattgtt tcaaaccctc aatataggtt agtggagcct 240
ctccaaatgc agcatgagct cttgagtgta ctatcgccca atttcatatt gcacactgcc 300
aacttaagga aaattataca aagaagtgtt gacataacag ataaaaagtt gaaccccatt 360
ttgcacattt tgaatcttaa ttctcctaac caagagggta aggtgtcgga acggctaact 420
aggctaatta agaaacatct ctctcacata cctaattggg taagcagctg gtacaatata 480
tgggtcaatc ttaacaactt actgcaggag taccgttcaa aggaagttat agaccataac 540

-continued

```
tgtgttctga ctaggcaatt gtctggaagt ttcatacatg tggtcatgag tcaatatgga    600
gttgtgataa ttagcaaaaa aagtaaaaga tatacaatgt gtacttataa ccaattccta    660
acctggaagg accttgcctt gagcagattt aatgccaatt atgtggtctg gctaagtaat    720
gtgttaaaca cactcaacga ggggttggga ttaaggtgta gattaaaagg tcatctgctc    780
agtaagttgt acatttccac tgacatcttt ttatcttcaa catctaatga attttataat    840
gtggtcaagg aatttgaggg cttcatcatg tcactgatat tgaaacaaac tgaggaagcc    900
ttatttagca caaggtttta taataacatg ttgaacaact taattgatgc cattgatagg    960
gctcgactag agtatctggc ccgctgtgcc aattcagctg ccaggattaa tttacctagt   1020
acagatgtta tgatagcatc attgggtgat atcttatctt tgataaacgt tttaggtgaa   1080
tccaacctta acaacttaag tgagttatat tttatcttca ggatatttgg tcaccctatg   1140
gttgatgaga ggaaggccat ggatgcagtc agagataact gttgtgaaac aaagtttctg   1200
acggctaaga accttgcatc gttaagagga gcatatgttt atagaattat caaaggattc   1260
gtagcaaatt ataacaggtg gccttacata aaaactagag tttgccttac accaacatgg   1320
attaactatc ttgacaccaa ttcatgtccc tcattattag agatgacaga agatgatttt   1380
attgtgttag ctggagtgca ctttataaga gaattccaca tcccaaagct aactgatctg   1440
gagattatat taaatgacaa ggccatatct cctccaaaat cactcatttg gtcatgcttt   1500
ccaaaaaact acatacctca ggttatacaa gatgagtatg cccggaggta ttgtagagct   1560
aaagcacctt tgaagacaag acgtgtcttg gagttctact tacaggacaa ggatttcaag   1620
ttggatcagc tccatagagt agtagtgaac caggactacc ttaatgataa agaacatata   1680
atttctttaa caggaaaaga aagagagttg ggtgttggta ggatgtttgc catgcaacct   1740
gggaagcaga ggcaagtcca aattttagca gagaagctgt tggctgataa catcctgcaa   1800
ttctttccgg agacactgac tagatacggt gatttggagc tgcaaaagat actagagtta   1860
aaagctggac tttcaaataa aaatgacaga tctaaagact cctacaataa ttatataagt   1920
aggtgctcat taattactga tttaagtaaa tttaaccaag cttttaggta cgagtcatcc   1980
tgtgtgtgta gtgatctttt agatgagcta catgggactc aaagcttatt ctcttggctg   2040
catttaacag taccactgac tactataatg tgtacatata ggcatgcgcc gccggacact   2100
ggaaacaact ataatgtaga tgatattgct gagcagagtg gactctaccg ctaccacatg   2160
ggcgggattg agggctggtg ccagaagctc tggacaacag aggccattgc tttgctagat   2220
actgtagctg tgaagggccg tttccagcta acttcattaa taaatggcga caaccaaagt   2280
attgatattt caaaaccaac aaggctgggg accaggactc aaagtgaagc agattatgat   2340
ttggcaataa attctttaag attaatatca gcagcttata aggcattgg acataaatta    2400
aaagaaggtg agacctactt gtcacgtgac atgcagttca tgagtaaaac aatacaacat   2460
gaaggggtct actacccggc ctccatcaag aaaatattaa gagttggtcc ctggatcaac   2520
acaatattag atgatataaa aacttcaaca gaaagtattg gttctctaac tcaagaacta   2580
gaatataaag gtgaaagttt aatgagcagc ctgctgctga ggaacttctg gctctacaga   2640
ttatattcag tggatttaaa agatcattct ttgtgtggaa agcagctcta cagatcctta   2700
ataaaagtgt taaaacattt gaagaggtgc ttcaacctgg agaaccttgg ggaatgtttg   2760
gaattatttt taaatgtgcc catgcagttt ggaggtgctg acccaaatgt catctacagg   2820
agcttctaca gaagaactcc agattttcta acagaaagta taactcatct catcctcatt   2880
```

-continued

```
ttaaaacatt ttagaagaga tttggaattc aacaaagata atgtctccaa agctgttctt   2940
tctttgctag agttcaccaa gaatgattct gcagaatttg taactttgat gagagatcct   3000
caagcaattg gtagtgagag gcaggccaag atcacttcag acatcaacag aacagctgta   3060
acttcagtgt tatcaaatgc tccaaatgaa atatttagaa cttcagctct tcattacagc   3120
agcacagaaa atgaattaaa tggaatagca agtggagttt ctcctgttta tcctcatggt   3180
cttcgagttt tatatgaaag tttacctttt tataaagcag agaagattgt caacatggtt   3240
tctgggacca agtccatcac caacatactg gagaagacat cagccatctc ctacacagat   3300
ataattcgag ccaccaacat gatggtggag aacctcactt tgctaacaag aataatgaaa   3360
ccaggtgctg acacatcttt ggatcctgac acaatagtaa taacaatatt atcaaaaata   3420
ataagagata aatcctggga tgttggtgat ataattggtg tcacttcccc atctcctgtc   3480
tcctgcttca aggtggtcta cacatcaact ctacaaaata attcagtagt aatagaaaga   3540
tacacaacag acacctacac aagaggtaag agaggcccca ccaagccctg ggtgggcagc   3600
agcacacagg agaagaagtc catgcctgtc tacaacagac aagttttaac aagaggacaa   3660
agagatcaaa tagaaaatat agcaaagctg gagtgggtgt tttcttcagt agcaaatatt   3720
gattctttgc taaatgagct cagcaccatg actttgggtc tttctctaag gaaatgtaga   3780
caactttttc caacatattt aagtttaaac ttcctgcaca ggctttctgt cagcagcagg   3840
cccagagaat atccttcttc tcttcctgcc tacaggacaa caaattttca ttttgatact   3900
ggaccaataa ataaagtgtt aacagaaaga tttggagatg aagatataaa tttggtattt   3960
caaaatgcaa tatcatatgg tctttccacc atgtctttgg tggagcagtt tactggtgtc   4020
tgtccaaata aagttttgct ggtgcccaag ctacaagaaa tacaactaat gaaagttcca   4080
atatttcaag gtggcttcaa cctacaaagt ataattccaa taataaggca gcagcacatg   4140
ttcctgccca accacatcac tccagcccag tatattgaat tatttctttc ttcaaaacaa   4200
tttcattcaa gaataaattt aaaacacaac aacagattta aacttgtttt acaaaaagat   4260
tattttaatg gggagaacat gatagaaact ttgtccacct gtttggcagg ccactggatc   4320
atcattttga tgctaatgaa ggagagtcag gggatatttg acaaggagtg gtatgatggt   4380
tttgtaacag accacatgtt cctggacctg cagctcttcc tctcctcctt caagacattt   4440
ctaactgtct tcaactttgc ttatttaaaa gttggttcaa atatagaaga aataacagga   4500
aatcaagcca acctgctgga gctgctggac ctgggctact ggaagaacat gtataaagta   4560
ttttcagaga ccaaggtgcg gctggctttg ctaaaacaag atttatcatt taattctgtg   4620
aagaacagca gcagcttccg gcactggttt ataaattctc tacaagaagt acaatgtact   4680
tctgtgcctt gggtggtaaa tgtaacaaga aatccaactc atttaaaagg tgttctacag   4740
tacatgaaga tgatagaaag tggcatgatt caaggttatt cagcaaatat ttcttcagtt   4800
ttaagtatcc catataatta tccagacatg gcgcacatga tgacaaaaat aataagaaat   4860
cgaggccaca tgtcctatga ttatccaaag atgaagaaaa gtttaacttt ctccatgaca   4920
gacatgagtg acagctacat gctcaacctc ttccccaaag tagaatgttc ttacatgagt   4980
ggttatttgg ataaactaga tgatactcta caacttctaa agaaacctcc tgttggaaga   5040
aaagttcctt ctgtggcttt gccctggcac cactgcaaca gatacaactt tgtcttcagc   5100
agcacaggct gcaaagtttc tgtcattgac atgcttccaa aacatttccg aagaagtaat   5160
ttaaaagtaa tatgttttat tggagaaggg gcgggcaacc tcatgctaag agctgttttg   5220
gaagttggtg gaaatataaa attaatatat agatccttaa aagatcctga tgatcatcat   5280
```

```
gttcctgtag aatttctaag attaaaacct tgttatcctt atattgatac tggtggcagt   5340

ttatctttgg cttcaacaga tgccaccaac aaggcccact gggattattt acatcttcac   5400

tggacagatc ctttaaattt aatagtatgt gatgcagaaa taagtggtgt gaagcactgg   5460

ctaaaaattc ttcacaggtg gtatgagcac atgacttcct gcaagcactg tttaaaatca   5520

gaacatgata aatatttaat aataaaatat catgctcaag atgatttaat agatcttcct   5580

catggtgtca ggctactaaa atgtaacatc tgcctgggct ccaaactaag tggcagtgag   5640

agctacctgc tcattggtct tggtctttca aataaacttc ctgtctacag tgaagttctt   5700

cattcaaaac ttcttttggc agaatgtcat cagtttcatc atccaaaata tttggatgtt   5760

tctggaataa atacaaatat aaaatcctta ataccaatgt tggattatcc aataacttac   5820

aacaagatca ccactttgct agaaagtgtg cgggagcttt cttcaaataa aaacaagaac   5880

accatgtgga ttggaagaaa tcctgtctac cataataaat ggctaaagag gaaatatttc   5940

aacattttaa aatggctaaa atactgtata gaacttcctg ccttcaggat ggattataat   6000

tcatttgaga gaatagaaat gctttatcca aatttaagag atttggtaga ttctgtttct   6060

acttcagagc tgaagaaagt aataaaagta acaggcatcc tcttcaggag caacaccatg   6120

tga                                                                 6123
```

<210> SEQ ID NO 53
<211> LENGTH: 2040
<212> TYPE: PRT
<213> ORGANISM: Pneumonia virus of mice

<400> SEQUENCE: 53

```
Met Asp Pro Ile Asp Glu Gln Glu Val Asn Val Tyr Leu Pro Asp Ser
1               5                   10                  15

Tyr Leu Lys Gly Val Ile Ser Phe Ser Glu Thr Asn Ala Leu Gly Ser
            20                  25                  30

Cys Ile Ile Gly Arg Pro Phe Leu Lys Asp Asp Phe Thr Ala Thr Thr
        35                  40                  45

Ser Ile Arg Asn Pro Leu Ile Glu His Lys Arg Ile Arg Asp Thr Lys
    50                  55                  60

Leu Val Lys Asn Ile Val Ser Asn Pro Gln Tyr Arg Leu Val Glu Pro
65                  70                  75                  80

Leu Gln Met Gln His Glu Leu Leu Ser Val Leu Ser Pro Asn Phe Ile
                85                  90                  95

Leu His Thr Ala Asn Leu Arg Lys Ile Ile Gln Arg Ser Val Asp Ile
            100                 105                 110

Thr Asp Lys Lys Leu Asn Pro Ile Leu His Ile Leu Asn Leu Asn Ser
        115                 120                 125

Pro Asn Gln Glu Gly Lys Val Ser Glu Arg Leu Thr Arg Leu Ile Lys
    130                 135                 140

Lys His Leu Ser His Ile Pro Asn Trp Val Ser Ser Trp Tyr Asn Ile
145                 150                 155                 160

Trp Val Asn Leu Asn Asn Leu Leu Gln Glu Tyr Arg Ser Lys Glu Val
                165                 170                 175

Ile Asp His Asn Cys Val Leu Thr Arg Gln Leu Ser Gly Ser Phe Ile
            180                 185                 190

His Val Val Met Ser Gln Tyr Gly Val Val Ile Ile Ser Lys Lys Ser
        195                 200                 205

Lys Arg Tyr Thr Met Cys Thr Tyr Asn Gln Phe Leu Thr Trp Lys Asp
```

-continued

```
    210                 215                 220

Leu Ala Leu Ser Arg Phe Asn Ala Asn Tyr Val Val Trp Leu Ser Asn
225                 230                 235                 240

Val Leu Asn Thr Leu Asn Glu Gly Leu Gly Leu Arg Cys Arg Leu Lys
                245                 250                 255

Gly His Leu Leu Ser Lys Leu Tyr Ile Ser Thr Asp Ile Phe Leu Ser
            260                 265                 270

Ser Thr Ser Asn Glu Phe Tyr Asn Val Val Lys Glu Phe Glu Gly Phe
        275                 280                 285

Ile Met Ser Leu Ile Leu Lys Gln Thr Glu Glu Ala Leu Phe Ser Thr
    290                 295                 300

Arg Phe Tyr Asn Asn Met Leu Asn Asn Leu Ile Asp Ala Ile Asp Arg
305                 310                 315                 320

Ala Arg Leu Glu Tyr Leu Ala Arg Cys Ala Asn Ser Ala Ala Arg Ile
                325                 330                 335

Asn Leu Pro Ser Thr Asp Val Met Ile Ala Ser Leu Gly Asp Ile Leu
            340                 345                 350

Ser Leu Ile Asn Val Leu Gly Glu Ser Asn Leu Asn Asn Leu Ser Glu
        355                 360                 365

Leu Tyr Phe Ile Phe Arg Ile Phe Gly His Pro Met Val Asp Glu Arg
    370                 375                 380

Lys Ala Met Asp Ala Val Arg Asp Asn Cys Cys Glu Thr Lys Phe Leu
385                 390                 395                 400

Thr Ala Lys Asn Leu Ala Ser Leu Arg Gly Ala Tyr Val Tyr Arg Ile
                405                 410                 415

Ile Lys Gly Phe Val Ala Asn Tyr Asn Arg Trp Pro Tyr Ile Lys Thr
            420                 425                 430

Arg Val Cys Leu Thr Pro Thr Trp Ile Asn Tyr Leu Asp Thr Asn Ser
        435                 440                 445

Cys Pro Ser Leu Leu Glu Met Thr Glu Asp Asp Phe Ile Val Leu Ala
    450                 455                 460

Gly Val His Phe Ile Arg Glu Phe His Ile Pro Lys Leu Thr Asp Leu
465                 470                 475                 480

Glu Ile Ile Leu Asn Asp Lys Ala Ile Ser Pro Pro Lys Ser Leu Ile
                485                 490                 495

Trp Ser Cys Phe Pro Lys Asn Tyr Ile Pro Gln Val Ile Gln Asp Glu
            500                 505                 510

Tyr Ala Arg Arg Tyr Cys Arg Ala Lys Ala Pro Leu Lys Thr Arg Arg
        515                 520                 525

Val Leu Glu Phe Tyr Leu Gln Asp Lys Asp Phe Lys Leu Asp Gln Leu
    530                 535                 540

His Arg Val Val Val Asn Gln Asp Tyr Leu Asn Asp Lys Glu His Ile
545                 550                 555                 560

Ile Ser Leu Thr Gly Lys Glu Arg Glu Leu Gly Val Gly Arg Met Phe
                565                 570                 575

Ala Met Gln Pro Gly Lys Gln Arg Gln Val Gln Ile Leu Ala Glu Lys
            580                 585                 590

Leu Leu Ala Asp Asn Ile Leu Gln Phe Phe Pro Glu Thr Leu Thr Arg
        595                 600                 605

Tyr Gly Asp Leu Glu Leu Gln Lys Ile Leu Glu Leu Lys Ala Gly Leu
    610                 615                 620

Ser Asn Lys Asn Asp Arg Ser Lys Asp Ser Tyr Asn Asn Tyr Ile Ser
625                 630                 635                 640
```

Arg Cys Ser Leu Ile Thr Asp Leu Ser Lys Phe Asn Gln Ala Phe Arg
645 650 655

Tyr Glu Ser Ser Cys Val Cys Ser Asp Leu Leu Asp Glu Leu His Gly
660 665 670

Thr Gln Ser Leu Phe Ser Trp Leu His Leu Thr Val Pro Leu Thr Thr
675 680 685

Ile Met Cys Thr Tyr Arg His Ala Pro Pro Asp Thr Gly Asn Asn Tyr
690 695 700

Asn Val Asp Asp Ile Ala Glu Gln Ser Gly Leu Tyr Arg Tyr His Met
705 710 715 720

Gly Gly Ile Glu Gly Trp Cys Gln Lys Leu Trp Thr Thr Glu Ala Ile
725 730 735

Ala Leu Leu Asp Thr Val Ala Val Lys Gly Arg Phe Gln Leu Thr Ser
740 745 750

Leu Ile Asn Gly Asp Asn Gln Ser Ile Asp Ile Ser Lys Pro Thr Arg
755 760 765

Leu Gly Thr Arg Thr Gln Ser Glu Ala Asp Tyr Asp Leu Ala Ile Asn
770 775 780

Ser Leu Arg Leu Ile Ser Ala Ala Tyr Lys Gly Ile Gly His Lys Leu
785 790 795 800

Lys Glu Gly Glu Thr Tyr Leu Ser Arg Asp Met Gln Phe Met Ser Lys
805 810 815

Thr Ile Gln His Glu Gly Val Tyr Tyr Pro Ala Ser Ile Lys Lys Ile
820 825 830

Leu Arg Val Gly Pro Trp Ile Asn Thr Ile Leu Asp Asp Ile Lys Thr
835 840 845

Ser Thr Glu Ser Ile Gly Ser Leu Thr Gln Glu Leu Glu Tyr Lys Gly
850 855 860

Glu Ser Leu Met Ser Ser Leu Leu Leu Arg Asn Phe Trp Leu Tyr Arg
865 870 875 880

Leu Tyr Ser Val Asp Leu Lys Asp His Ser Leu Cys Gly Lys Gln Leu
885 890 895

Tyr Arg Ser Leu Ile Lys Val Leu Lys His Leu Lys Arg Cys Phe Asn
900 905 910

Leu Glu Asn Leu Gly Glu Cys Leu Glu Leu Phe Leu Asn Val Pro Met
915 920 925

Gln Phe Gly Gly Ala Asp Pro Asn Val Ile Tyr Arg Ser Phe Tyr Arg
930 935 940

Arg Thr Pro Asp Phe Leu Thr Glu Ser Ile Thr His Leu Ile Leu Ile
945 950 955 960

Leu Lys His Phe Arg Arg Asp Leu Glu Phe Asn Lys Asp Asn Val Ser
965 970 975

Lys Ala Val Leu Ser Leu Leu Glu Phe Thr Lys Asn Asp Ser Ala Glu
980 985 990

Phe Val Thr Leu Met Arg Asp Pro Gln Ala Ile Gly Ser Glu Arg Gln
995 1000 1005

Ala Lys Ile Thr Ser Asp Ile Asn Arg Thr Ala Val Thr Ser Val
1010 1015 1020

Leu Ser Asn Ala Pro Asn Glu Ile Phe Arg Thr Ser Ala Leu His
1025 1030 1035

Tyr Ser Ser Thr Glu Asn Glu Leu Asn Gly Ile Ala Ser Gly Val
1040 1045 1050

-continued

```
Ser Pro  Val Tyr Pro His Gly  Leu Arg Val Leu Tyr  Glu Ser Leu
    1055                 1060                 1065

Pro Phe  Tyr Lys Ala Glu Lys  Ile Val Asn Met Val  Ser Gly Thr
    1070                 1075                 1080

Lys Ser  Ile Thr Asn Ile Leu  Glu Lys Thr Ser Ala  Ile Ser Tyr
    1085                 1090                 1095

Thr Asp  Ile Ile Arg Ala Thr  Asn Met Met Val Glu  Asn Leu Thr
    1100                 1105                 1110

Leu Leu  Thr Arg Ile Met Lys  Pro Gly Ala Asp Thr  Ser Leu Asp
    1115                 1120                 1125

Pro Asp  Thr Ile Val Ile Thr  Ile Leu Ser Lys Ile  Ile Arg Asp
    1130                 1135                 1140

Lys Ser  Trp Asp Val Gly Asp  Ile Ile Gly Val Thr  Ser Pro Ser
    1145                 1150                 1155

Pro Val  Ser Cys Phe Lys Val  Val Tyr Thr Ser Thr  Leu Gln Asn
    1160                 1165                 1170

Asn Ser  Val Val Ile Glu Arg  Tyr Thr Thr Asp Thr  Tyr Thr Arg
    1175                 1180                 1185

Gly Lys  Arg Gly Pro Thr Lys  Pro Trp Val Gly Ser  Ser Thr Gln
    1190                 1195                 1200

Glu Lys  Lys Ser Met Pro Val  Tyr Asn Arg Gln Val  Leu Thr Arg
    1205                 1210                 1215

Gly Gln  Arg Asp Gln Ile Glu  Asn Ile Ala Lys Leu  Glu Trp Val
    1220                 1225                 1230

Phe Ser  Ser Val Ala Asn Ile  Asp Ser Leu Leu Asn  Glu Leu Ser
    1235                 1240                 1245

Thr Met  Thr Leu Gly Leu Ser  Leu Arg Lys Cys Arg  Gln Leu Phe
    1250                 1255                 1260

Pro Thr  Tyr Leu Ser Leu Asn  Phe Leu His Arg Leu  Ser Val Ser
    1265                 1270                 1275

Ser Arg  Pro Arg Glu Tyr Pro  Ser Ser Leu Pro Ala  Tyr Arg Thr
    1280                 1285                 1290

Thr Asn  Phe His Phe Asp Thr  Gly Pro Ile Asn Lys  Val Leu Thr
    1295                 1300                 1305

Glu Arg  Phe Gly Asp Glu Asp  Ile Asn Leu Val Phe  Gln Asn Ala
    1310                 1315                 1320

Ile Ser  Tyr Gly Leu Ser Thr  Met Ser Leu Val Glu  Gln Phe Thr
    1325                 1330                 1335

Gly Val  Cys Pro Asn Lys Val  Leu Leu Val Pro Lys  Leu Gln Glu
    1340                 1345                 1350

Ile Gln  Leu Met Lys Val Pro  Ile Phe Gln Gly Gly  Phe Asn Leu
    1355                 1360                 1365

Gln Ser  Ile Ile Pro Ile Ile  Arg Gln Gln His Met  Phe Leu Pro
    1370                 1375                 1380

Asn His  Ile Thr Pro Ala Gln  Tyr Ile Glu Leu Phe  Leu Ser Ser
    1385                 1390                 1395

Lys Gln  Phe His Ser Arg Ile  Asn Leu Lys His Asn  Asn Arg Phe
    1400                 1405                 1410

Lys Leu  Val Leu Gln Lys Asp  Tyr Phe Asn Gly Glu  Asn Met Ile
    1415                 1420                 1425

Glu Thr  Leu Ser Thr Cys Leu  Ala Gly His Trp Ile  Ile Ile Leu
    1430                 1435                 1440

Met Leu  Met Lys Glu Ser Gln  Gly Ile Phe Asp Lys  Glu Trp Tyr
```

-continued

```
    1445                1450                1455

Asp Gly  Phe Val Thr Asp His  Met Phe Leu Asp Leu  Gln Leu Phe
    1460                1465                1470

Leu Ser  Ser Phe Lys Thr Phe  Leu Thr Val Phe Asn  Phe Ala Tyr
    1475                1480                1485

Leu Lys  Val Gly Ser Asn Ile  Glu Glu Ile Thr Gly  Asn Gln Ala
    1490                1495                1500

Asn Leu  Leu Glu Leu Leu Asp  Leu Gly Tyr Trp Lys  Asn Met Tyr
    1505                1510                1515

Lys Val  Phe Ser Glu Thr Lys  Val Arg Leu Ala Leu  Leu Lys Gln
    1520                1525                1530

Asp Leu  Ser Phe Asn Ser Val  Lys Asn Ser Ser Ser  Phe Arg His
    1535                1540                1545

Trp Phe  Ile Asn Ser Leu Gln  Glu Val Gln Cys Thr  Ser Val Pro
    1550                1555                1560

Trp Val  Val Asn Val Thr Arg  Asn Pro Thr His Leu  Lys Gly Val
    1565                1570                1575

Leu Gln  Tyr Met Lys Met Ile  Glu Ser Gly Met Ile  Gln Gly Tyr
    1580                1585                1590

Ser Ala  Asn Ile Ser Ser Val  Leu Ser Ile Pro Tyr  Asn Tyr Pro
    1595                1600                1605

Asp Met  Ala His Met Met Thr  Lys Ile Ile Arg Asn  Arg Gly His
    1610                1615                1620

Met Ser  Tyr Asp Tyr Pro Lys  Met Lys Lys Ser Leu  Thr Phe Ser
    1625                1630                1635

Met Thr  Asp Met Ser Asp Ser  Tyr Met Leu Asn Leu  Phe Pro Lys
    1640                1645                1650

Val Glu  Cys Ser Tyr Met Ser  Gly Tyr Leu Asp Lys  Leu Asp Asp
    1655                1660                1665

Thr Leu  Gln Leu Leu Lys Lys  Pro Pro Val Gly Arg  Lys Val Pro
    1670                1675                1680

Ser Val  Ala Leu Pro Trp His  His Cys Asn Arg Tyr  Asn Phe Val
    1685                1690                1695

Phe Ser  Ser Thr Gly Cys Lys  Val Ser Val Ile Asp  Met Leu Pro
    1700                1705                1710

Lys His  Phe Arg Arg Ser Asn  Leu Lys Val Ile Cys  Phe Ile Gly
    1715                1720                1725

Glu Gly  Ala Gly Asn Leu Met  Leu Arg Ala Val Leu  Glu Val Gly
    1730                1735                1740

Gly Asn  Ile Lys Leu Ile Tyr  Arg Ser Leu Lys Asp  Pro Asp Asp
    1745                1750                1755

His His  Val Pro Val Glu Phe  Leu Arg Leu Lys Pro  Cys Tyr Pro
    1760                1765                1770

Tyr Ile  Asp Thr Gly Gly Ser  Leu Ser Leu Ala Ser  Thr Asp Ala
    1775                1780                1785

Thr Asn  Lys Ala His Trp Asp  Tyr Leu His Leu His  Trp Thr Asp
    1790                1795                1800

Pro Leu  Asn Leu Ile Val Cys  Asp Ala Glu Ile Ser  Gly Val Lys
    1805                1810                1815

His Trp  Leu Lys Ile Leu His  Arg Trp Tyr Glu His  Met Thr Ser
    1820                1825                1830

Cys Lys  His Cys Leu Lys Ser  Glu His Asp Lys Tyr  Leu Ile Ile
    1835                1840                1845
```

-continued

```
Lys Tyr  His Ala Gln Asp Asp  Leu Ile Asp Leu Pro  His Gly Val
    1850                 1855                 1860

Arg Leu  Leu Lys Cys Asn Ile  Cys Leu Gly Ser Lys  Leu Ser Gly
    1865                 1870                 1875

Ser Glu  Ser Tyr Leu Leu Ile  Gly Leu Gly Leu Ser  Asn Lys Leu
    1880                 1885                 1890

Pro Val  Tyr Ser Glu Val Leu  His Ser Lys Leu Leu  Leu Ala Glu
    1895                 1900                 1905

Cys His  Gln Phe His His Pro  Lys Tyr Leu Asp Val  Ser Gly Ile
    1910                 1915                 1920

Asn Thr  Asn Ile Lys Ser Leu  Ile Pro Met Leu Asp  Tyr Pro Ile
    1925                 1930                 1935

Thr Tyr  Asn Lys Ile Thr Thr  Leu Leu Glu Ser Val  Arg Glu Leu
    1940                 1945                 1950

Ser Ser  Asn Lys Asn Lys Asn  Thr Met Trp Ile Gly  Arg Asn Pro
    1955                 1960                 1965

Val Tyr  His Asn Lys Trp Leu  Lys Arg Lys Tyr Phe  Asn Ile Leu
    1970                 1975                 1980

Lys Trp  Leu Lys Tyr Cys Ile  Glu Leu Pro Ala Phe  Arg Met Asp
    1985                 1990                 1995

Tyr Asn  Ser Phe Glu Arg Ile  Glu Met Leu Tyr Pro  Asn Leu Arg
    2000                 2005                 2010

Asp Leu  Val Asp Ser Val Ser  Thr Ser Glu Leu Lys  Lys Val Ile
    2015                 2020                 2025

Lys Val  Thr Gly Ile Leu Phe  Arg Ser Asn Thr Met
    2030                 2035                 2040
```

<210> SEQ ID NO 54
<211> LENGTH: 1728
<212> TYPE: DNA
<213> ORGANISM: Human respiratory syncytial virus

<400> SEQUENCE: 54

```
atggaactgc tgatcctgaa agccaacgct attactacta tcctgaccgc cgtgacattt     60

tgcttcgcat ctggacagaa cattactgag gaattctacc agtcaacatg cagcgccgtg    120

tccaaaggat acctgagcgc cctgcggacc ggctggtata catcagtgat tactatcgag    180

ctgtccaaca tcaaggaaaa caaatgtaat gggaccgacg caaaggtgaa actgatcaag    240

caggagctgg ataagtacaa aaatgccgtg acagaactgc agctgctgat gcagtccaca    300

ccagcaacta acaatcgcgc ccggagagag ctgccccggt tcatgaacta taccctgaac    360

aatgctaaga aaaccaatgt gacactgtcc aagaaacgca agaggcgctt cctgggattt    420

ctgctgggcg tggggtctgc catcgctagt ggagtggccg tctctaaagt cctgcacctg    480

gagggcgaag tgaacaagat caaaagcgcc ctgctgtcca ctaacaaggc agtggtcagt    540

ctgtcaaatg gcgtgtccgt cctgacctct aaggtgctgg acctgaaaaa ttatattgat    600

aagcagctgc tgcctatcgt caacaaacag agctgctcca tttctaatat cgagacagtg    660

atcgaattcc agcagaagaa caatagactg ctggagatta ccagagagtt cagcgtgaac    720

gccggcgtca ccacacccgt gtccacctac atgctgacaa atagtgagct gctgtcactg    780

attaacgaca tgcctatcac caatgatcag aagaaactga tgtccaacaa tgtgcagatc    840

gtcagacagc agagttactc aatcatgtct atcattaagg aggaagtcct ggcctacgtg    900

gtccagctgc cactgtatgg cgtgatcgac accccctgct ggaaactgca tacatctcct    960
```

```
ctgtgcacta ccaacacaaa ggaaggaagt aatatctgcc tgactcgaac cgaccgggga   1020

tggtactgtg ataacgcagg cagcgtgtcc ttctttccac aggccgagac ctgcaaggtc   1080

cagagcaaca gggtgttctg tgacactatg aatagcctga ccctgccttc cgaagtcaac   1140

ctgtgcaatg tggacatctt taatccaaag tacgattgta agatcatgac tagcaagacc   1200

gatgtcagct cctctgtgat tacttctctg gggccatcg tgagttgcta cggaaagaca   1260

aaatgtactg ccagcaacaa aaatcgcggc atcattaaga ccttctccaa cgggtgcgac   1320

tatgtctcta acaagggcgt ggatacagtg agtgtcggga acactctgta ctatgtcaat   1380

aagcaggagg gaaaaagcct gtacgtgaag ggcgaaccca tcattaactt ctatgacccc   1440

ctggtgttcc cttccgacga gtttgatgca tctattagtc aggtgaacga aaaaatcaat   1500

cagagtctgg cctttattcg gaagtcagat gagctgctgc acaacgtgaa tgctggcaaa   1560

tctacaacta acatcatgat caccacaatc atcatcgtga ttatcgtcat tctgctgtca   1620

ctgatcgctg tggggctgct gctgtactgt aaggcaagaa gcaccccagt cactctgtca   1680

aaagaccagc tgtcagggat taacaacatt gccttcagta actgatag                 1728
```

```
<210> SEQ ID NO 55
<211> LENGTH: 574
<212> TYPE: PRT
<213> ORGANISM: Human respiratory syncytial virus

<400> SEQUENCE: 55

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

-continued

```
Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 56
<211> LENGTH: 1725
<212> TYPE: DNA
<213> ORGANISM: Human respiratory syncytial virus

<400> SEQUENCE: 56

```
atggagttgc taatcctcaa agcaaatgca attaccacaa tcctcactgc agtcacattt      60

tgttttgctt ctggtcaaaa catcactgaa gaattttatc aatcaacatg cagtgcagtt     120

agcaaaggct atcttagtgc tctgagaact ggttggtata ccagtgttat aactatagaa     180

ttaagtaata tcaagaaaaa taagtgtaat ggaacagatg ctaaggtaaa attgataaaa     240
```

-continued

```
caagaattag ataaatataa aaatgctgta acagaattgc agttgctcat gcaaagcaca    300

caagcaacaa acaatcgagc cagaagagaa ctaccaaggt ttatgaatta tacactcaac    360

aatgccaaaa aaaccaatgt aacattaagc aagaaaagga aaagaagatt tcttggtttt    420

ttgttaggtg ttggatctgc aatcgccagt ggcgttgctg tatctaaggt cctgcaccta    480

gaaggggaag tgaacaagat caaaagtgct ctactatcca caaacaaggc tgtagtcagc    540

ttatcaaatg gagttagtgt tttaaccagc aaagtgttag acctcaaaaa ctatatagat    600

aaacaattgt tacctattgt gaacaagcaa agctgcagca tatcaaatat agaaactgtg    660

atagagttcc aacaaaagaa caacagacta ctagagatta ccagggaatt tagtgttaat    720

gcaggcgtaa ctacacctgt aagcacttac atgttaacta atagtgaatt attgtcatta    780

atcaatgata tgcctataac aaatgatcag aaaaagttaa tgtccaacaa tgttcaaata    840

gttagacagc aaagttactc tatcatgtcc ataataaaag aggaagtctt agcatatgta    900

gtacaattac cactatatgg tgttatagat acaccctgtt ggaaactaca cacatcccct    960

ctatgtacaa ccaacacaaa agaagggtcc aacatctgtt taacaagaac tgacagagga   1020

tggtactgtg acaatgcagg atcagtatct ttcttcccac aagctgaaac atgtaaagtt   1080

caatcaaatc gagtattttg tgacacaatg aacagtttaa cattaccaag tgaagtaaat   1140

ctctgcaatg ttgacatatt caaccccaaa tatgattgta aaattatgac ttcaaaaaca   1200

gatgtaagca gctccgttat cacatctcta ggagccattg tgtcatgcta tggcaaaact   1260

aaatgtacag catccaataa aaatcgtgga atcataaaga cattttctaa cgggtgcgat   1320

tatgtatcaa ataaaggggt ggacactgtg tctgtaggta acacattata ttatgtaaat   1380

aagcaagaag gtaaaagtct ctatgtaaaa ggtgaaccaa taataaattt ctatgaccca   1440

ttagtattcc cctctgatga atttgatgca tcaatatctc aagtcaacga gaagattaac   1500

cagagcctag catttattcg taaatccgat gaattattac ataatgtaaa tgctggtaaa   1560

tccaccacaa atatcatgat aactactata attatagtga ttatagtaat attgttatca   1620

ttaattgctg ttggactgct cttatactgt aaggccagaa gcacaccagt cacactaagc   1680

aaagatcaac tgagtggtat aaataatatt gcatttagta actaa                   1725
```

<210> SEQ ID NO 57
<211> LENGTH: 574
<212> TYPE: PRT
<213> ORGANISM: Human respiratory syncytial virus

<400> SEQUENCE: 57

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110
```

-continued

```
Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525
```

-continued

```
Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 58
<211> LENGTH: 1725
<212> TYPE: DNA
<213> ORGANISM: Human respiratory syncytial virus

<400> SEQUENCE: 58

```
atggagctgc tgatccacag gttaagtgca atcttcctaa ctcttgctat taatgcattg     60

tacctcacct caagtcagaa cataactgag gagttttacc aatcgacatg tagtgcagtt    120

agcagaggtt attttagtgc tttaagaaca ggttggtata ccagtgtcat aacaatagaa    180

ttaagtaata taaaagaaac caaatgcaat ggaactgaca ctaaagtaaa acttataaaa    240

caagaattag ataagtataa gaatgcagtg acagaattac agctacttat gcaaaacaca    300

ccagctgcca acaaccgggc cagaagagaa gcaccacagt atatgaacta tacaatcaat    360

accactaaaa acctaaatgt atcaataagc aagaagagga aacgaagatt tctgggcttc    420

ttgttaggtg taggatctgc aatagcaagt ggtatagctg tatccaaagt tctacacctt    480

gaaggagaag tgaacaagat caaaaatgct ttgttatcta caaacaaagc tgtagtcagt    540

ctatcaaatg ggtcagtgt tttaaccagc aaagtgttag atctcaagaa ttacataaat    600

aaccaattat tacccatagt aaatcaacag agctgtcgca tctccaacat tgaaacagtt    660

atagaattcc agcagaagaa cagcagattg ttggaaatca acagagaatt cagtgtcaat    720

gcaggtgtaa caacaccttt aagcacttac atgttaacaa acagtgagtt actatcattg    780

atcaatgata tgcctataac aaatgatcag aaaaaattaa tgtcaagcaa tgttcagata    840

gtaaggcaac aaagttattc tatcatgtct ataataaagg aagaagtcct tgcatatgtt    900

gtacagctac ctatctatgg tgtaatagat acaccttgct ggaaattaca cacatcacct    960

ctatgcacca ccaacatcaa agaaggatca aatatttgtt taacaaggac tgatagagga   1020

tggtattgtg ataatgcagg atcagtatcc ttctttccac aggctgacac ttgtaaagta   1080

cagtccaatc gagtattttg tgacactatg aacagtttga cattaccaag tgaagtcagc   1140

ctttgtaaca ctgacatatt caattccaag tatgactgca aaattatgac atcaaaaaca   1200

gacataagca gctcagtaat tacttctctt ggagctatag tgtcatgcta tggtaaaact   1260

aaatgcactg catccaacaa aaatcgtggg attataaaga cattttctaa tggttgtgac   1320

tatgtgtcaa acaaaggagt agatactgtg tcagtgggca acactttata ctatgtaaac   1380

aagctggaag gcaagaacct ttatgtaaaa ggggaaccta taataaatta ctatgaccct   1440

ctagtgtttc cttctgatga gtttgatgca tcaatatctc aagtcaatga aaaaatcaat   1500

caaagtttag cttttattcg tagatctgat gaattactac ataatgtaaa tactggcaaa   1560

tctactacaa atattatgat aactacaatt attatagtaa tcattgtagt attgttatca   1620

ttaatagcta ttggtttgct gttgtattgc aaagccaaaa acacaccagt tacactaagc   1680

aaagaccaac taagtggaat caataatatt gcattcagca aatag                   1725
```

<210> SEQ ID NO 59
<211> LENGTH: 574
<212> TYPE: PRT

-continued

<213> ORGANISM: Human respiratory syncytial virus

<400> SEQUENCE: 59

```
Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400
```

-continued

```
Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 60
<211> LENGTH: 16658
<212> TYPE: DNA
<213> ORGANISM: Artificial Sequence
<220> FEATURE:
<223> OTHER INFORMATION: Chimeric Vector

<400> SEQUENCE: 60

```
acgcgaaaaa atgcataaca aaactatcaa cctgaaaaaa gttaggacaa gtgaagattg      60

ctagtccgcc gccaccatgg aactgctgat cctgaaagcc aacgctatta ctactatcct     120

gaccgccgtg acattttgct tcgcatctgg acagaacatt actgaggaat tctaccagtc     180

aacatgcagc gccgtgtcca aaggatacct gagcgccctg cggaccggct ggtatacatc     240

agtgattact atcgagctgt ccaacatcaa ggaaaacaaa tgtaatggga ccgacgcaaa     300

ggtgaaactg atcaagcagg agctggataa gtacaaaaat gccgtgacag aactgcagct     360

gctgatgcag tccacaccag caactaacaa tcgcgcccgg agagagctgc cccggttcat     420

gaactatacc ctgaacaatg ctaagaaaac caatgtgaca ctgtccaaga aacgcaagag     480

gcgcttcctg ggatttctgc tgggcgtggg gtctgccatc gctagtggag tggccgtctc     540

taaagtcctg cacctggagg gcgaagtgaa caagatcaaa agcgccctgc tgtccactaa     600

caaggcagtg gtcagtctgt caaatggcgt gtccgtcctg acctctaagg tgctggacct     660

gaaaaattat attgataagc agctgctgcc tatcgtcaac aaacagagct gctccatttc     720

taatatcgag acagtgatcg aattccagca gaagaacaat agactgctgg agattaccag     780

agagttcagc gtgaacgccg gcgtcaccac acccgtgtcc acctacatgc tgacaaatag     840

tgagctgctg tcactgatta acgacatgcc tatcaccaat gatcagaaga aactgatgtc     900

caacaatgtg cagatcgtca gacagcagag ttactcaatc atgtctatca ttaaggagga     960

agtcctggcc tacgtggtcc agctgccact gtatggcgtg atcgacaccc cctgctggaa    1020

actgcataca tctcctctgt gcactaccaa cacaaaggaa ggaagtaata tctgcctgac    1080
```

-continued

```
tcgaaccgac cggggatggt actgtgataa cgcaggcagc gtgtccttct ttccacaggc   1140
cgagacctgc aaggtccaga gcaacagggt gttctgtgac actatgaata gcctgaccct   1200
gccttccgaa gtcaacctgt gcaatgtgga catctttaat ccaaagtacg attgtaagat   1260
catgactagc aagaccgatg tcagctcctc tgtgattact tctctggggg ccatcgtgag   1320
ttgctacgga aagacaaaat gtactgccag caacaaaaat cgcggcatca ttaagacctt   1380
ctccaacggg tgcgactatg tctctaacaa gggcgtggat acagtgagtg tcgggaacac   1440
tctgtactat gtcaataagc aggagggaaa aagcctgtac gtgaagggcg aacccatcat   1500
taacttctat gaccccctgg tgttcccttc cgacgagttt gatgcatcta ttagtcaggt   1560
gaacgaaaaa atcaatcaga gtctggcctt tattcggaag tcagatgagc tgctgcacaa   1620
cgtgaatgct ggcaaatcta caactaacat catgatcacc acaatcatca tcgtgattat   1680
cgtcattctg ctgtcactga tcgctgtggg gctgctgctg tactgtaagg caagaagcac   1740
cccagtcact ctgtcaaaag accagctgtc agggattaac aacattgcct tcagtaactg   1800
atagtagtta attaaaacaa agggtaggac aagtccaaag accagaatca tgggctgtaa   1860
tgtgatgatg gagcttgatt atggtggacg agctgcatgg ctggcattcc acataaccaa   1920
ctttgatagg tcagatttgg aaactatcct aagaggtgct agggtgtgca atacatggca   1980
agatcagaga ctctccgtgt accttgtggg aagggattgc aatttgttaa gaccatttgt   2040
gcaagctgcc aaatttatcc ataatactag gagaggccaa acattaacac attggttcac   2100
aaaaaatatc gtgtttagtt ctacagggca agagacagag cctcccattg accccacatg   2160
tgagctgttg gtagagctga tcagtggtta agatgacagc acattatgta gttaattaaa   2220
acaaagggta ggacaagtcc taatgtccac agctatgaac aagttcactc agaccatctc   2280
taaacctgcc actatcttga atatttcaga cagtgaagag tcgggcgatg aggcaggggt   2340
gggcaaggtg tcccgtacca cacagagctc agagaggtgg cttgatttgc tcattgaaaa   2400
gttccagccg agcctacaaa acatcactag atacatcaac tggaacttca tcaggatctg   2460
caatgatagg cttaaaaaag aaaaaatggg gtacattgag gccaagcaat atgtggaaga   2520
catggcttgg atggtgatag catctgaggc agacagcatt gagtggaagt gcataaggag   2580
gcaggagaaa gtgactgggg tgaaataccc aaagttcttc tttgtacaac acaaagagga   2640
ctggattgag tgcacaggat gcattccgta cccaggccat gacttgatct atgatgagga   2700
tgatgatgac tgagctgact cagatcactc caaccagcag agagatccac cacctatagc   2760
aagtgatgta gtatttagtc tatgattagt tatagaaaaa cattaggata aatacacatc   2820
ctaggccggg ccaaaatgtc tctagacaga ttgaagctca atgatgtctc aaacaaggat   2880
agcctgctgt ccaactgcaa atacagtgtt accagatcca caggcgatgt aaccagtgtg   2940
tctggtcatg ctatgcagaa agcccttgca aggacactcg gcatgttctt acttactgcc   3000
ttcaaccgtt gcgaagaagt ggcagaaata gggctccaat atgccatgtc cttgctaggc   3060
agagatgata gcatcaagat attaagagaa gccggctaca atgtaaaatg tgtggacaca   3120
cagctcaagg actttacaat caaattacaa ggaaaggaat acaaaataca agtcctagat   3180
atagtgggaa tagatgcagc caatttagct gatctagaga tacaagccag aggagtggta   3240
gcaaaagaac tcaaaacagg agccaggcta cctgacaatc ggaggcatga tgcaccagat   3300
tgtggtgtga tagttctctg tattgcagca ttagttgttt ccaaattagc tgcaggggac   3360
aggggaggac ttgatgctgt ggaaagaagg gctttaaatg tgctgaaagc cgagaaagcc   3420
aggtacccca acatggaggt caagcagata gctgaaagtt tttatgatct gtttgaaagg   3480
```

```
aagccttatt acattgatgt cttcatcact tttggcctgg cccagtctag tgtcaaggga   3540
ggcagcaaag ttgaggggct gttttcaggt ctcttcatga atgcatacgg ggcaggacaa   3600
gttatgctga ggtggggttt actggcaaaa tctgtcaaga acatcatgct aggccatgct   3660
agtgtacaag ctgagatgga acaggtggtt gaggtttacg aatatgctca gaagcaagga   3720
ggggaggcag gattctatca catcagaaat aatccaaaag cttcacttct ctctttgacc   3780
aattgtccta atttcaccag tgttgtgctt ggcaatgctg caggtttagg catcataggg   3840
tcatataagg gtgctcctag gaatagagaa ctctttgatg ctgccaaaga ttatgcagaa   3900
agattaaagg acaacaatgt aattaactac agtgcattaa acttgactgc agaagaaaga   3960
gagctgatca gccagcagct gaacattgtt gatgacactc ctgatgatga tatttaatta   4020
aaactggaaa atgtaggata aatatggaga aattcgcccc cgaatttgtt ggcgaggatg   4080
ctaacaagaa ggcagaggag tttctcaaac atagatcctt cccttcggaa aaaccactag   4140
ctggtatacc gaacactgcc actcatgtca ccaaatataa catgcccccct atattgcgta   4200
gctcattcaa actcccttcc ccgagagttg ctgcaaatct tactgaaccc tctgctcccc   4260
ctaccactcc accacccaca cctccccaga acaaggaaga gcagcccaaa gagtctgatg   4320
ttgacattga gactatgcat gtctgtaagg ttcctgacaa tccggaacac agcaagaagc   4380
catgctgctc agatgatacc gatactaaga aaactaggaa gccgatggtc acctttgtgg   4440
aacccgagga gaaatttgtc ggattgggag ctagcttgta cagggagacc atgcagacct   4500
ttgctgctga tggttatgat gaagaaagca acctatcgtt tgaggagact aaccaagagc   4560
cgggttcttc atctgtagaa caaagactag atagaataga ggagaaattg tcctacataa   4620
taggcctttt aaacaccata atggtagcga ctgctggacc taccactgct agagatgaga   4680
ttagagatgc ccttataggc actagagaag aacttattga gatgatcaag tctgacatct   4740
tgactgtcaa tgacagaata gtggccatgg agaagctcag agatgaggaa tgctccagag   4800
ctgacactga tgatggatca gcctgttatt taacagacag agcaaggata ctagataaga   4860
tagtgtccag caatgctgaa gaggctaagg aagatttgga tgttgatgac atcatgggca   4920
ttaattttta gttaattaaa ataacaacag gacaaataat ggaggcctac ttggtagaga   4980
tgtaccatgg tgtcccatat acagctgcag tacagctaaa cttggttgaa aaacattcag   5040
ccaacatatc actaactgtg tggataccga tgtttcaaac atctctacca aagaactccg   5100
ttatggacct gctacatgat gttacagtca tttgtacaca gatatcaaca gtgcatggtc   5160
ccatgatcaa ggtagatctg agctcttcca atgcaggttt agctaccatg ccaaggcaat   5220
tcttgataaa tgctatcata gctttggatg actggggcaa catggattac gaagtgcctg   5280
ttgcttttga taaaaagagc ttctgtgtga caattcttaa gcctaaaaac atgctttaca   5340
ctgtacccag cattactccc actaatcgac ctactcatga gctgatagct gtctgctctt   5400
tccataacag ggtaacatta aagtcattca atatacctgt cttcatcaga gcactgtcta   5460
tcagacagca ggaccttgat agtgtggagc aggctataag ctccgatgtg gaccatgcta   5520
taacaacagc tagggtggct ccctatgcag ggcttacact tgtgatcaac atcacatcca   5580
ccaaaggagc attcaaactg ctaaaggcag gtagtcagat tcttgcagaa ctgggtccct   5640
atctgacgca ggtgagccta catgatgtga ttatgaactg gaaacataca ggcacttcct   5700
acatactcaa gagctcctca acaagtggat gaaaaagaga aagtcaccat tgatcagctc   5760
aatccacaac tacaacccca cgatttcaca cagcacaaca accaccgcca ccaacatcca   5820
```

-continued

```
catgacaacc acacatacac acccacatac atatatacac atatcttagt taaataaaat   5880
caggataaat aatggatcct aacatgacct cacaccagat caccctcgag atcaacatga   5940
ccagcagccg tattggcaca tacactacac cagccccaac agctcttctc cttgcatgtg   6000
ccgtcatcaa cacagtgtgt gcgctgataa tggcctgcag cagtagaagc actgccacat   6060
caggcattgt cagcagccaa tgcacagttc atcccaatca ccctccacca agttatggcg   6120
tcaatgtaac tggtctgccg ggtaacctat actcaaggaa cactacataa cattataaat   6180
aacagaaatt atccttcaat aaaccccagg ccagacagct ttaccctgct agacgattca   6240
atcagccctt gcagtatgtc gtctagttaa caaaaaaccg gtaggataag tactatccta   6300
ttggaaccaa acgagacctg tagagcagct cacacaagag aaccacaagc tgacttcacc   6360
tagtatggga aggaacttag aagtgagtgg cagcattacc aatttgaact ttgagagaac   6420
tcagcatcct gacacattta ggactgttgt aaaagtgaac caaatgtgta agcttattgc   6480
aggtgtgctc acaagtgctg ctgtggcagt ttgtgtgggg gtcataatgt attctgtttt   6540
cacatcaaac cacaaggcca actccacgca gaatgccacg acccggaaca gcacatccac   6600
ccctccccaa ccaaccgccg gtctgcccac cacagagcaa gggaccatcc ccagattcac   6660
caaacccccc accaaaaccg ccacccacca tgagatcaca gagcccgtca aaatggcaac   6720
accttcagag gatccctacc aatgctccag caatggttat ttggaccgac ctgatttacc   6780
tgaaaatttc aaactcgtat tggatgttat atgcaagcct ccaggtcctg aacatcacaa   6840
caccagctgt tatgagaaac gtgaaatcaa cccaggaagt gtttgccctg atcttgtaac   6900
aatgaaggca aacatgggct taaacaatgg tggtggggag gatgctgcac cttatataga   6960
ggttaccacc ctttctacgt actccaacaa aagggcaatg tgtgtccaca atgggtgtga   7020
tcaaggcttc tgtttcttcc tttctggttt aagcactgat caggagagag ctgtgctaga   7080
gcttggaggt caacaggcta tcatggagtt gcattatgat tcctactgga aacactattg   7140
gagtaactct aattgtgttg ttcccagaac aaactgcaac ctgacagacc aaactgagat   7200
tttgtttcct aggtttaaca acaagaatca gtctcagtgt accacctgtg cagattcagc   7260
tggcctagat aacaaatttt atctcacatg tgatgggctt ttaagaaccc tccctctagt   7320
tggactaccc agcctaagtc ctcaggctta caaagctgta cccacacaaa ctacaggcac   7380
caccacggca ccaacatcag agacgaggca cccaacccct gcacccagga ggtccaaacc   7440
tctcagtcgg aagaagagag ctttatgtgg tgtagactca agcagagaac ccaaaccaac   7500
aatgccttac tggtgtccta tgctccaatt atttccaagg aggtctaatt cttaagtgac   7560
ctattcctga attaacttca gaataagtac caaccttatc agtagttaat gaaaactaag   7620
ctttgatata ataggacaaa tatgattcct ggcaggatct ttctagtcct tctggtgatc   7680
ttcaacacca agccaattca cccaaataca ttaacagaaa aattctatga gtccacatgt   7740
agtgttgaga ctgcaggtta taagagtgcc cttagaacag gttggcatat gacagttatg   7800
tcaattaagt tgtctcaaat aaatattgag tcatgcaaga gcagcaactc gttattggct   7860
catgagcttg caatctatag tagtgcagtg gatgaattga gaacgttatc atccaatgcc   7920
ttgaagtcca aaaggaagaa gaggttcctc ggtttgattc ttggtctcgg agctgcagtc   7980
actgccgggg tggctttagc caagacagtg caacttgaaa gtgagattgc attgattaga   8040
gatgcagtga gaaatacaaa tgaggctgtt gttagcctaa ccaacggcat gtcagtgttg   8100
gctaaagtgg tggatgattt gaaaaacttc atatctaaag aattactccc aaaaataaac   8160
cgagtctctt gtgatgtgca cgacatcact gccgtcatta gattccaaca gctcaacaaa   8220
```

```
agacttttgg aagtatctcg tgaattttca tctaatgcag gattaacaca cactgtttca   8280
tcttttatgt taacagaccg ggaactcacc tccattgtag gcggcatggc tgtttcagca   8340
ggccaaaaag agataatgct atctagcaaa gctataatga gaagaaatgg gttagcaata   8400
ttaagttcag tcaacgctga cacactggtt tatgtaatac aactcccatt atttggtgtt   8460
atggacacag attgttgggt aataagaagt tctatagact gtcataacat agcagacaag   8520
tatgcttgtt tggctagagc tgataatggc tggtattgtc acaatgctgg ctcattatca   8580
tacttcccgt cgccaacgga ttgtgagatc cacaatgggt atgctttctg tgacactcta   8640
aaaagtctaa ctgtacctgt aacatcacga gaatgcaact caaacatgta taccactaac   8700
tacgattgta agatttccac aagtaaaact tatgtgagta cagcggtact gactacaatg   8760
ggttgcttgg tatcttgtta tggtcataac agttgcacag tcatcaataa tgacaaaggt   8820
ataataagga ctctgccaga tggttgccac tacatctcca acaaaggtgt ggacagggtt   8880
caagtaggta acactgttta ctatcttagc aaagaagttg gcaagtcaat tgttgtcaga   8940
ggggaaccat tggtcttgaa atatgaccct ttgagtttcc ctgacgataa atttgatgtt   9000
gctataagag atgtggagca tagcatcaat cagacacgca cattcttgaa ggcctctgat   9060
cagttattgg acttaagtga aaacagagag aataaaaatt taaacaagtc atatatacta   9120
acaactctgc tcttcgttgt aatgcttatt ataataatgg ctgtcatagg gttcattctg   9180
tataaggtat tgaaaatgat cagagacaac aagttgaaat ccaaaagtac acctggcctc   9240
acagttttat catgacaatt gtaccaaacc ataattgagt tagttaatta aaaacttagg   9300
ataagtgaca atccagaccc aacacctctt tcaactctca aggataaggt aggatgagtg   9360
tgagaccttg caaatttgag gttcaagggt tttgttccag agggaggaat tgcaagtata   9420
gtcataaata ttgggaatgg cctttgaaaa ctcttatgct caggcagaac tacatgctta   9480
ataggattta taggttcctc gacaccaaca cagatgcaat gtcagatgtc agcggatttg   9540
atgcaccaca aaggactgct gagtatgcct tgggaaccat aggtgtgctg aaaagttacc   9600
tggaaaaaac taacaacatc actaaatcaa tagcttgtgg cagtttgatc actgtattgc   9660
agaacttgga tgttggtcta gtaatacaag caagagatag caacactgag gacaccaatt   9720
acttgagaag ttgcaacact atactgtctt atatagacaa gatacacaag aagagacaaa   9780
ttattcacat tctcaaaaga ctgccagtag gagtactatg caatctgatc caatctgtca   9840
tctccatcga ggagaagata aattcttcta tgaaaacaga atgataaggc tgcctaaata   9900
ctatccagcc atactgcata agatgtatat tattagagta aatagaaacc tcacttacga   9960
tgggtctgga ccatccacaa taatagatgc aggaaagtct gtggtgtgga atcgtgttga  10020
tgtgatagct tgtgtgaaag aggccttgtg ctgcatagaa ttcagctgga ataaccaagt  10080
gatcatagac tttgattata gccaggccag atgatgtgga ctgtattcct tttttgtca   10140
gtaatcagtt attaacccaa aattgttaat tatgtagact ttaagttaac taacttcatg  10200
ttaattcaat agttatataa aaaaatattc gaattaggat caatatggat cctattgatg  10260
aacaagaagt taatgtgtac ttgccggata gctacttaaa gggtgttata tcttttagtg  10320
aaactaatgc tcttggcagc tgtatcattg gtagaccttt cttgaaggat gactttactg  10380
ccactacttc aatccgtaac cccctaattg aacataaaag aataagggac actaaattag  10440
taaaaaatat tgtttcaaac cctcaatata ggttagtgga gcctctccaa atgcagcatg  10500
agctcttgag tgtactatcg cccaatttca tattgcacac tgccaactta aggaaaatta  10560
```

-continued tacaaagaag tgttgacata acagataaaa agttgaaccc cattttgcac attttgaatc 10620
ttaattctcc taaccaagag ggtaaggtgt cggaacggct aactaggcta attaagaaac 10680
atctctctca catacctaat tgggtaagca gctggtacaa tatatgggtc aatcttaaca 10740
acttactgca ggagtaccgt tcaaaggaag ttatagacca taactgtgtt ctgactaggc 10800
aattgtctgg aagtttcata catgtggtca tgagtcaata tggagttgtg ataattagca 10860
aaaaaagtaa aagatataca atgtgtactt ataaccaatt cctaacctgg aaggaccttg 10920
ccttgagcag atttaatgcc aattatgtgg tctggctaag taatgtgtta aacacactca 10980
acgaggggtt gggattaagg tgtagattaa aaggtcatct gctcagtaag ttgtacattt 11040
ccactgacat ctttttatct tcaacatcta atgaatttta taatgtggtc aaggaatttg 11100
agggcttcat catgtcactg atattgaaac aaactgagga agccttattt agcacaaggt 11160
tttataataa catgttgaac aacttaattg atgccattga tagggctcga ctagagtatc 11220
tggcccgctg tgccaattca gctgccagga ttaatttacc tagtacagat gttatgatag 11280
catcattggg tgatatctta tctttgataa acgttttagg tgaatccaac cttaacaact 11340
taagtgagtt atattttatc ttcaggatat ttggtcaccc tatggttgat gagaggaagg 11400
ccatggatgc agtcagagat aactgttgtg aaacaaagtt tctgacggct aagaaccttg 11460
catcgttaag aggagcatat gtttatagaa ttatcaaagg attcgtagca aattataaca 11520
ggtggcctta cataaaaact agagtttgcc ttacaccaac atggattaac tatcttgaca 11580
ccaattcatg tccctcatta ttagagatga cagaagatga ttttattgtg ttagctggag 11640
tgcactttat aagagaattc cacatcccaa agctaactga tctggagatt atattaaatg 11700
acaaggccat atctcctcca aaatcactca tttggtcatg ctttccaaaa aactacatac 11760
ctcaggttat acaagatgag tatgcccgga ggtattgtag agctaaagca cctttgaaga 11820
caagacgtgt cttggagttc tacttacagg acaaggattt caagttggat cagctccata 11880
gagtagtagt gaaccaggac taccttaatg ataaagaaca tataatttct ttaacaggaa 11940
aagaaagaga gttgggtgtt ggtaggatgt ttgccatgca acctgggaag cagaggcaag 12000
tccaaatttt agcagagaag ctgttggctg ataacatcct gcaattcttt ccggagacac 12060
tgactagata cggtgatttg gagctgcaaa agatactaga gttaaaagct ggactttcaa 12120
ataaaaatga cagatctaaa gactcctaca ataattatat aagtaggtgc tcattaatta 12180
ctgatttaag taaatttaac caagctttta ggtacgagtc atcctgtgtg tgtagtgatc 12240
ttttagatga gctacatggg actcaaagct tattctcttg gctgcattta acagtaccac 12300
tgactactat aatgtgtaca tataggcatg cgccgccgga cactggaaac aactataatg 12360
tagatgatat tgctgagcag agtggactct accgctacca catgggcggg attgagggct 12420
ggtgccagaa gctctggaca acagaggcca ttgctttgct agatactgta gctgtgaagg 12480
gccgtttcca gctaacttca ttaataaatg gcgacaacca aagtattgat atttcaaaac 12540
caacaaggct ggggaccagg actcaaagtg aagcagatta tgatttggca ataaattctt 12600
taagattaat atcagcagct tataaaggca ttggacataa attaaaagaa ggtgagacct 12660
acttgtcacg tgacatgcag ttcatgagta aaacaataca acatgaaggg gtctactacc 12720
cggcctccat caagaaaata ttaagagttg gtccctggat caacacaata ttagatgata 12780
taaaaacttc aacagaaagt attggttctc taactcaaga actagaatat aaaggtgaaa 12840
gtttaatgag cagcctgctg ctgaggaact tctggctcta cagattatat tcagtggatt 12900
taaaagatca ttctttgtgt ggaaagcagc tctacagatc cttaataaaa gtgttaaaac 12960

```
atttgaagag gtgcttcaac ctggagaacc ttggggaatg tttggaatta tttttaaatg  13020
tgcccatgca gtttggaggt gctgacccaa atgtcatcta caggagcttc tacagaagaa  13080
ctccagattt tctaacagaa agtataactc atctcatcct cattttaaaa cattttagaa  13140
gagatttgga attcaacaaa gataatgtct ccaaagctgt tctttctttg ctagagttca  13200
ccaagaatga ttctgcagaa tttgtaactt tgatgagaga tcctcaagca attggtagtg  13260
agaggcaggc caagatcact tcagacatca acagaacagc tgtaacttca gtgttatcaa  13320
atgctccaaa tgaaatattt agaacttcag ctcttcatta cagcagcaca gaaaatgaat  13380
taaatggaat agcaagtgga gtttctcctg tttatcctca tggtcttcga gttttatatg  13440
aaagtttacc tttttataaa gcagagaaga ttgtcaacat ggtttctggg accaagtcca  13500
tcaccaacat actggagaag acatcagcca tctcctacac agatataatt cgagccacca  13560
acatgatggt ggagaacctc actttgctaa caagaataat gaaaccaggt gctgacacat  13620
ctttggatcc tgacacaata gtaataacaa tattatcaaa aataataaga gataaatcct  13680
gggatgttgg tgatataatt ggtgtcactt ccccatctcc tgtctcctgc ttcaaggtgg  13740
tctacacatc aactctacaa aataattcag tagtaataga aagatacaca acagacacct  13800
acacaagagg taagagaggc cccaccaagc cctgggtggg cagcagcaca caggagaaga  13860
agtccatgcc tgtctacaac agacaagttt taacaagagg acaaagagat caaatagaaa  13920
atatagcaaa gctggagtgg gtgttttctt cagtagcaaa tattgattct ttgctaaatg  13980
agctcagcac catgactttg ggtctttctc taaggaaatg tagacaactt tttccaacat  14040
atttaagttt aaacttcctg cacaggcttt ctgtcagcag caggcccaga gaatatcctt  14100
cttctcttcc tgcctacagg acaacaaatt ttcattttga tactggacca ataaataaag  14160
tgttaacaga aagatttgga gatgaagata taaatttggt atttcaaaat gcaatatcat  14220
atggtctttc caccatgtct ttggtggagc agtttactgg tgtctgtcca aataaagttt  14280
tgctggtgcc caagctacaa gaaatacaac taatgaaagt tccaatattt caaggtggct  14340
tcaacctaca aagtataatt ccaataataa ggcagcagca catgttcctg cccaaccaca  14400
tcactccagc ccagtatatt gaattatttc tttcttcaaa acaatttcat tcaagaataa  14460
atttaaaaca caacaacaga tttaaacttg ttttacaaaa agattatttt aatgggggaga  14520
acatgataga aactttgtcc acctgtttgg caggccactg gatcatcatt ttgatgctaa  14580
tgaaggagag tcaggggata tttgacaagg agtggtatga tggttttgta acagaccaca  14640
tgttcctgga cctgcagctc ttcctctcct ccttcaagac atttctaact gtcttcaact  14700
ttgcttattt aaaagttggt tcaaatatag aagaaataac aggaaatcaa gccaacctgc  14760
tggagctgct ggacctgggc tactggaaga acatgtataa agtattttca gagaccaagg  14820
tgcggctggc tttgctaaaa caagatttat catttaattc tgtgaagaac agcagcagct  14880
tccggcactg gtttataaat tctctacaag aagtacaatg tacttctgtg ccttgggtgg  14940
taaatgtaac aagaaatcca actcatttaa aaggtgttct acagtacatg aagatgatag  15000
aaagtggcat gattcaaggt tattcagcaa atatttcttc agttttaagt atcccatata  15060
attatccaga catggcgcac atgatgacaa aaataataag aaatcgaggc cacatgtcct  15120
atgattatcc aaagatgaag aaaagtttaa ctttctccat gacagacatg agtgacagct  15180
acatgctcaa cctcttcccc aaagtagaat gttcttacat gagtggttat ttggataaac  15240
tagatgatac tctacaactt ctaaagaaac ctcctgttgg aagaaaagtt ccttctgtgg  15300
```

-continued

```
ctttgccctg gcaccactgc aacagataca actttgtctt cagcagcaca ggctgcaaag  15360

tttctgtcat tgacatgctt ccaaaacatt tccgaagaag taatttaaaa gtaatatgtt  15420

ttattggaga aggggcgggc aacctcatgc taagagctgt tttggaagtt ggtggaaata  15480

taaaattaat atatagatcc ttaaaagatc ctgatgatca tcatgttcct gtagaatttc  15540

taagattaaa accttgttat ccttatattg atactggtgg cagtttatct ttggcttcaa  15600

cagatgccac caacaaggcc cactgggatt atttacatct tcactggaca gatcctttaa  15660

atttaatagt atgtgatgca gaaataagtg gtgtgaagca ctggctaaaa attcttcaca  15720

ggtggtatga gcacatgact tcctgcaagc actgtttaaa atcagaacat gataaatatt  15780

taataataaa atatcatgct caagatgatt taatagatct tcctcatggt gtcaggctac  15840

taaaatgtaa catctgcctg ggctccaaac taagtggcag tgagagctac ctgctcattg  15900

gtcttggtct ttcaaataaa cttcctgtct acagtgaagt tcttcattca aaacttcttt  15960

tggcagaatg tcatcagttt catcatccaa aatatttgga tgtttctgga ataaatacaa  16020

atataaaatc cttaatacca atgttggatt atccaataac ttacaacaag atcaccactt  16080

tgctagaaag tgtgcgggag ctttcttcaa ataaaaacaa gaacaccatg tggattggaa  16140

gaaatcctgt ctaccataat aaatggctaa agaggaaata tttcaacatt ttaaaatggc  16200

taaaatactg tatagaactt cctgccttca ggatggatta taattcattt gagagaatag  16260

aaatgcttta tccaaattta agagatttgg tagattctgt ttctacttca gagctgaaga  16320

aagtaataaa agtaacaggc atcctcttca ggagcaacac catgtgaatt aatatgccaa  16380

tgctaacatg tcatccccac tacttttttt gttcaatcac tctcagtcta gacatgtgag  16440

aagatcccaa acccaactgc acccctccca ctcgaaatca gttgtagcct cagcagctcc  16500

atctgccatg atctctgacc agcagcaaat gtattattat tttaatttgt ctatagttaa  16560

caaaaaattg atatctcaca ggttgtaaac atagttcttt tataattatt gttagttaaa  16620

ctattgtgtt tgacttcctt tgggtatttt tttcccgt                          16658
```

<210> SEQ ID NO 61
<211> LENGTH: 16655
<212> TYPE: DNA
<213> ORGANISM: Artificial Sequence
<220> FEATURE:
<223> OTHER INFORMATION: Chimeric Vector

<400> SEQUENCE: 61

```
acgcgaaaaa atgcataaca aaactatcaa cctgaaaaaa gttaggacaa gtgaagattg     60

ctagtcccaa agaccagaat catgggctgt aatgtgatga tggagcttga ttatggtgga    120

cgagctgcat ggctggcatt ccacataacc aactttgata ggtcagattt ggaaactatc    180

ctaagaggtg ctagggtgtg caatacatgg caagatcaga gactctccgt gtaccttgtg    240

ggaagggatt gcaatttgtt aagaccattt gtgcaagctg ccaaatttat ccataatact    300

aggagaggcc aaacattaac acattggttc acaaaaaata tcgtgtttag ttctacaggg    360

caagagacag agcctcccat tgaccccaca tgtgagctgt tggtagagct gatcagtggt    420

taagatgaca gcacattatg tagttaatta aaacaaaggg taggacaagt cctaatgtcc    480

acagctatga acaagttcac tcagaccatc tctaaacctg ccactatctt gaatatttca    540

gacagtgaag agtcgggcga tgaggcaggg gtgggcaagg tgtcccgtac cacacagagc    600

tcagagaggt ggcttgattt gctcattgaa aagttccagc cgagcctaca aaacatcact    660

agatacatca actggaactt catcaggatc tgcaatgata ggcttaaaaa agaaaaaatg    720
```

-continued

```
gggtacattg aggccaagca atatgtggaa gacatggctt ggatggtgat agcatctgag    780
gcagacagca ttgagtggaa gtgcataagg aggcaggaga aagtgactgg ggtgaaatac    840
ccaaagttct tctttgtaca acacaaagag gactggattg agtgcacagg atgcattccg    900
tacccaggcc atgacttgat ctatgatgag gatgatgatg actgagctga ctcagatcac    960
tccaaccagc agagagatcc atagttatag aaaaacatta ggataaatac acatcctagg   1020
ccgccaccat ggaactgctg atcctgaaag ccaacgctat tactactatc ctgaccgccg   1080
tgacattttg cttcgcatct ggacagaaca ttactgagga attctaccag tcaacatgca   1140
gcgccgtgtc caaaggatac ctgagcgccc tgcggaccgg ctggtataca tcagtgatta   1200
ctatcgagct gtccaacatc aaggaaaaca aatgtaatgg gaccgacgca aaggtgaaac   1260
tgatcaagca ggagctggat aagtacaaaa atgccgtgac agaactgcag ctgctgatgc   1320
agtccacacc agcaactaac aatcgcgccc ggagagagct gccccggttc atgaactata   1380
ccctgaacaa tgctaagaaa accaatgtga cactgtccaa gaaacgcaag aggcgcttcc   1440
tgggatttct gctgggcgtg gggtctgcca tcgctagtgg agtggccgtc tctaaagtcc   1500
tgcacctgga gggcgaagtg aacaagatca aaagcgccct gctgtccact aacaaggcag   1560
tggtcagtct gtcaaatggc gtgtccgtcc tgacctctaa ggtgctggac ctgaaaaatt   1620
atattgataa gcagctgctg cctatcgtca acaaacagag ctgctccatt tctaatatcg   1680
agacagtgat cgaattccag cagaagaaca atagactgct ggagattacc agagagttca   1740
gcgtgaacgc cggcgtcacc acacccgtgt ccacctacat gctgacaaat agtgagctgc   1800
tgtcactgat taacgacatg cctatcacca atgatcagaa gaaactgatg tccaacaatg   1860
tgcagatcgt cagacagcag agttactcaa tcatgtctat cattaaggag gaagtcctgg   1920
cctacgtggt ccagctgcca ctgtatggcg tgatcgacac cccctgctgg aaactgcata   1980
catctcctct gtgcactacc aacacaaagg aaggaagtaa tatctgcctg actcgaaccg   2040
accggggatg gtactgtgat aacgcaggca gcgtgtcctt ctttccacag gccgagacct   2100
gcaaggtcca gagcaacagg gtgttctgtg acactatgaa tagcctgacc ctgccttccg   2160
aagtcaacct gtgcaatgtg gacatcttta atccaaagta cgattgtaag atcatgacta   2220
gcaagaccga tgtcagctcc tctgtgatta cttctctggg ggccatcgtg agttgctacg   2280
gaaagacaaa atgtactgcc agcaacaaaa atcgcggcat cattaagacc ttctccaacg   2340
ggtgcgacta tgtctctaac aagggcgtgg atacagtgag tgtcgggaac actctgtact   2400
atgtcaataa gcaggaggga aaaagcctgt acgtgaaggg cgaacccatc attaacttct   2460
atgacccccct ggtgttccct tccgacgagt ttgatgcatc tattagtcag gtgaacgaaa   2520
aaatcaatca gagtctggcc tttattcgga agtcagatga gctgctgcac aacgtgaatg   2580
ctggcaaatc tacaactaac atcatgatca ccacaatcat catcgtgatt atcgtcattc   2640
tgctgtcact gatcgctgtg ggctgctgc tgtactgtaa ggcaagaagc accccagtca   2700
ctctgtcaaa agaccagctg tcagggatta acaacattgc cttcagtaac tgatagccac   2760
ctatagcaag tgatgtagta tttagtctat gattagttat agaaaaacat taggataaat   2820
agccgggcca aaatgtctct agacagattg aagctcaatg atgtctcaaa caaggatagc   2880
ctgctgtcca actgcaaata cagtgttacc agatccacag gcgatgtaac cagtgtgtct   2940
ggtcatgcta tgcagaaagc ccttgcaagg acactcggca tgttcttact tactgccttc   3000
aaccgttgcg aagaagtggc agaaataggg ctccaatatg ccatgtcctt gctaggcaga   3060
```

-continued gatgatagca tcaagatatt aagagaagcc ggctacaatg taaaatgtgt ggacacacag 3120
ctcaaggact ttacaatcaa attacaagga aaggaataca aaatacaagt cctagatata 3180
gtgggaatag atgcagccaa tttagctgat ctagagatac aagccagagg agtggtagca 3240
aaagaactca aaacaggagc caggctacct gacaatcgga ggcatgatgc accagattgt 3300
ggtgtgatag ttctctgtat tgcagcatta gttgtttcca aattagctgc aggggacagg 3360
ggaggacttg atgctgtgga aagaagggct ttaaatgtgc tgaaagccga gaaagccagg 3420
taccccaaca tggaggtcaa gcagatagct gaaagttttt atgatctgtt tgaaaggaag 3480
ccttattaca ttgatgtctt catcactttt ggcctggccc agtctagtgt caagggaggc 3540
agcaaagttg aggggctgtt ttcaggtctc ttcatgaatg catacggggc aggacaagtt 3600
atgctgaggt ggggtttact ggcaaaatct gtcaagaaca tcatgctagg ccatgctagt 3660
gtacaagctg agatggaaca ggtggttgag gtttacgaat atgctcagaa gcaaggaggg 3720
gaggcaggat tctatcacat cagaaataat ccaaaagctt cacttctctc tttgaccaat 3780
tgtcctaatt tcaccagtgt tgtgcttggc aatgctgcag gtttaggcat catagggtca 3840
tataagggtg ctcctaggaa tagagaactc tttgatgctg ccaaagatta tgcagaaaga 3900
ttaaaggaca acaatgtaat taactacagt gcattaaact tgactgcaga agaaagagag 3960
ctgatcagcc agcagctgaa cattgttgat gacactcctg atgatgatat ttaattaaaa 4020
ctggaaaatg taggataaat atggagaaat tcgcccccga atttgttggc gaggatgcta 4080
acaagaaggc agaggagttt ctcaaacata gatccttccc ttcggaaaaa ccactagctg 4140
gtataccgaa cactgccact catgtcacca aatataacat gccccctata ttgcgtagct 4200
cattcaaact cccttccccg agagttgctg caaatcttac tgaaccctct gctcccccta 4260
ccactccacc acccacacct ccccagaaca aggaagagca gcccaaagag tctgatgttg 4320
acattgagac tatgcatgtc tgtaaggttc ctgacaatcc ggaacacagc aagaagccat 4380
gctgctcaga tgataccgat actaagaaaa ctaggaagcc gatggtcacc tttgtggaac 4440
ccgaggagaa atttgtcgga ttgggagcta gcttgtacag ggagaccatg cagacctttg 4500
ctgctgatgg ttatgatgaa gaaagcaacc tatcgtttga ggagactaac caagagccgg 4560
gttcttcatc tgtagaacaa agactagata gaatagagga gaaattgtcc tacataatag 4620
gcctttttaa caccataatg gtagcgactg ctggacctac cactgctaga gatgagatta 4680
gagatgccct tataggcact agagaagaac ttattgagat gatcaagtct gacatcttga 4740
ctgtcaatga cagaatagtg gccatggaga agctcagaga tgaggaatgc tccagagctg 4800
acactgatga tggatcagcc tgttatttaa cagacagagc aaggatacta gataagatag 4860
tgtccagcaa tgctgaagag gctaaggaag atttggatgt tgatgacatc atgggcatta 4920
atttttagtt aattaaaata acaacaggac aaataatgga ggcctacttg gtagagatgt 4980
accatggtgt cccatataca gctgcagtac agctaaactt ggttgaaaaa cattcagcca 5040
acatatcact aactgtgtgg ataccgatgt ttcaaacatc tctaccaaag aactccgtta 5100
tggacctgct acatgatgtt acagtcattt gtacacagat atcaacagtg catggtccca 5160
tgatcaaggt agatctgagc tcttccaatg caggtttagc taccatgcca aggcaattct 5220
tgataaatgc tatcatagct ttggatgact ggggcaacat ggattacgaa gtgcctgttg 5280
cttttgataa aaagagcttc tgtgtgacaa ttcttaagcc taaaaacatg ctttacactg 5340
tacccagcat tactcccact aatcgaccta ctcatgagct gatagctgtc tgctctttcc 5400
ataacagggt aacattaaag tcattcaata tacctgtctt catcagagca ctgtctatca 5460

```
gacagcagga ccttgatagt gtggagcagg ctataagctc cgatgtggac catgctataa   5520
caacagctag ggtggctccc tatgcagggc ttacacttgt gatcaacatc acatccacca   5580
aaggagcatt caaactgcta aaggcaggta gtcagattct tgcagaactg ggtccctatc   5640
tgacgcaggt gagcctacat gatgtgatta tgaactggaa acatacaggc acttcctaca   5700
tactcaagag ctcctcaaca agtggatgaa aaagagaaag tcaccattga tcagctcaat   5760
ccacaactac aaccccacga tttcacacag cacaacaacc accgccacca acatccacat   5820
gacaaccaca catacacacc cacatacata tatacacata tcttagttaa ataaaatcag   5880
gataaataat ggatcctaac atgacctcac accagatcac cctcgagatc aacatgacca   5940
gcagccgtat tggcacatac actacaccag ccccaacagc tcttctcctt gcatgtgccg   6000
tcatcaacac agtgtgtgcg ctgataatgg cctgcagcag tagaagcact gccacatcag   6060
gcattgtcag cagccaatgc acagttcatc ccaatcaccc tccaccaagt tatggcgtca   6120
atgtaactgg tctgccgggt aacctatact caaggaacac tacataacat tataaataac   6180
agaaattatc cttcaataaa ccccaggcca gacagcttta ccctgctaga cgattcaatc   6240
agcccttgca gtatgtcgtc tagttaacaa aaaaccggta ggataagtac tatcctattg   6300
gaaccaaacg agacctgtag agcagctcac acaagagaac cacaagctga cttcacctag   6360
tatgggaagg aacttagaag tgagtggcag cattaccaat ttgaactttg agagaactca   6420
gcatcctgac acatttagga ctgttgtaaa agtgaaccaa atgtgtaagc ttattgcagg   6480
tgtgctcaca agtgctgctg tggcagtttg tgtgggggtc ataatgtatt ctgttttcac   6540
atcaaaccac aaggccaact ccacgcagaa tgccacgacc cggaacagca catccacccc   6600
tccccaacca accgccggtc tgcccaccac agagcaaggg accatcccca gattcaccaa   6660
accccccacc aaaaccgcca cccaccatga gatcacagag cccgtcaaaa tggcaacacc   6720
ttcagaggat ccctaccaat gctccagcaa tggttatttg gaccgacctg atttacctga   6780
aaatttcaaa ctcgtattgg atgttatatg caagcctcca ggtcctgaac atcacaacac   6840
cagctgttat gagaaacgtg aaatcaaccc aggaagtgtt tgccctgatc ttgtaacaat   6900
gaaggcaaac atgggcttaa acaatggtgg tggggaggat gctgcacctt atatagaggt   6960
taccaccctt tctacgtact ccaacaaaag ggcaatgtgt gtccacaatg ggtgtgatca   7020
aggcttctgt ttcttccttt ctggtttaag cactgatcag gagagagctg tgctagagct   7080
tggaggtcaa caggctatca tggagttgca ttatgattcc tactggaaac actattggag   7140
taactctaat tgtgttgttc ccagaacaaa ctgcaacctg acagaccaaa ctgagatttt   7200
gtttcctagg tttaacaaca agaatcagtc tcagtgtacc acctgtgcag attcagctgg   7260
cctagataac aaattttatc tcacatgtga tgggctttta agaaccctcc ctctagttgg   7320
actacccagc ctaagtcctc aggcttacaa agctgtaccc acacaaacta caggcaccac   7380
cacggcacca acatcagaga cgaggcaccc aacccctgca cccaggaggt ccaaacctct   7440
cagtcggaag aagagagctt tatgtggtgt agactcaagc agagaaccca aaccaacaat   7500
gccttactgg tgtcctatgc tccaattatt tccaaggagg tctaattctt aagtgaccta   7560
ttcctgaatt aacttcagaa taagtaccaa ccttatcagt agttaatgaa aactaagctt   7620
tgatataata ggacaaatat gattcctggc aggatctttc tagtccttct ggtgatcttc   7680
aacaccaagc caattcaccc aaatacatta acagaaaaat tctatgagtc cacatgtagt   7740
gttgagactg caggttataa gagtgccctt agaacaggtt ggcatatgac agttatgtca   7800
```

-continued

```
attaagttgt ctcaaataaa tattgagtca tgcaagagca gcaactcgtt attggctcat   7860
gagcttgcaa tctatagtag tgcagtggat gaattgagaa cgttatcatc caatgccttg   7920
aagtccaaaa ggaagaagag gttcctcggt ttgattcttg gtctcggagc tgcagtcact   7980
gccggggtgg ctttagccaa gacagtgcaa cttgaaagtg agattgcatt gattagagat   8040
gcagtgagaa atacaaatga ggctgttgtt agcctaacca acggcatgtc agtgttggct   8100
aaagtggtgg atgatttgaa aacttcata tctaaagaat tactcccaaa aataaaccga    8160
gtctcttgtg atgtgcacga catcactgcc gtcattagat tccaacagct caacaaaaga   8220
cttttggaag tatctcgtga attttcatct aatgcaggat taacacacac tgtttcatct   8280
tttatgttaa cagaccggga actcacctcc attgtaggcg gcatggctgt ttcagcaggc   8340
caaaaagaga taatgctatc tagcaaagct ataatgagaa gaaatgggtt agcaatatta   8400
agttcagtca acgctgacac actggtttat gtaatacaac tcccattatt tggtgttatg   8460
gacacagatt gttgggtaat aagaagttct atagactgtc ataacatagc agacaagtat   8520
gcttgtttgg ctagagctga taatggctgg tattgtcaca atgctggctc attatcatac   8580
ttcccgtcgc caacggattg tgagatccac aatgggtatg ctttctgtga cactctaaaa   8640
agtctaactg tacctgtaac atcacgagaa tgcaactcaa acatgtatac cactaactac   8700
gattgtaaga tttccacaag taaaacttat gtgagtacag cggtactgac tacaatgggt   8760
tgcttggtat cttgttatgg tcataacagt tgcacagtca tcaataatga caaaggtata   8820
ataaggactc tgccagatgg ttgccactac atctccaaca aaggtgtgga cagggttcaa   8880
gtaggtaaca ctgtttacta tcttagcaaa gaagttggca agtcaattgt tgtcagaggg   8940
gaaccattgg tcttgaaata tgaccctttg agtttccctg acgataaatt tgatgttgct   9000
ataagagatg tggagcatag catcaatcag acacgcacat tcttgaaggc ctctgatcag   9060
ttattggact taagtgaaaa cagagagaat aaaaatttaa acaagtcata tatactaaca   9120
actctgctct tcgttgtaat gcttattata ataatggctg tcatagggtt cattctgtat   9180
aaggtattga aatgatcag agacaacaag ttgaaatcca aaagtacacc tggcctcaca    9240
gttttatcat gacaattgta ccaaaccata attgagttag ttaattaaaa acttaggata   9300
agtgacaatc cagacccaac acctctttca actctcaagg ataaggtagg atgagtgtga   9360
gaccttgcaa atttgaggtt caagggtttt gttccagagg gaggaattgc aagtatagtc   9420
ataaatattg ggaatggcct ttgaaaactc ttatgctcag gcagaactac atgcttaata   9480
ggatttatag gttcctcgac accaacacag atgcaatgtc agatgtcagc ggatttgatg   9540
caccacaaag gactgctgag tatgccttgg gaaccatagg tgtgctgaaa agttacctgg   9600
aaaaaactaa caacatcact aaatcaatag cttgtggcag tttgatcact gtattgcaga   9660
acttggatgt tggtctagta atacaagcaa gagatagcaa cactgaggac accaattact   9720
tgagaagttg caacactata ctgtcttata tagacaagat acacaagaag agacaaatta   9780
ttcacattct caaaagactg ccagtaggag tactatgcaa tctgatccaa tctgtcatct   9840
ccatcgagga gaagataaat tcttctatga aaacagaatg ataaggctgc ctaaatacta   9900
tccagccata ctgcataaga tgtatattat tagagtaaat agaaacctca cttacgatgg   9960
gtctggacca tccacaataa tagatgcagg aaagtctgtg gtgtggaatc gtgttgatgt  10020
gatagcttgt gtgaaagagg ccttgtgctg catagaattc agctggaata accaagtgat  10080
catagacttt gattatagcc aggccagatg atgtggactg tattcctttt tttgtcagta  10140
atcagttatt aacccaaaat tgttaattat gtagacttta agttaactaa cttcatgtta  10200
```

```
attcaatagt tatataaaaa aatattcgaa ttaggatcaa tatggatcct attgatgaac  10260
aagaagttaa tgtgtacttg ccggatagct acttaaaggg tgttatatct tttagtgaaa  10320
ctaatgctct tggcagctgt atcattggta gacctttctt gaaggatgac tttactgcca  10380
ctacttcaat ccgtaacccc ctaattgaac ataaaagaat aagggacact aaattagtaa  10440
aaaatattgt ttcaaaccct caatataggt tagtggagcc tctccaaatg cagcatgagc  10500
tcttgagtgt actatcgccc aatttcatat tgcacactgc caacttaagg aaaattatac  10560
aaagaagtgt tgacataaca gataaaaagt tgaaccccat tttgcacatt ttgaatctta  10620
attctcctaa ccaagagggt aaggtgtcgg aacggctaac taggctaatt aagaaacatc  10680
tctctcacat acctaattgg gtaagcagct ggtacaatat atgggtcaat cttaacaact  10740
tactgcagga gtaccgttca aaggaagtta tagaccataa ctgtgttctg actaggcaat  10800
tgtctggaag tttcatacat gtggtcatga gtcaatatgg agttgtgata attagcaaaa  10860
aaagtaaaag atatacaatg tgtacttata accaattcct aacctggaag gaccttgcct  10920
tgagcagatt taatgccaat tatgtggtct ggctaagtaa tgtgttaaac acactcaacg  10980
aggggttggg attaaggtgt agattaaaag gtcatctgct cagtaagttg tacatttcca  11040
ctgacatctt tttatcttca acatctaatg aattttataa tgtggtcaag gaatttgagg  11100
gcttcatcat gtcactgata ttgaaacaaa ctgaggaagc cttatttagc acaaggtttt  11160
ataataacat gttgaacaac ttaattgatg ccattgatag ggctcgacta gagtatctgg  11220
cccgctgtgc caattcagct gccaggatta atttacctag tacagatgtt atgatagcat  11280
cattgggtga tatcttatct ttgataaacg ttttaggtga atccaacctt aacaacttaa  11340
gtgagttata ttttatcttc aggatatttg gtcaccctat ggttgatgag aggaaggcca  11400
tggatgcagt cagagataac tgttgtgaaa caaagtttct gacggctaag aaccttgcat  11460
cgttaagagg agcatatgtt tatagaatta tcaaaggatt cgtagcaaat tataacaggt  11520
ggccttacat aaaaactaga gtttgcctta caccaacatg gattaactat cttgacacca  11580
attcatgtcc ctcattatta gagatgacag aagatgattt tattgtgtta gctggagtgc  11640
actttataag agaattccac atcccaaagc taactgatct ggagattata ttaaatgaca  11700
aggccatatc tcctccaaaa tcactcattt ggtcatgctt tccaaaaaac tacatacctc  11760
aggttataca agatgagtat gcccggaggt attgtagagc taaagcacct ttgaagacaa  11820
gacgtgtctt ggagttctac ttacaggaca aggatttcaa gttggatcag ctccatagag  11880
tagtagtgaa ccaggactac cttaatgata aagaacatat aatttcttta acaggaaaag  11940
aaagagagtt gggtgttggt aggatgtttg ccatgcaacc tgggaagcag aggcaagtcc  12000
aaattttagc agagaagctg ttggctgata acatcctgca attctttccg gagacactga  12060
ctagatacgg tgatttggag ctgcaaaaga tactagagtt aaaagctgga ctttcaaata  12120
aaaatgacag atctaaagac tcctacaata attatataag taggtgctca ttaattactg  12180
atttaagtaa atttaaccaa gcttttaggt acgagtcatc ctgtgtgtgt agtgatcttt  12240
tagatgagct acatgggact caaagcttat tctcttggct gcatttaaca gtaccactga  12300
ctactataat gtgtacatat aggcatgcgc cgccggacac tggaaacaac tataatgtag  12360
atgatattgc tgagcagagt ggactctacc gctaccacat gggcgggatt gagggctggt  12420
gccagaagct ctggacaaca gaggccattg ctttgctaga tactgtagct gtgaagggcc  12480
gtttccagct aacttcatta ataaatggcg acaaccaaag tattgatatt tcaaaaccaa  12540
```

-continued caaggctggg gaccaggact caaagtgaag cagattatga tttggcaata aattctttaa 12600
gattaatatc agcagcttat aaaggcattg gacataaatt aaaagaaggt gagacctact 12660
tgtcacgtga catgcagttc atgagtaaaa caatacaaca tgaaggggtc tactacccgg 12720
cctccatcaa gaaaatatta agagttggtc cctggatcaa cacaatatta gatgatataa 12780
aaacttcaac agaaagtatt ggttctctaa ctcaagaact agaatataaa ggtgaaagtt 12840
taatgagcag cctgctgctg aggaacttct ggctctacag attatattca gtggatttaa 12900
aagatcattc tttgtgtgga aagcagctct acagatcctt aataaaagtg ttaaaacatt 12960
tgaagaggtg cttcaacctg gagaaccttg gggaatgttt ggaattattt ttaaatgtgc 13020
ccatgcagtt tggaggtgct gacccaaatg tcatctacag gagcttctac agaagaactc 13080
cagattttct aacagaaagt ataactcatc tcatcctcat tttaaaacat tttagaagag 13140
atttggaatt caacaaagat aatgtctcca aagctgttct ttctttgcta gagttcacca 13200
agaatgattc tgcagaattt gtaactttga tgagagatcc tcaagcaatt ggtagtgaga 13260
ggcaggccaa gatcacttca gacatcaaca gaacagctgt aacttcagtg ttatcaaatg 13320
ctccaaatga aatatttaga acttcagctc ttcattacag cagcacagaa aatgaattaa 13380
atggaatagc aagtggagtt tctcctgttt atcctcatgg tcttcgagtt ttatatgaaa 13440
gtttaccttt ttataaagca gagaagattg tcaacatggt ttctgggacc aagtccatca 13500
ccaacatact ggagaagaca tcagccatct cctacacaga tataattcga gccaccaaca 13560
tgatggtgga gaacctcact ttgctaacaa gaataatgaa accaggtgct gacacatctt 13620
tggatcctga cacaatagta ataacaatat tatcaaaaat aataagagat aaatcctggg 13680
atgttggtga tataattggt gtcacttccc catctcctgt ctcctgcttc aaggtggtct 13740
acacatcaac tctacaaaat aattcagtag taatagaaag atacacaaca gacacctaca 13800
caagaggtaa gagaggcccc accaagccct gggtgggcag cagcacacag gagaagaagt 13860
ccatgcctgt ctacaacaga caagttttaa caagaggaca aagagatcaa atagaaaata 13920
tagcaaagct ggagtgggtg ttttcttcag tagcaaatat tgattctttg ctaaatgagc 13980
tcagcaccat gactttgggt ctttctctaa ggaaatgtag acaacttttt ccaacatatt 14040
taagtttaaa cttcctgcac aggctttctg tcagcagcag gcccagagaa tatccttctt 14100
ctcttcctgc ctacaggaca acaaattttc attttgatac tggaccaata aataaagtgt 14160
taacagaaag atttggagat gaagatataa atttggtatt tcaaaatgca atatcatatg 14220
gtctttccac catgtctttg gtggagcagt ttactggtgt ctgtccaaat aaagttttgc 14280
tggtgcccaa gctacaagaa atacaactaa tgaaagttcc aatatttcaa ggtggcttca 14340
acctacaaag tataattcca ataataaggc agcagcacat gttcctgccc aaccacatca 14400
ctccagccca gtatattgaa ttatttcttt cttcaaaaca atttcattca agaataaatt 14460
taaaacacaa caacagattt aaacttgttt tacaaaaaga ttattttaat ggggagaaca 14520
tgatagaaac tttgtccacc tgtttggcag gccactggat catcattttg atgctaatga 14580
aggagagtca ggggatattt gacaaggagt ggtatgatgg ttttgtaaca gaccacatgt 14640
tcctggacct gcagctcttc ctctcctcct tcaagacatt tctaactgtc ttcaactttg 14700
cttatttaaa agttggttca aatatagaag aaataacagg aaatcaagcc aacctgctgg 14760
agctgctgga cctgggctac tggaagaaca tgtataaagt attttcagag accaaggtgc 14820
ggctggcttt gctaaaacaa gatttatcat ttaattctgt gaagaacagc agcagcttcc 14880
ggcactggtt tataaattct ctacaagaag tacaatgtac ttctgtgcct tgggtggtaa 14940
atgtaacaag aaatccaact catttaaaag gtgttctaca gtacatgaag atgatagaaa 15000
gtggcatgat tcaaggttat tcagcaaata tttcttcagt tttaagtatc ccatataatt 15060
atccagacat ggcgcacatg atgacaaaaa taataagaaa tcgaggccac atgtcctatg 15120
attatccaaa gatgaagaaa agtttaactt tctccatgac agacatgagt gacagctaca 15180
tgctcaacct cttccccaaa gtagaatgtt cttacatgag tggttatttg gataaactag 15240
atgatactct acaacttcta aagaaacctc ctgttggaag aaaagttcct tctgtggctt 15300
tgccctggca ccactgcaac agatacaact ttgtcttcag cagcacaggc tgcaaagttt 15360
ctgtcattga catgcttcca aaacatttcc gaagaagtaa tttaaaagta atatgtttta 15420
ttggagaagg ggcgggcaac ctcatgctaa gagctgtttt ggaagttggt ggaaatataa 15480
aattaatata tagatcctta aaagatcctg atgatcatca tgttcctgta gaatttctaa 15540
gattaaaacc ttgttatcct tatattgata ctggtggcag tttatctttg gcttcaacag 15600
atgccaccaa caaggcccac tgggattatt tacatcttca ctggacagat cctttaaatt 15660
taatagtatg tgatgcagaa ataagtggtg tgaagcactg gctaaaaatt cttcacaggt 15720
ggtatgagca catgacttcc tgcaagcact gtttaaaatc agaacatgat aaatatttaa 15780
taataaaata tcatgctcaa gatgatttaa tagatcttcc tcatggtgtc aggctactaa 15840
aatgtaacat ctgcctgggc tccaaactaa gtggcagtga gagctacctg ctcattggtc 15900
ttggtctttc aaataaactt cctgtctaca gtgaagttct tcattcaaaa cttcttttgg 15960
cagaatgtca tcagtttcat catccaaaat atttggatgt ttctggaata aatacaaata 16020
taaaatcctt aataccaatg ttggattatc caataactta caacaagatc accactttgc 16080
tagaaagtgt gcgggagctt tcttcaaata aaaacaagaa caccatgtgg attggaagaa 16140
atcctgtcta ccataataaa tggctaaaga ggaaatattt caacatttta aaatggctaa 16200
aatactgtat agaacttcct gccttcagga tggattataa ttcatttgag agaatagaaa 16260
tgctttatcc aaatttaaga gatttggtag attctgtttc tacttcagag ctgaagaaag 16320
taataaaagt aacaggcatc ctcttcagga gcaacaccat gtgaattaat atgccaatgc 16380
taacatgtca tccccactac tttttttgtt caatcactct cagtctagac atgtgagaag 16440
atcccaaacc caactgcacc cctcccactc gaaatcagtt gtagcctcag cagctccatc 16500
tgccatgatc tctgaccagc agcaaatgta ttattatttt aatttgtcta tagttaacaa 16560
aaaattgata tctcacaggt tgtaaacata gttcttttat aattattgtt agttaaacta 16620
ttgtgtttga cttcctttgg gtattttttt cccgt 16655

<210> SEQ ID NO 62
<211> LENGTH: 16661
<212> TYPE: DNA
<213> ORGANISM: Artificial Sequence
<220> FEATURE:
<223> OTHER INFORMATION: Chimeric Vector

<400> SEQUENCE: 62
acgcgaaaaa atgcataaca aaactatcaa cctgaaaaaa gttaggacaa gtgaagattg 60
ctagtcccaa agaccagaat catgggctgt aatgtgatga tggagcttga ttatggtgga 120
cgagctgcat ggctggcatt ccacataacc aactttgata ggtcagattt ggaaactatc 180
ctaagaggtg ctagggtgtg caatacatgg caagatcaga gactctccgt gtaccttgtg 240
ggaagggatt gcaatttgtt aagaccattt gtgcaagctg ccaaatttat ccataatact 300

-continued

```
aggagaggcc aaacattaac acattggttc acaaaaaata tcgtgtttag ttctacaggg    360
caagagacag agcctcccat tgaccccaca tgtgagctgt tggtagagct gatcagtggt    420
taagatgaca gcacattatg tagttaatta aaacaaaggg taggacaagt cctaatgtcc    480
acagctatga acaagttcac tcagaccatc tctaaacctg ccactatctt gaatatttca    540
gacagtgaag agtcgggcga tgaggcaggg gtgggcaagg tgtcccgtac cacacagagc    600
tcagagaggt ggcttgattt gctcattgaa aagttccagc cgagcctaca aaacatcact    660
agatacatca actggaactt catcaggatc tgcaatgata ggcttaaaaa agaaaaaatg    720
gggtacattg aggccaagca atatgtggaa gacatggctt ggatggtgat agcatctgag    780
gcagacagca ttgagtggaa gtgcataagg aggcaggaga aagtgactgg ggtgaaatac    840
ccaaagttct tctttgtaca acacaaagag gactggattg agtgcacagg atgcattccg    900
tacccaggcc atgacttgat ctatgatgag gatgatgatg actgagctga ctcagatcac    960
tccaaccagc agagagatcc accacctata gcaagtgatg tagtatttag tctatgatta   1020
gttatagaaa aacattagga taaatacaca tcctaggccg ggccaaaatg tctctagaca   1080
gattgaagct caatgatgtc tcaaacaagg atagcctgct gtccaactgc aaatacagtg   1140
ttaccagatc cacaggcgat gtaaccagtg tgtctggtca tgctatgcag aaagcccttg   1200
caaggacact cggcatgttc ttacttactg ccttcaaccg ttgcgaagaa gtggcagaaa   1260
tagggctcca atatgccatg tccttgctag gcagagatga tagcatcaag atattaagag   1320
aagccggcta caatgtaaaa tgtgtggaca cacagctcaa ggactttaca atcaaattac   1380
aaggaaagga atacaaaata caagtcctag atatagtggg aatagatgca gccaatttag   1440
ctgatctaga gatacaagcc agaggagtgg tagcaaaaga actcaaaaca ggagccaggc   1500
tacctgacaa tcggaggcat gatgcaccag attgtggtgt gatagttctc tgtattgcag   1560
cattagttgt ttccaaatta gctgcagggg acaggggagg acttgatgct gtggaaagaa   1620
gggctttaaa tgtgctgaaa gccgagaaag ccaggtaccc caacatggag gtcaagcaga   1680
tagctgaaag tttttatgat ctgtttgaaa ggaagcctta ttacattgat gtcttcatca   1740
cttttggcct ggcccagtct agtgtcaagg gaggcagcaa agttgagggg ctgttttcag   1800
gtctcttcat gaatgcatac ggggcaggac aagttatgct gaggtggggt ttactggcaa   1860
aatctgtcaa gaacatcatg ctaggccatg ctagtgtaca agctgagatg gaacaggtgg   1920
ttgaggttta cgaatatgct cagaagcaag gaggggaggc aggattctat cacatcagaa   1980
ataatccaaa agcttcactt ctctctttga ccaattgtcc taatttcacc agtgttgtgc   2040
ttggcaatgc tgcaggttta ggcatcatag ggtcatataa gggtgctcct aggaatagag   2100
aactctttga tgctgccaaa gattatgcag aaagattaaa ggacaacaat gtaattaact   2160
acagtgcatt aaacttgact gcagaagaaa gagagctgat cagccagcag ctgaacattg   2220
ttgatgacac tcctgatgat gatatttaat taaaactgga aaatgtagga taaatagccg   2280
ccaccatgga actgctgatc ctgaaagcca acgctattac tactatcctg accgccgtga   2340
cattttgctt cgcatctgga cagaacatta ctgaggaatt ctaccagtca acatgcagcg   2400
ccgtgtccaa aggatacctg agcgccctgc ggaccggctg gtatacatca gtgattacta   2460
tcgagctgtc caacatcaag gaaaacaaat gtaatgggac cgacgcaaag gtgaaactga   2520
tcaagcagga gctggataag tacaaaaatg ccgtgacaga actgcagctg ctgatgcagt   2580
ccacaccagc aactaacaat cgcgcccgga gagagctgcc ccggttcatg aactataccc   2640
tgaacaatgc taagaaaacc aatgtgacac tgtccaagaa acgcaagagg cgcttcctgg   2700
```

-continued gatttctgct gggcgtgggg tctgccatcg ctagtggagt ggccgtctct aaagtcctgc 2760
acctggaggg cgaagtgaac aagatcaaaa gcgccctgct gtccactaac aaggcagtgg 2820
tcagtctgtc aaatggcgtg tccgtcctga cctctaaggt gctggacctg aaaaattata 2880
ttgataagca gctgctgcct atcgtcaaca aacagagctg ctccatttct aatatcgaga 2940
cagtgatcga attccagcag aagaacaata gactgctgga gattaccaga gagttcagcg 3000
tgaacgccgg cgtcaccaca cccgtgtcca cctacatgct gacaaatagt gagctgctgt 3060
cactgattaa cgacatgcct atcaccaatg atcagaagaa actgatgtcc aacaatgtgc 3120
agatcgtcag acagcagagt tactcaatca tgtctatcat taaggaggaa gtcctggcct 3180
acgtggtcca gctgccactg tatggcgtga tcgacacccc ctgctggaaa ctgcatacat 3240
ctcctctgtg cactaccaac acaaaggaag gaagtaatat ctgcctgact cgaaccgacc 3300
ggggatggta ctgtgataac gcaggcagcg tgtccttctt tccacaggcc gagacctgca 3360
aggtccagag caacagggtg ttctgtgaca ctatgaatag cctgaccctg ccttccgaag 3420
tcaacctgtg caatgtggac atctttaatc caaagtacga ttgtaagatc atgactagca 3480
agaccgatgt cagctcctct gtgattactt ctctgggggc catcgtgagt tgctacggaa 3540
agacaaaatg tactgccagc aacaaaaatc gcggcatcat taagaccttc tccaacgggt 3600
gcgactatgt ctctaacaag ggcgtggata cagtgagtgt cgggaacact ctgtactatg 3660
tcaataagca ggagggaaaa agcctgtacg tgaagggcga acccatcatt aacttctatg 3720
accccctggt gttcccttcc gacgagtttg atgcatctat tagtcaggtg aacgaaaaaa 3780
tcaatcagag tctggccttt attcggaagt cagatgagct gctgcacaac gtgaatgctg 3840
gcaaatctac aactaacatc atgatcacca caatcatcat cgtgattatc gtcattctgc 3900
tgtcactgat cgctgtgggg ctgctgctgt actgtaaggc aagaagcacc ccagtcactc 3960
tgtcaaaaga ccagctgtca gggattaaca acattgcctt cagtaactga tagtatttaa 4020
ttaaaactgg aaaatgtagg ataaatatgg agaaattcgc ccccgaattt gttggcgagg 4080
atgctaacaa gaaggcagag gagtttctca aacatagatc cttcccttcg gaaaaaccac 4140
tagctggtat accgaacact gccactcatg tcaccaaata taacatgccc cctatattgc 4200
gtagctcatt caaactccct tccccgagag ttgctgcaaa tcttactgaa ccctctgctc 4260
cccctaccac tccaccaccc acacctcccc agaacaagga agagcagccc aaagagtctg 4320
atgttgacat tgagactatg catgtctgta aggttcctga caatccggaa cacagcaaga 4380
agccatgctg ctcagatgat accgatacta agaaaactag gaagccgatg gtcacctttg 4440
tggaacccga ggagaaattt gtcggattgg gagctagctt gtacagggag accatgcaga 4500
cctttgctgc tgatggttat gatgaagaaa gcaacctatc gtttgaggag actaaccaag 4560
agccgggttc ttcatctgta gaacaaagac tagatagaat agaggagaaa ttgtcctaca 4620
taataggcct tttaaacacc ataatggtag cgactgctgg acctaccact gctagagatg 4680
agattagaga tgcccttata ggcactagag aagaacttat tgagatgatc aagtctgaca 4740
tcttgactgt caatgacaga atagtggcca tggagaagct cagagatgag gaatgctcca 4800
gagctgacac tgatgatgga tcagcctgtt atttaacaga cagagcaagg atactagata 4860
agatagtgtc cagcaatgct gaagaggcta aggaagattt ggatgttgat gacatcatgg 4920
gcattaattt ttagttaatt aaaataacaa caggacaaat aatggaggcc tacttggtag 4980
agatgtacca tggtgtccca tatacagctg cagtacagct aaacttggtt gaaaaacatt 5040

-continued

```
cagccaacat atcactaact gtgtggatac cgatgtttca aacatctcta ccaaagaact   5100
ccgttatgga cctgctacat gatgttacag tcatttgtac acagatatca acagtgcatg   5160
gtcccatgat caaggtagat ctgagctctt ccaatgcagg tttagctacc atgccaaggc   5220
aattcttgat aaatgctatc atagctttgg atgactgggg caacatggat tacgaagtgc   5280
ctgttgcttt tgataaaaag agcttctgtg tgacaattct taagcctaaa aacatgcttt   5340
acactgtacc cagcattact cccactaatc gacctactca tgagctgata gctgtctgct   5400
ctttccataa cagggtaaca ttaaagtcat tcaatatacc tgtcttcatc agagcactgt   5460
ctatcagaca gcaggacctt gatagtgtgg agcaggctat aagctccgat gtggaccatg   5520
ctataacaac agctagggtg gctccctatg cagggcttac acttgtgatc aacatcacat   5580
ccaccaaagg agcattcaaa ctgctaaagg caggtagtca gattcttgca gaactgggtc   5640
cctatctgac gcaggtgagc ctacatgatg tgattatgaa ctggaaacat acaggcactt   5700
cctacatact caagagctcc tcaacaagtg gatgaaaaag agaaagtcac cattgatcag   5760
ctcaatccac aactacaacc ccacgatttc acacagcaca acaaccaccg ccaccaacat   5820
ccacatgaca accacacata cacacccaca tacatatata cacatatctt agttaaataa   5880
aatcaggata aataatggat cctaacatga cctcacacca gatcaccctc gagatcaaca   5940
tgaccagcag ccgtattggc acatacacta caccagcccc aacagctctt ctccttgcat   6000
gtgccgtcat caacacagtg tgtgcgctga taatggcctg cagcagtaga agcactgcca   6060
catcaggcat tgtcagcagc caatgcacag ttcatcccaa tcaccctcca ccaagttatg   6120
gcgtcaatgt aactggtctg ccgggtaacc tatactcaag gaacactaca taacattata   6180
aataacagaa attatccttc aataaacccc aggccagaca gctttaccct gctagacgat   6240
tcaatcagcc cttgcagtat gtcgtctagt taacaaaaaa ccggtaggat aagtactatc   6300
ctattggaac caaacgagac ctgtagagca gctcacacaa gagaaccaca agctgacttc   6360
acctagtatg ggaaggaact tagaagtgag tggcagcatt accaatttga actttgagag   6420
aactcagcat cctgacacat ttaggactgt tgtaaaagtg aaccaaatgt gtaagcttat   6480
tgcaggtgtg ctcacaagtg ctgctgtggc agtttgtgtg gggtcataa tgtattctgt   6540
tttcacatca aaccacaagg ccaactccac gcagaatgcc acgacccgga acagcacatc   6600
cacccctccc caaccaaccg ccggtctgcc caccacagag caagggacca tccccagatt   6660
caccaaaccc cccaccaaaa ccgccaccca ccatgagatc acagagcccg tcaaaatggc   6720
aacaccttca gaggatccct accaatgctc cagcaatggt tatttggacc gacctgattt   6780
acctgaaaat ttcaaactcg tattggatgt tatatgcaag cctccaggtc ctgaacatca   6840
caacaccagc tgttatgaga aacgtgaaat caacccagga agtgtttgcc ctgatcttgt   6900
aacaatgaag gcaaacatgg gcttaaacaa tggtggtggg gaggatgctg caccttatat   6960
agaggttacc accctttcta cgtactccaa caaaagggca atgtgtgtcc acaatgggtg   7020
tgatcaaggc ttctgtttct tcctttctgg tttaagcact gatcaggaga gagctgtgct   7080
agagcttgga ggtcaacagg ctatcatgga gttgcattat gattcctact ggaaacacta   7140
ttggagtaac tctaattgtg ttgttcccag aacaaactgc aacctgacag accaaactga   7200
gattttgttt cctaggttta acaacaagaa tcagtctcag tgtaccacct gtgcagattc   7260
agctggccta gataacaaat tttatctcac atgtgatggg cttttaagaa ccctccctct   7320
agttggacta cccagcctaa gtcctcaggc ttacaaagct gtacccacac aaactacagg   7380
caccaccacg gcaccaacat cagagacgag gcacccaacc cctgcaccca ggaggtccaa   7440
```

-continued

```
acctctcagt cggaagaaga gagctttatg tggtgtagac tcaagcagag aacccaaacc   7500
aacaatgcct tactggtgtc ctatgctcca attatttcca aggaggtcta attcttaagt   7560
gacctattcc tgaattaact tcagaataag taccaacctt atcagtagtt aatgaaaact   7620
aagctttgat ataataggac aaatatgatt cctggcagga tctttctagt ccttctggtg   7680
atcttcaaca ccaagccaat tcacccaaat acattaacag aaaaattcta tgagtccaca   7740
tgtagtgttg agactgcagg ttataagagt gcccttagaa caggttggca tatgacagtt   7800
atgtcaatta agttgtctca aataaatatt gagtcatgca agagcagcaa ctcgttattg   7860
gctcatgagc ttgcaatcta tagtagtgca gtggatgaat tgagaacgtt atcatccaat   7920
gccttgaagt ccaaaaggaa gaagaggttc ctcggtttga ttcttggtct cggagctgca   7980
gtcactgccg gggtggcttt agccaagaca gtgcaacttg aaagtgagat tgcattgatt   8040
agagatgcag tgagaaatac aaatgaggct gttgttagcc taaccaacgg catgtcagtg   8100
ttggctaaag tggtggatga tttgaaaaac ttcatatcta aagaattact cccaaaaata   8160
aaccgagtct cttgtgatgt gcacgacatc actgccgtca ttagattcca acagctcaac   8220
aaaagacttt tggaagtatc tcgtgaattt tcatctaatg caggattaac acacactgtt   8280
tcatctttta tgttaacaga ccgggaactc acctccattg taggcggcat ggctgtttca   8340
gcaggccaaa aagagataat gctatctagc aaagctataa tgagaagaaa tgggttagca   8400
atattaagtt cagtcaacgc tgacacactg gtttatgtaa tacaactccc attatttggt   8460
gttatggaca cagattgttg ggtaataaga agttctatag actgtcataa catagcagac   8520
aagtatgctt gtttggctag agctgataat ggctggtatt gtcacaatgc tggctcatta   8580
tcatacttcc cgtcgccaac ggattgtgag atccacaatg ggtatgcttt ctgtgacact   8640
ctaaaaagtc taactgtacc tgtaacatca cgagaatgca actcaaacat gtataccact   8700
aactacgatt gtaagatttc cacaagtaaa acttatgtga gtacagcggt actgactaca   8760
atgggttgct tggtatcttg ttatggtcat aacagttgca cagtcatcaa taatgacaaa   8820
ggtataataa ggactctgcc agatggttgc cactacatct ccaacaaagg tgtggacagg   8880
gttcaagtag gtaacactgt ttactatctt agcaaagaag ttggcaagtc aattgttgtc   8940
agaggggaac cattggtctt gaaatatgac cctttgagtt tccctgacga taaatttgat   9000
gttgctataa gagatgtgga gcatagcatc aatcagacac gcacattctt gaaggcctct   9060
gatcagttat tggacttaag tgaaaacaga gagaataaaa atttaaacaa gtcatatata   9120
ctaacaactc tgctcttcgt tgtaatgctt attataataa tggctgtcat agggttcatt   9180
ctgtataagg tattgaaaat gatcagagac aacaagttga aatccaaaag tacacctggc   9240
ctcacagttt tatcatgaca attgtaccaa accataattg agttagttaa ttaaaaactt   9300
aggataagtg acaatccaga cccaacacct ctttcaactc tcaaggataa ggtaggatga   9360
gtgtgagacc ttgcaaattt gaggttcaag ggttttgttc cagagggagg aattgcaagt   9420
atagtcataa atattgggaa tggcctttga aaactcttat gctcaggcag aactacatgc   9480
ttaataggat ttataggttc ctcgacacca acacagatgc aatgtcagat gtcagcggat   9540
ttgatgcacc acaaaggact gctgagtatg ccttgggaac cataggtgtg ctgaaaagtt   9600
acctggaaaa aactaacaac atcactaaat caatagcttg tggcagtttg atcactgtat   9660
tgcagaactt ggatgttggt ctagtaatac aagcaagaga tagcaacact gaggacacca   9720
attacttgag aagttgcaac actatactgt cttatataga caagatacac aagaagagac   9780
```

```
aaattattca cattctcaaa agactgccag taggagtact atgcaatctg atccaatctg   9840
tcatctccat cgaggagaag ataaattctt ctatgaaaac agaatgataa ggctgcctaa   9900
atactatcca gccatactgc ataagatgta tattattaga gtaaatagaa acctcactta   9960
cgatgggtct ggaccatcca caataataga tgcaggaaag tctgtggtgt ggaatcgtgt  10020
tgatgtgata gcttgtgtga aagaggcctt gtgctgcata gaattcagct ggaataacca  10080
agtgatcata gactttgatt atagccaggc cagatgatgt ggactgtatt cctttttttg  10140
tcagtaatca gttattaacc caaaattgtt aattatgtag actttaagtt aactaacttc  10200
atgttaattc aatagttata taaaaaaata ttcgaattag gatcaatatg gatcctattg  10260
atgaacaaga agttaatgtg tacttgccgg atagctactt aaagggtgtt atatctttta  10320
gtgaaactaa tgctcttggc agctgtatca ttggtagacc tttcttgaag gatgacttta  10380
ctgccactac ttcaatccgt aaccccctaa ttgaacataa aagaataagg gacactaaat  10440
tagtaaaaaa tattgtttca aaccctcaat ataggttagt ggagcctctc caaatgcagc  10500
atgagctctt gagtgtacta tcgcccaatt tcatattgca cactgccaac ttaaggaaaa  10560
ttatacaaag aagtgttgac ataacagata aaaagttgaa ccccattttg cacattttga  10620
atcttaattc tcctaaccaa gagggtaagg tgtcggaacg gctaactagg ctaattaaga  10680
aacatctctc tcacatacct aattgggtaa gcagctggta caatatatgg gtcaatctta  10740
acaacttact gcaggagtac cgttcaaagg aagttataga ccataactgt gttctgacta  10800
ggcaattgtc tggaagtttc atacatgtgg tcatgagtca atatggagtt gtgataatta  10860
gcaaaaaaag taaaagatat acaatgtgta cttataacca attcctaacc tggaaggacc  10920
ttgccttgag cagatttaat gccaattatg tggtctggct aagtaatgtg ttaaacacac  10980
tcaacgaggg gttgggatta aggtgtagat taaaaggtca tctgctcagt aagttgtaca  11040
tttccactga catcttttta tcttcaacat ctaatgaatt ttataatgtg gtcaaggaat  11100
ttgagggctt catcatgtca ctgatattga aacaaactga ggaagcctta tttagcacaa  11160
ggttttataa taacatgttg aacaacttaa ttgatgccat tgatagggct cgactagagt  11220
atctggcccg ctgtgccaat tcagctgcca ggattaattt acctagtaca gatgttatga  11280
tagcatcatt gggtgatatc ttatctttga taaacgtttt aggtgaatcc aaccttaaca  11340
acttaagtga gttatatttt atcttcagga tatttggtca ccctatggtt gatgagagga  11400
aggccatgga tgcagtcaga gataactgtt gtgaaacaaa gtttctgacg gctaagaacc  11460
ttgcatcgtt aagaggagca tatgtttata gaattatcaa aggattcgta gcaaattata  11520
acaggtggcc ttacataaaa actagagttt gccttacacc aacatggatt aactatcttg  11580
acaccaattc atgtccctca ttattagaga tgacagaaga tgattttatt gtgttagctg  11640
gagtgcactt tataagagaa ttccacatcc caaagctaac tgatctggag attatattaa  11700
atgacaaggc catatctcct ccaaaatcac tcatttggtc atgctttcca aaaaactaca  11760
tacctcaggt tatacaagat gagtatgccc ggaggtattg tagagctaaa gcacctttga  11820
agacaagacg tgtcttggag ttctacttac aggacaagga tttcaagttg gatcagctcc  11880
atagagtagt agtgaaccag gactacctta atgataaaga acatataatt tctttaacag  11940
gaaaagaaag agagttgggt gttggtagga tgtttgccat gcaacctggg aagcagaggc  12000
aagtccaaat tttagcagag aagctgttgg ctgataacat cctgcaattc tttccggaga  12060
cactgactag atacggtgat ttggagctgc aaaagatact agagttaaaa gctggacttt  12120
caaataaaaa tgacagatct aaagactcct acaataatta tataagtagg tgctcattaa  12180
```

-continued

```
ttactgattt aagtaaattt aaccaagctt ttaggtacga gtcatcctgt gtgtgtagtg  12240
atcttttaga tgagctacat gggactcaaa gcttattctc ttggctgcat ttaacagtac  12300
cactgactac tataatgtgt acatataggc atgcgccgcc ggacactgga aacaactata  12360
atgtagatga tattgctgag cagagtggac tctaccgcta ccacatgggc gggattgagg  12420
gctggtgcca gaagctctgg acaacagagg ccattgcttt gctagatact gtagctgtga  12480
agggccgttt ccagctaact tcattaataa atggcgacaa ccaaagtatt gatatttcaa  12540
aaccaacaag gctggggacc aggactcaaa gtgaagcaga ttatgatttg gcaataaatt  12600
ctttaagatt aatatcagca gcttataaag gcattggaca taaattaaaa gaaggtgaga  12660
cctacttgtc acgtgacatg cagttcatga gtaaaacaat acaacatgaa ggggtctact  12720
acccggcctc catcaagaaa atattaagag ttggtccctg gatcaacaca atattagatg  12780
atataaaaac ttcaacagaa agtattggtt ctctaactca agaactagaa tataaaggtg  12840
aaagtttaat gagcagcctg ctgctgagga acttctggct ctacagatta tattcagtgg  12900
atttaaaaga tcattctttg tgtggaaagc agctctacag atccttaata aaagtgttaa  12960
aacatttgaa gaggtgcttc aacctggaga accttgggga atgtttggaa ttatttttaa  13020
atgtgcccat gcagtttgga ggtgctgacc caaatgtcat ctacaggagc ttctacagaa  13080
gaactccaga ttttctaaca gaaagtataa ctcatctcat cctcatttta aaacatttta  13140
gaagagattt ggaattcaac aaagataatg tctccaaagc tgttctttct ttgctagagt  13200
tcaccaagaa tgattctgca gaatttgtaa ctttgatgag agatcctcaa gcaattggta  13260
gtgagaggca ggccaagatc acttcagaca tcaacagaac agctgtaact tcagtgttat  13320
caaatgctcc aaatgaaata tttagaactt cagctcttca ttacagcagc acagaaaatg  13380
aattaaatgg aatagcaagt ggagtttctc ctgtttatcc tcatggtctt cgagttttat  13440
atgaaagttt accttttat aaagcagaga agattgtcaa catggtttct gggaccaagt  13500
ccatcaccaa catactggag aagacatcag ccatctccta cacagatata attcgagcca  13560
ccaacatgat ggtggagaac ctcactttgc taacaagaat aatgaaacca ggtgctgaca  13620
catctttgga tcctgacaca atagtaataa caatattatc aaaaataata agagataaat  13680
cctgggatgt tggtgatata attggtgtca cttccccatc tcctgtctcc tgcttcaagg  13740
tggtctacac atcaactcta caaaataatt cagtagtaat agaaagatac acaacagaca  13800
cctacacaag aggtaagaga ggccccacca agccctgggt gggcagcagc acacaggaga  13860
agaagtccat gcctgtctac aacagacaag ttttaacaag aggacaaaga gatcaaatag  13920
aaaatatagc aaagctggag tgggtgtttt cttcagtagc aaatattgat tctttgctaa  13980
atgagctcag caccatgact ttgggtcttt ctctaaggaa atgtagacaa ctttttccaa  14040
catatttaag tttaaacttc ctgcacaggc tttctgtcag cagcaggccc agagaatatc  14100
cttcttctct tcctgcctac aggacaacaa attttcattt tgatactgga ccaataaata  14160
aagtgttaac agaaagattt ggagatgaag atataaattt ggtatttcaa aatgcaatat  14220
catatggtct ttccaccatg tctttggtgg agcagtttac tggtgtctgt ccaaataaag  14280
ttttgctggt gcccaagcta caagaaatac aactaatgaa agttccaata tttcaaggtg  14340
gcttcaacct acaaagtata attccaataa taaggcagca gcacatgttc ctgcccaacc  14400
acatcactcc agcccagtat attgaattat ttctttcttc aaaacaattt cattcaagaa  14460
taaatttaaa acacaacaac agatttaaac ttgttttaca aaaagattat tttaatgggg  14520
```

-continued

```
agaacatgat agaaactttg tccacctgtt tggcaggcca ctggatcatc attttgatgc  14580
taatgaagga gagtcagggg atatttgaca aggagtggta tgatggtttt gtaacagacc  14640
acatgttcct ggacctgcag ctcttcctct cctccttcaa gacatttcta actgtcttca  14700
actttgctta tttaaaagtt ggttcaaata tagaagaaat aacaggaaat caagccaacc  14760
tgctggagct gctggacctg ggctactgga agaacatgta taaagtattt tcagagacca  14820
aggtgcggct ggctttgcta aaacaagatt tatcatttaa ttctgtgaag aacagcagca  14880
gcttccggca ctggtttata aattctctac aagaagtaca atgtacttct gtgccttggg  14940
tggtaaatgt aacaagaaat ccaactcatt taaaaggtgt tctacagtac atgaagatga  15000
tagaaagtgg catgattcaa ggttattcag caaatatttc ttcagtttta agtatcccat  15060
ataattatcc agacatggcg cacatgatga caaaaaataat aagaaatcga ggccacatgt  15120
cctatgatta tccaaagatg aagaaaagtt taactttctc catgacagac atgagtgaca  15180
gctacatgct caacctcttc cccaaagtag aatgttctta catgagtggt tatttggata  15240
aactagatga tactctacaa cttctaaaga aacctcctgt tggaagaaaa gttccttctg  15300
tggctttgcc ctggcaccac tgcaacagat acaactttgt cttcagcagc acaggctgca  15360
aagtttctgt cattgacatg cttccaaaac atttccgaag aagtaattta aaagtaatat  15420
gttttattgg agaaggggcg ggcaacctca tgctaagagc tgttttggaa gttggtggaa  15480
atataaaatt aatatataga tccttaaaag atcctgatga tcatcatgtt cctgtagaat  15540
ttctaagatt aaaaccttgt tatccttata ttgatactgg tggcagttta tctttggctt  15600
caacagatgc caccaacaag gcccactggg attatttaca tcttcactgg acagatcctt  15660
taaatttaat agtatgtgat gcagaaataa gtggtgtgaa gcactggcta aaaattcttc  15720
acaggtggta tgagcacatg acttcctgca agcactgttt aaaatcagaa catgataaat  15780
atttaataat aaaatatcat gctcaagatg atttaataga tcttcctcat ggtgtcaggc  15840
tactaaaatg taacatctgc ctgggctcca aactaagtgg cagtgagagc tacctgctca  15900
ttggtcttgg tctttcaaat aaacttcctg tctacagtga agttcttcat tcaaaacttc  15960
ttttggcaga atgtcatcag tttcatcatc caaaatattt ggatgtttct ggaataaata  16020
caaatataaa atccttaata ccaatgttgg attatccaat aacttacaac aagatcacca  16080
ctttgctaga aagtgtgcgg gagctttctt caaataaaaa caagaacacc atgtggattg  16140
gaagaaatcc tgtctaccat aataaatggc taaagaggaa atatttcaac attttaaaat  16200
ggctaaaata ctgtatagaa cttcctgcct tcaggatgga ttataattca tttgagagaa  16260
tagaaatgct ttatccaaat ttaagagatt tggtagattc tgtttctact tcagagctga  16320
agaaagtaat aaaagtaaca ggcatcctct tcaggagcaa caccatgtga attaatatgc  16380
caatgctaac atgtcatccc cactactttt tttgttcaat cactctcagt ctagacatgt  16440
gagaagatcc caaacccaac tgcacccctc ccactcgaaa tcagttgtag cctcagcagc  16500
tccatctgcc atgatctctg accagcagca aatgtattat tattttaatt tgtctatagt  16560
taacaaaaaa ttgatatctc acaggttgta aacatagttc ttttataatt attgttagtt  16620
aaactattgt gtttgacttc ctttgggtat tttttcccg t                       16661
```

<210> SEQ ID NO 63
<211> LENGTH: 9
<212> TYPE: DNA
<213> ORGANISM: Pneumonia virus of mice

<400> SEQUENCE: 63 gccgccacc 9

<210> SEQ ID NO 64
<211> LENGTH: 10
<212> TYPE: PRT
<213> ORGANISM: Pneumonia virus of mice

<400> SEQUENCE: 64

Thr Asn Phe Asp Arg Ser Asp Leu Glu Thr
1 5 10

<210> SEQ ID NO 65
<211> LENGTH: 10
<212> TYPE: PRT
<213> ORGANISM: Pneumonia virus of mice

<400> SEQUENCE: 65

Ser Asp Ser Glu Glu Ser Gly Asp Glu Ala
1 5 10

<210> SEQ ID NO 66
<211> LENGTH: 14
<212> TYPE: DNA
<213> ORGANISM: Pneumonia virus of mice

<400> SEQUENCE: 66
aagattgcta gtcc 14

<210> SEQ ID NO 67
<211> LENGTH: 17
<212> TYPE: DNA
<213> ORGANISM: Pneumonia virus of mice

<400> SEQUENCE: 67
caaagaccag aatcatg 17

<210> SEQ ID NO 68
<211> LENGTH: 6
<212> TYPE: DNA
<213> ORGANISM: Pneumonia virus of mice

<400> SEQUENCE: 68 tgagct 6

<210> SEQ ID NO 69
<211> LENGTH: 6
<212> TYPE: DNA
<213> ORGANISM: Pneumonia virus of mice

<400> SEQUENCE: 69 gatcca 6

<210> SEQ ID NO 70
<211> LENGTH: 10
<212> TYPE: DNA
<213> ORGANISM: Pneumonia virus of mice

<400> SEQUENCE: 70
cacatcctag 10

<210> SEQ ID NO 71
<211> LENGTH: 6
<212> TYPE: DNA

-continued

```
<213> ORGANISM: Pneumonia virus of mice

<400> SEQUENCE: 71

ccacct                                                          6


<210> SEQ ID NO 72
<211> LENGTH: 9
<212> TYPE: DNA
<213> ORGANISM: Pneumonia virus of mice

<400> SEQUENCE: 72

tagttatag                                                       9


<210> SEQ ID NO 73
<211> LENGTH: 3
<212> TYPE: DNA
<213> ORGANISM: Pneumonia virus of mice

<400> SEQUENCE: 73

tgg                                                             3
```

CHIMERIC VECTORS

CROSS-REFERENCE TO RELATED APPLICATIONS

This patent application is the U.S. national phase of International Patent Application No. PCT/US2019/028771, filed Apr. 23, 2019, which claims the benefit of U.S. Provisional Patent Application No. 62/661,320, filed Apr. 23, 2018, both of which are hereby incorporated by reference in their entireties.

STATEMENT REGARDING FEDERALLY SPONSORED RESEARCH AND DEVELOPMENT

This invention was made with Government support under project number 1ZIA000372-33 by the National Institutes of Health, National Institute Allergy and Infectious Diseases. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 153,486 Byte ASCII (Text) file named "750801_ST25.txt." created on Oct. 8. 2020.

BACKGROUND OF THE INVENTION

Human pathogens are a significant health concern. Despite continuous research, improved ways of preventing and treating pathogen infections are needed, especially from viruses such as human respiratory syncytial virus ("RSV").

BRIEF SUMMARY OF THE INVENTION

An embodiment of the invention provides live, chimeric non-human Mononegavirales vector which allows a cell to express at least one protein from at least one human pathogen.

Another embodiment of the invention provides compositions comprising the vectors of the invention and pharmaceutically acceptable carriers.

Another embodiment of the invention provides methods of eliciting an immune response to at least one human pathogen comprising administering a non-human Mononegavirales vector of the invention, or a composition of the invention, to a human.

Another embodiment of the invention provides methods of making live, chimeric non-human Mononegavirales vectors which allow a cell to express at least one protein from at least one human pathogen, comprising (a) inserting a non-native gene that encodes at least one protein from at least one human pathogen in a non-human Mononegavirales vector.

Another embodiment of the invention provides kits for eliciting an immune response, the kit comprising (a) the composition of the invention, and (b) at least one container for holding the composition.

Unexpectedly, the murine pneumonia virus (MPV) genome, as discussed herein, is an ideal vector for providing host protection against non-MPV viruses having several advantages over other types of vectors.

One advantage of the MPV genome is that it is relatively small (<15 kb) and can be easily manipulated by reverse genetics. Specifically, changes can be introduced into a cloned cDNA of the viral genome by standard recombinant DNA methods, and the resulting modified virus can be recovered in transfected tissue culture cells. In particular, one or more supernumerary genes expressing one or more heterologous antigens, such as a protective antigen from a heterologous pathogen, can be introduced into the MPV genome.

Another unexpected advantage of the MPV genome is that non-native inserts in the MPV genome are relatively stable during replication in vitro and in vivo. For example, a MPV vector with the RSV F protein inserted is very stable and despite continued investigation, deletion of the F protein sequence from the MPV genome has not yet been observed by the inventors. This is unexpected because typically the inserted sequence in some types of vector can be deleted after a few (or several) replications. Further, inserted sequences in vectors usually accumulate point mutations during replication that silence its expression; however, this occurs only sporadically in the MPV genome.

Further, several features of MPV biology make it safe to use as a vector (especially in humans). For example, MPV is a pneumotropic virus that replicates in the superficial epithelial cells of the respiratory mucosa, and thus is not a highly invasive or a systemic virus. In addition, MPV is a cytoplasmic RNA virus, and does not integrate into or otherwise perturb the host genome. Infection is acute with no known long term infection. Further, this type of virus (nonsegmented negative strand RNA virus) has very low incidence of recombination between viral genomes (Spann et al., J. Virol., 77: 11201-11211 (2003) (incorporated herein in its entirety by reference)).

In addition, MPV is likely naturally attenuated in humans by host range restriction, as it is in non-human primates. Rodents are the natural hosts of MPV, and the virus is highly attenuated in non-human primates, and therefore presumably in humans, due to host-range restriction. Attenuation of a paramyxovirus or pneumovirus by host range restriction is thought to be polygenic and stable, as illustrated by the host-range restriction of bovine parainfluenza virus type 3 in non-human primates and humans (Skiadopoulos, et al., J. Virol., 77:1141-1148 (2003) (incorporated herein in its entirety by reference)).

Further, there is no evidence of human infection by MPV, and humans lack acquired immunity against this virus (Brock, et al., J. Virol., 86: 5829-5843 (2012) (incorporated herein in its entirety by reference)). Despite 10-60% amino acid sequence identity between the proteins of MPV and RSV (the latter being the human pathogen that is the most closely-related to MPV), RSV-specific immunity does not cross-neutralize or cross-protect against MPV (tested in a mouse model). Thus, it is expected that use of the MPV-based vector of an embodiment of the invention in humans should not be subject to restriction by existing immunity, in particular immunity against RSV.

A further advantage is that MPV replicates in the respiratory mucosa and induces local immunity in the respiratory tract as well as systemic immunity. Accordingly, an MPV vector portends to be particularly effective against respiratory pathogens.

BRIEF DESCRIPTION OF THE SEVERAL VIEWS OF THE DRAWING(S)

FIG. 1 depicts a diagram showing rMPV antigenomes containing the RSV F gene added as a supernumerary gene in the first (F1), third (F3), or fourth (F4) gene position. The MPV genes are shown as unfilled rectangles and the RSV F gene is shown as a shaded rectangle. The MPV gene-start ("GS") and gene-end ("GE") transcription signals are indicated by unfilled and filled bars, respectively, flanking each gene including the supernumerary RSV F gene. The nucleotide sequence flanking the RSV F ORF is shown under each gene map, with the following features identified: RSV F ORF (represented by a shaded box), GS and GE transcription signals (shown in bold), intergenic regions ("IG"), and the "Kozak" sequence (shown with double underlining, SEQ ID NO: 63) placed upstream of the RSV F ORF to promote efficient translation.

Figure 2:
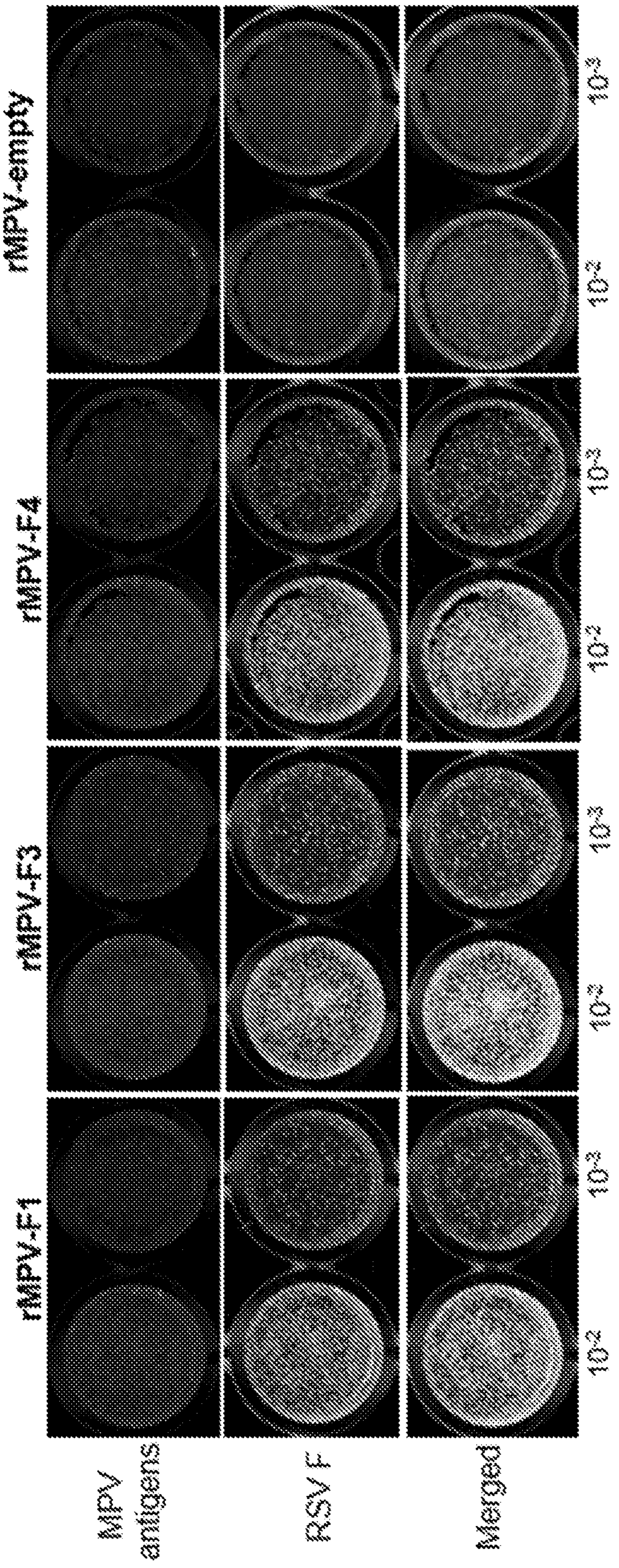

FIG. 2 depicts the results of a dual staining plaque assay which illustrates the stability of expression of RSV F by the rMPV vectors. Briefly, Vero cells were inoculated with serial dilutions of P1 virus stocks and incubated for four days under a 0.8% methylcellulose overlay. Monolayers were fixed and probed for RSV F and MPV antigens using specific antibodies followed by the corresponding infra-red dye-conjugated secondary antibodies. RSV F and MPV antigens appear green and red, respectively, and appear yellow when merged. One image was selected which represents the results from four independent experiments. In the upper row of plates labeled "MPV antigens," the grey scale is indicative of the color red. In the middle row of plates labeled "RSV F," the grey scale is indicative of the color green. In the bottom row of plates labeled "Merged," in the plates under columns "rMPV-F1," "rMPV-F4," and "rMPV-F3," the grey scale is indicative of the color yellow. In the bottom row of plates labeled "Merged," in the plates under column "rMPV-empty," the grey scale is indicative of the color red.

Figure 3:
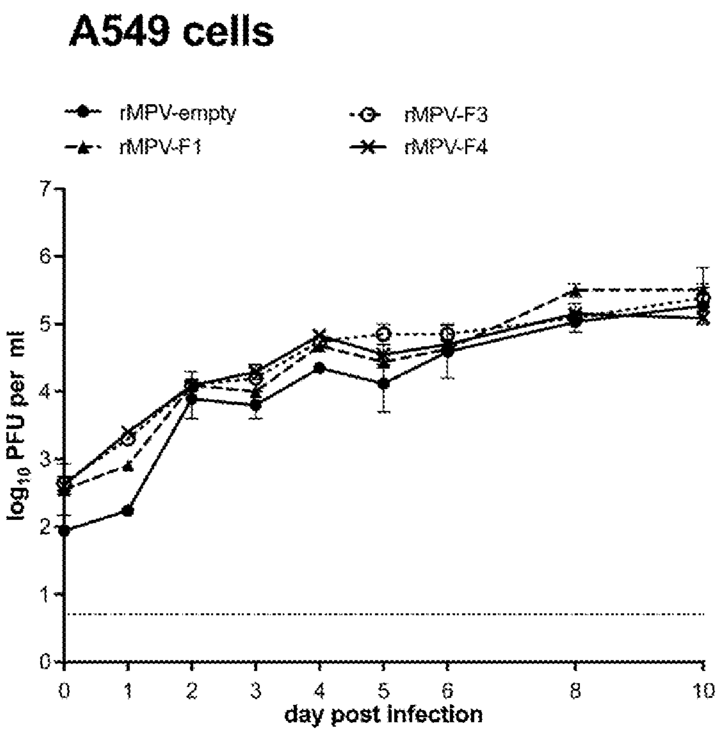

FIG. 3 depicts the multi-cycle growth kinetics of the rMPV—RSV-F vectors in human A549 lung epithelial cells. Replicate cultures of A549 cells were infected with a multiplicity of infection ("MOI") of 0.1 plaque forming units ("PFU," a measure of the number of infectious virus particles)/cell with rMPV-F1 (dashed line with triangles), rMPV-F3 (dotted line with open circles), rMPV-F4 (solid line with Xs), or rMPV-empty (solid line with solid black circles). At 24 hour intervals, two cultures per virus per cell line were harvested by scraping and vortexing, and clarified supernatants were prepared and flash frozen. The viral titers were subsequently determined in duplicate by plaque assay. The number of days post infection is on the x-axis and the $\log_{10}$ PFU per ml is on the y-axis. Data are shown as mean values with the standard error of the means, although in many cases the error bars are obscured by the symbols given the small margin of error. The limit of detection was 0.7 $\log_{10}$ PFU per mL (dotted line).

Figure 4:
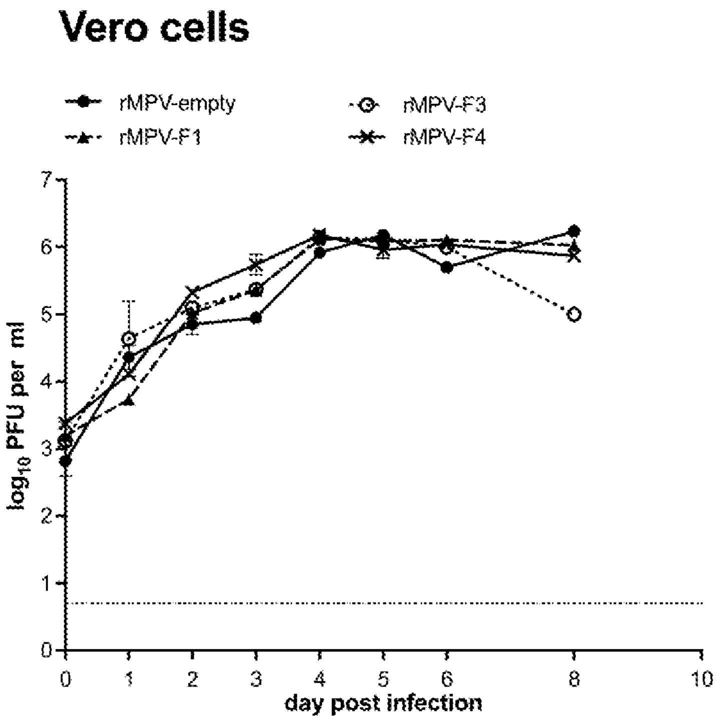

FIG. 4 depicts the multi-cycle growth kinetics of the rMPV-RSV-F vectors in Vero cells. Replicate cultures of Vero cells were infected with a MOI of 0.1 PFU/cell with rMPV-F1 (dashed line with triangles), rMPV-F3 (dotted line with open circles), rMPV-F4 (solid line with Xs), or rMPV-empty (solid line with solid black circles). At 24 hour intervals, two cultures per virus per cell line were harvested by scraping and vortexing, and clarified supernatants were prepared and flash frozen. Viral titers were subsequently determined in duplicate by plaque assay. The number of days post infection is on the x-axis and the $\log_{10}$ PFU per ml is on the y-axis. Data are shown as mean values with the standard error of the means, although in many cases the error bars are obscured by the symbols given the small margin of error. The limit of detection was 0.7 $\log_{10}$ PFU per mL (dotted line).

Figure 5:
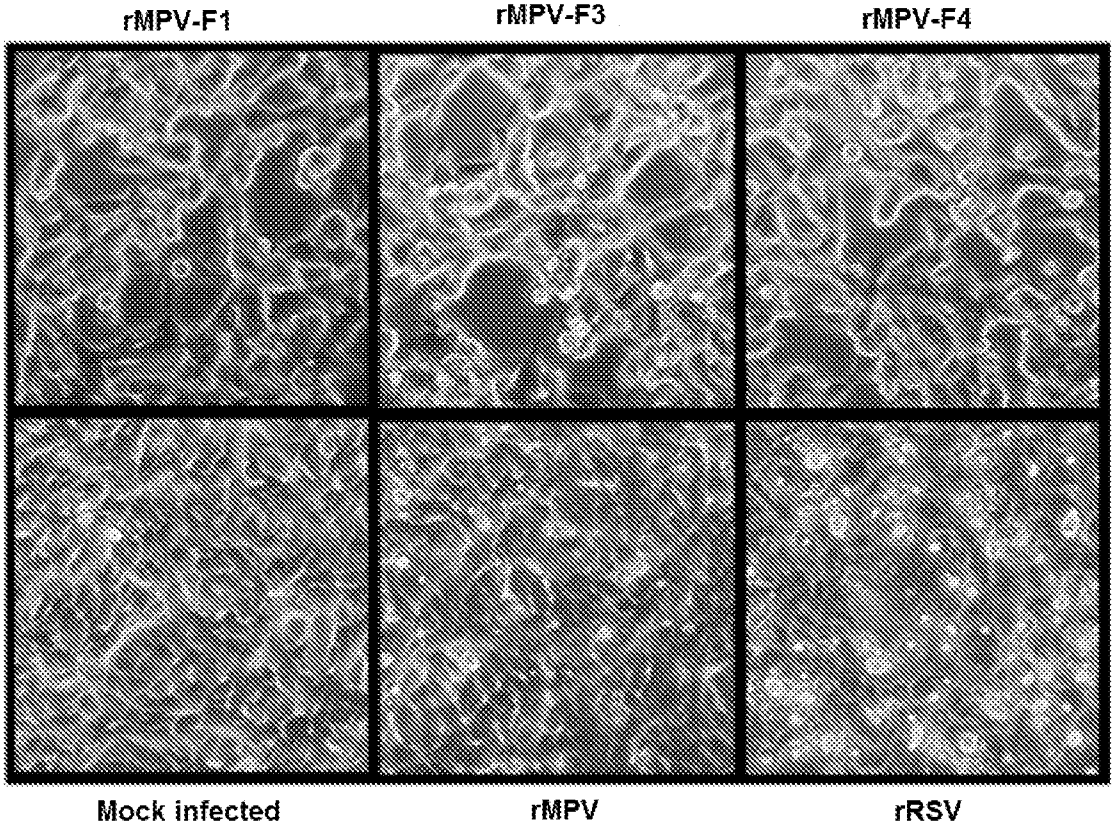

FIG. 5 depicts the cytopathic effects upon infection of Vero cells with rMPV—RSV-F vectors. Vero cell monolayers were infected with the indicated rMPV—RSV-F vectors, empty vector, or wt rRSV at an MOI of 10 PFU per cell, or mock-infected. The cultures were incubated for 96 hours at 32° C., and subjected to light photomicroscopy at a 200× magnification. The images shown are representative of two independent experiments. The mock infected and rMPV-empty infected cells do not show any signs of infection while the wt RSV, rMPV-F1, rMPV-F3, and rMPV-F4 infected cells show clear signs of viral infection.

Figure 6:
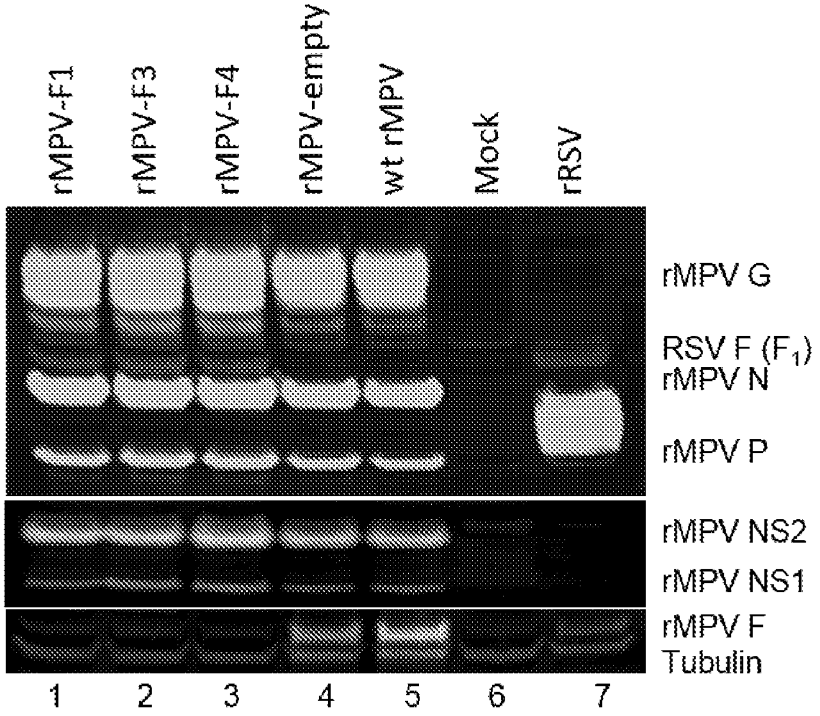

FIG. 6 depicts the results of a Western blot used to evaluate the expression of RSV F protein and rMPV proteins in infected cells. Cell lysates were prepared at 96 hours after inoculation ("hpi") using infected cells from the experiment shown in FIG. 5. The denatured and reduced lysates were subjected to Western blot analysis. As seen in FIG. 6, rMPV-F1, rMPV-F3, and rMPV-F4 (lanes 1, 2, and 3) all contained RSV F protein (while the rMPV-empty [lane 4] and wt rMPV [lane 5] did not).

Figure 7:
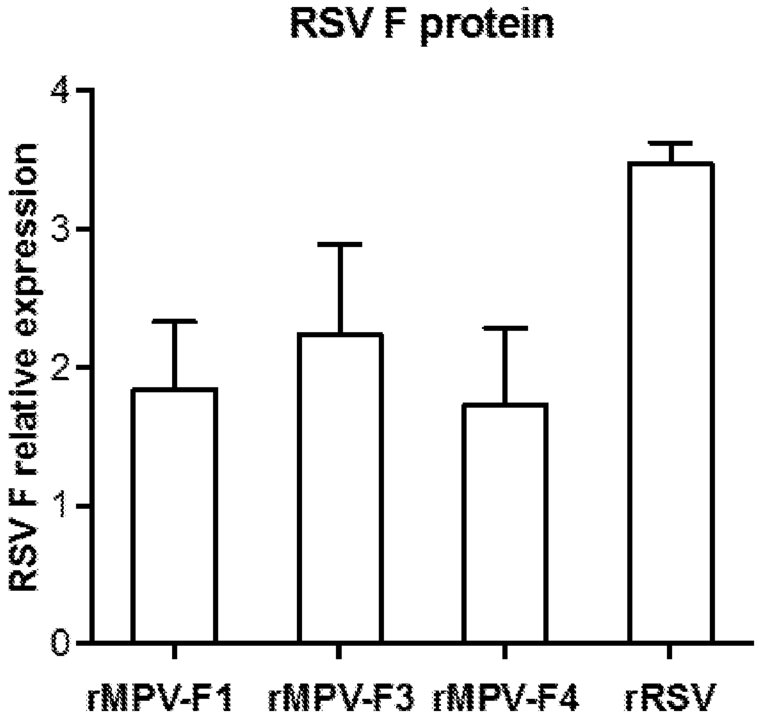

FIG. 7 depicts the level of RSV F protein expression in infected cells. RSV F protein was detected with a mouse monoclonal antibody. The quantification plots of protein bands are from the Western blot analysis shown in FIG. 6 and are representative of three independent experiments. The relative RSV F protein expression is on the y-axis and the vectors are listed on the x-axis. The standard error is shown. As seen in FIG. 7, rMPV-F1, rMPV-F3, rMPV-F4, and wt rRSV all expressed high levels of RSV F protein.

Figure 8:
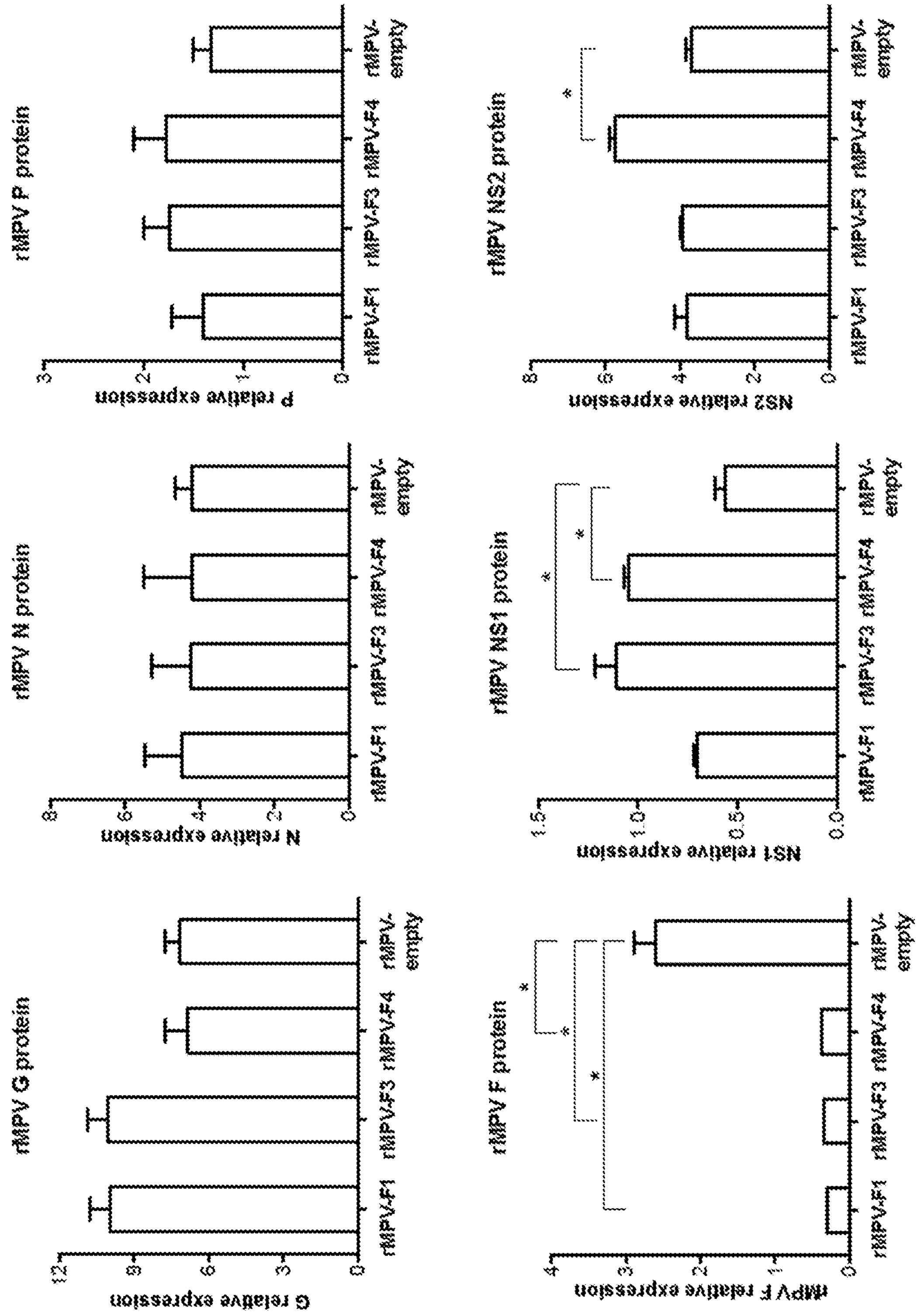

FIG. 8 depicts the level of rMPV G, N, P, F, NS1, and NS2 protein expression in infected cells. The MPV G, N, and P proteins were detected with a hyperimmune serum raised against sucrose-gradient-purified rMPV virions. The MPV F protein was detected with a rabbit polyclonal antiserum raised against a recombinant vaccinia virus expressing only the MPV F protein. The MPV NS1 and NS2 proteins were detected with individual rabbit hyperimmune sera each raised against a synthetic peptide derived from the respective protein. Tubulin was probed as a loading control and used to normalize each sample. The quantification plots of protein bands are from the same experiment shown in FIG. 5 and are representative of three independent experiments. The relative expression of each protein is on the y-axis and the vectors are listed on the x-axis. The standard error is shown. The asterisks indicate statistical significance (p values less than 0.05). As seen in FIG. 8, the infected cells expressed each tested protein.

DETAILED DESCRIPTION OF THE INVENTION

An embodiment of the invention provides live, chimeric non-human Mononegavirales vectors which allow a cell to express at least one protein from at least one human pathogen.

Vectors

As used herein, a "chimeric" vector is a vector comprising non-native genetic information. For example, a non-human Mononegavirales vector which comprises genetic information or material from a human pathogen (e.g., a rodent vector which comprises genetic information or material from a human pathogen or a MPV vector which comprises genetic information from RSV).

As used herein, a "non-human Mononegavirales vector" is a virus of the order Mononegavirales whose natural host is not a human.

The vectors described herein are attenuated when provided to a human. The attenuated vectors are capable of replication in vivo but have low or no virulence in the human host. The vector attenuation may be due to any of a variety of factors that may reduce the replication and/or virulence of the vector, including, but not limited to, infection of a non-natural host (host range restriction), the presence of one or more amino acid and/or nucleotide substitutions, the addition of a heterologous gene, or the removal of part or all of a vector gene. For example, a MPV vector is attenuated in human due in part to host range restriction.

Non-Human Mononegavirales Vectors

The non-human Mononegavirales vectors of the invention can be from any member of the order Mononegavirales as long as the natural host of the virus is a non-human animal. In an embodiment, the natural host of the virus is non-human animal. Preferably, the natural host of the virus is a non-human mammal. Preferably, the natural host of the virus is in the order Rodentia. Preferably, the natural host of the virus is in the family Muridae. Preferably, the natural host of the virus is in the subfamily Murinae. Preferably, the natural host of the virus is a mouse.

A virus is a member of the order Mononegavirales if: its genome is a linear, typically nonsegmented, single-stranded, non-infectious RNA of negative polarity that is tightly encapsidated in a ribonucleocapsid both in the infected cell and the virion; possesses inverse-complementary 3' and 5' termini; is not covalently linked to a protein; its genome has the characteristic gene order 3'-UTR-core protein genes-envelope protein genes-RNA-dependent RNA polymerase gene-5'-UTR (3'-N-P-M-G-L-5'); it produces 5-10 distinct mRNAs from its genome via polar sequential transcription from a single promoter located at the 3' end of the genome; mRNAs are 5' capped and polyadenylated; it replicates by synthesizing complete positive-sense copies of the genome, called antigenomes; it forms infectious helical ribonucleocapsids as the templates for the synthesis of mRNAs, antigenomes, and genomes; it encodes an RNA-dependent RNA polymerase (RdRp, L); and/or it typically produces enveloped virions.

The non-human Mononegavirales vectors can be from the families Pneumoviridae, Bornaviridae, Filoviridae, Paramyxovirdae, Rhabdoviridae, and those which are currently unassigned to a family.

In an embodiment, the non-human Mononegavirales vectors are from the family Pneumoviridae. The non-human Mononegavirales vectors from the family Pneumoviridae can include those from the genus Metapneumovirus, for example the species Avian metapneumovirus. The species Avian metapneumovirus includes avian metapneumovirus ("AMPV").

The non-human Mononegavirales vectors from the family Pneumoviridae can also include those from the genus Orthopneumovirus, for example the species Bovine orthopneumovirus and Murine orthopneumovirus. The species Bovine orthopneumovirus includes bovine respiratory syncytial virus ("BRSV"). The species Murine orthopneumovirus includes murine pneumonia virus ("MPV," previously called pneumonia virus of mice, PVM). Preferably, the non-human vector of an embodiment of the invention is MPV.

The non-human Mononegavirales vectors from the family Bornaviridae can include those from the genus Bornavirus, for example, the following species: Elapid 1 bonavirus, Mammalian 1 bonavirus, Mammalian 2 bonavirus, Passeriform 1 bonavirus, Passeriform 2 bonavirus, Psittaciform 1 bornavirus, Psittaciform 2 bornavirus, and Waterbird 1 bornavirus.

The non-human Mononegavirales vectors from the family Filoviridae can include the species Lloviu cuevavirus, from the genus Cuevairus.

The non-human Mononegavirales vectors from the family Paramyxoviridae can include those from the genus Avulavirus, for example Avian Avulavirus 1-Avian Avulavirus 13; those from the genus Henipavirus, for example the species Cedar henipavirus, Ghanaian bat henipavirus, Hendra henipavirus, Mojiang henipavirus, and Nipah heniparus (e.g., Nipah virus); those from the genus Morbillivirus; those from the genus Rubulavirus, for example the species Achimoto rubulavirus 1, Achimoto rubulavirus 2, Bat mumps rubulavirus, Canine rubulavirus, Mapuera rubulavirus, Menangly rubulavirus, Porcine rubulavirus, Simian rubulavirus, Sosuga rubulavirus, Teviot rubulavirus, Tioman rubulavirus, Tuhoko rubulavirus 1, Tuhoko rubulavirus 2, Tuhoko rubulavirus 3, and parainfluenza 5.

The non-human Mononegavirales vectors from the family Rhabdoviridae can include those from the genus Ephemerovirus, for example Bovine fever ephemerovirus; those from the genus Hapavirus; those from the genus Ledantevirus; and those from the genus Lyssavirus, for example, European bat 1 lyssavirus, European bat 2 lyssavirus, Lagos bat lyssavirus, Rabies lyssavirus, Shimoni bat lyssavirus, and West Caucasian bat lyssavirus.

In addition, the vectors of the invention can be from viruses of the order Mononegavirales that are currently unknown to one of skill in the art (i.e., those that are naturally occurring but have yet to be discovered, or those that are yet to be created either through natural or artificial processes).

In an embodiment, the non-human Mononegavirales vector is the paramyxovirus Sendai virus, and the human pathogen is not Ebola virus or respiratory syncytial virus. In an embodiment, the human pathogen is Ebola virus or respiratory syncytial virus and the non-human Mononegavirales vector is not paramyxovirus Sendai virus.

In an embodiment, the non-human Mononegavirales vector is paramyxovirus parainfluenza virus 5, and the human pathogen is not RSV, influenza, or rabies. In an embodiment, the human pathogen is RSV, influenza, or rabies, and the non-human Mononegavirales vector is not paramyxovirus parainfluenza virus 5.

In an embodiment, the non-human Mononegavirales vector is rhabdovirus vesicular stomatitis virus ("VSV"), and the human pathogen is not Ebola virus or Marburg virus. In an embodiment, the human pathogen is Ebola virus or Marburg virus, and the non-human Mononegavirales vector is not paramyxovirus rhabdovirus vesicular stomatitis virus.

In an embodiment, the non-human Mononegavirales vector is Newcastle disease virus, and the human pathogen is not influenza virus. In an embodiment, the human pathogen is influenza virus, and the non-human Mononegavirales vector is not Newcastle disease virus.

In an embodiment, the non-human Mononegavirales vector is from the family Pneumoviridae. Preferably, the non-human Mononegavirales vector is from the genus Murine orthopneumovirus. Preferably, the non-human Mononegavirales vector is MPV.

Preferably, the non-human Mononegavirales vector is a vector that infects the respiratory tract. Preferably, the non-human Mononegavirales vector is from the family Pneumoviridae and infects the respiratory tract.

In an embodiment, the non-human Mononegavirales vector is derived from wild type MPV (GenBank accession #AY729016). In an embodiment, mutations can be introduced in the MPV encoding sequence of the reverse genetic system to generate unique restriction enzyme sites for cloning (see Krempl, et al., J. Virol., 81(17): 9490-501 (2007) (incorporated herein in its entirety by reference)). In an embodiment, the restriction enzyme sites can include AgeI and BstBI at the genome nucleotide positions 4509 and 8461, respectively. In an embodiment, the L polymerase ORF can be partly modified by codon pair optimization with a goal to increase the expression of L protein.

In an embodiment, the MPV vector has a genome promoter with at least 85% (i.e., 86%, 87%, 88%, 89%, 90%, 91%, 92%, 93%, 94%, 95%, 96%, 97%, 98%, 99%, or 100%) identity to ACGCGAAAAAATGCATAACAAAACTATCAACCTGAAAAAAGTT (SEQ ID NO: 1).

In an embodiment, the MPV vector has an antigenome promoter with at least 85% (i.e., 86%, 87%, 88%, 89%, 90%, 91%, 92%, 93%, 94%, 95%, 96%, 97%, 98%, 99%, or 100%) identity to (SEQ ID NO: 2)
TTGATATCTCACAGGTTGTAAACATAGTTCTTTTATAATTATTGTTAGTTA

AACTATTGTGTTTGACTTCCTTTGGGTATTTTTTTCCCGT.

In an embodiment, the intergenic region between the SH and G genes and that between the M2 and L genes can be modified by introducing unique restriction enzyme sites (e.g., AgeI and BstBI), as indicated above, to create the reverse genetic system and the modified sequences are shown for these regions as shown in Table 1 below.

TABLE 1

MPV transcription signals

| Gene | Gene start | Gene end | Intergenic |
|---|---|---|---|
| NS1 | AGGACAAGTG (SEQ ID NO: 3) | TAGTTAATTAAAA (SEQ ID NO: 4) | CAAAGGGT (SEQ ID NO: 5) |
| NS2 | AGGACAAGTC (SEQ ID NO: 6) | TAGTTATAGAAAAA (SEQ ID NO: 7) | CATT (SEQ ID NO: 8) |
| N | AGGATAAATA (SEQ ID NO: 9) | TATTTAATTAAAA (SEQ ID NO: 10) | CTGGAAAATGT (SEQ ID NO: 11) |
| P | AGGATAAATA (SEQ ID NO: 12) | TAGTTAATTAAAA (SEQ ID NO: 13) | TAACAAC (SEQ ID NO: 14) |
| M | AGGACAAATA (SEQ ID NO: 15) | TAGTTAAATAAAA (SEQ ID NO: 16) | TC (SEQ ID NO: 17) |
| SH | AGGATAAATA (SEQ ID NO: 18) | TAGTTAACAAAAAA (SEQ ID NO: 19) | CCGGT (SEQ ID NO: 20) |
| G | AGGATAAGTACTATC (SEQ ID NO: 21) | TAGTTAATGAAAA (SEQ ID NO: 22) | CTAAGCTTTGATATA AT (SEQ ID NO: 23) |
| F | AGGACAAATA (SEQ ID NO: 24) | TAGTTAATTAAAAA (SEQ ID NO: 25) | CTT (SEQ ID NO: 26) |
| M2 | AGGATAAGTGA (SEQ ID NO: 27) | TAGTTATATAAAAA AA (SEQ ID NO: 28) | TATTCGAATT (SEQ ID NO: 29) |
| L | AGGATCAATA (SEQ ID NO: 30) | TAGTTAACAAAAAA (SEQ ID NO: 31) | N/A |

In an embodiment, the MPV vector has transcription signal with at least 95% (i.e., 96%, 97%, 98%, 99%, or 100%) identity to SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, and/or SEQ ID NO: 31.

In an embodiment, the MPV vector comprises nucleotide sequences which encode for (listed in 3' to 5' gene order): non-structural protein 1 ("NS1"), non-structural protein 2 ("NS2"), nucleoprotein ("N protein"), phosphoprotein ("P protein"), matrix protein ("M protein"), small hydrophobic protein ("SH protein"), attachment protein (G protein), fusion protein (F protein), M2-1 and M2-2 proteins, and polymerase protein ("L protein").

In an embodiment, the MPV vector has sequence for NS1 (e.g., GenBank accession #AY729016) with at least 85% (i.e., 86%, 87%, 88%, 89%, 90%, 91%, 92%, 93%, 94%, 95%, 96%, 97%, 98%, 99%, or 100%) identity to SEQ ID NO: 32.

In an embodiment, the MPV vector allows a cell to produce protein NS1 with at least 85% (i.e., 86%, 87%, 88%, 89%, 90%, 91%, 92%, 93%, 94%, 95%, 96%, 97%, 98%, 99%, or 100%) identity to SEQ ID NO: 33.

In an embodiment, the MPV vector has sequence for NS2 (e.g., GenBank accession #AY729016) with at least 85% (i.e., 86%, 87%, 88%, 89%, 90%, 91%, 92%, 93%, 94%, 95%, 96%, 97%, 98%, 99%, or 100%) identity to SEQ ID NO: 34.

In an embodiment, the MPV vector allows a cell to produce protein NS2 with at least 85% (i.e., 86%, 87%, 88%, 89%, 90%, 91%, 92%, 93%, 94%, 95%, 96%, 97%, 98%, 99%, or 100%) identity to SEQ ID NO: 35.

In an embodiment, the MPV vector has sequence for N with at least 85% (i.e., 86%, 87%, 88%, 89%, 90%, 91%, 92%, 93%, 94%, 95%, 96%, 97%, 98%, 99%, or 100%) identity to SEQ ID NO: 36.

In an embodiment, the MPV vector allows a cell to produce protein N with at least 85% (i.e., 86%, 87%, 88%, 89%, 90%, 91%, 92%, 93%, 94%, 95%, 96%, 97%, 98%, 99%, or 100%) identity to SEQ ID NO: 37.

In an embodiment, the MPV vector has sequence for P with at least 85% (i.e., 86%, 87%, 88%, 89%, 90%, 91%, 92%, 93%, 94%, 95%, 96%, 97%, 98%, 99%, or 100%) identity to SEQ ID NO: 38.

In an embodiment, the MPV vector allows a cell to produce protein P with at least 85% (i.e., 86%, 87%, 88%, 89%, 90%, 91%, 92%, 93%, 94%, 95%, 96%, 97%, 98%, 99%, or 100%) identity to SEQ ID NO: 39.

In an embodiment, the MPV vector has sequence for M with at least 85% (i.e., 86%, 87%, 88%, 89%, 90%, 91%, 92%, 93%, 94%, 95%, 96%, 97%, 98%, 99%, or 100%) identity to SEQ ID NO: 40.

In an embodiment, the MPV vector allows a cell to produce protein M with at least 85% (i.e., 86%, 87%, 88%, 89%, 90%, 91%, 92%, 93%, 94%, 95%, 96%, 97%, 98%, 99%, or 100%) identity to SEQ ID NO: 41.

In an embodiment, the MPV vector has sequence for SH with at least 85% (i.e., 86%, 87%, 88%, 89%, 90%, 91%, 92%, 93%, 94%, 95%, 96%, 97%, 98%, 99%, or 100%) identity to SEQ ID NO: 42.

In an embodiment, the MPV vector allows a cell to produce protein SH with at least 85% (i.e., 86%, 87%, 88%, 89%, 90%, 91%, 92%, 93%, 94%, 95%, 96%, 97%, 98%, 99%, or 100%) identity to SEQ ID NO: 43.

In an embodiment, the MPV vector has sequence for G with at least 85% (i.e., 86%, 87%, 88%, 89%, 90%, 91%, 92%, 93%, 94%, 95%, 96%, 97%, 98%, 99%, or 100%) identity to SEQ ID NO: 44.

In an embodiment, the MPV vector allows a cell to produce protein G with at least 85% (i.e., 86%, 87%, 88%, 89%, 90%, 91%, 92%, 93%, 94%, 95%, 96%, 97%, 98%, 99%, or 100%) identity to SEQ ID NO: 45.

In an embodiment, the MPV vector has sequence for F with at least 85% (i.e., 86%, 87%, 88%, 89%, 90%, 91%, 92%, 93%, 94%, 95%, 96%, 97%, 98%, 99%, or 100%) identity to SEQ ID NO: 46.

In an embodiment, the MPV vector allows a cell to produce F protein with at least 85% (i.e., 86%, 87%, 88%, 89%, 90%, 91%, 92%, 93%, 94%, 95%, 96%, 97%, 98%, 99%, or 100%) identity to SEQ ID NO: 47.

In an embodiment, the MPV vector has sequence for M2-1 with at least 85% (i.e., 86%, 87%, 88%, 89%, 90%, 91%, 92%, 93%, 94%, 95%, 96%, 97%, 98%, 99%, or 100%) identity to SEQ ID NO: 48.

In an embodiment, the MPV vector allows a cell to produce protein M2-1 with at least 85% (i.e., 86%, 87%, 88%, 89%, 90%, 91%, 92%, 93%, 94%, 95%, 96%, 97%, 98%, 99%, or 100%) identity to SEQ ID NO: 49.

In an embodiment, the MPV vector has sequence for M2-2 with at least 85% (i.e., 86%, 87%, 88%, 89%, 90%, 91%, 92%, 93%, 94%, 95%, 96%, 97%, 98%, 99%, or 100%) identity to SEQ ID NO: 50.

In an embodiment, the MPV vector allows a cell to produce protein M2-2 with at least 85% (i.e., 86%, 87%, 88%, 89%, 90%, 91%, 92%, 93%, 94%, 95%, 96%, 97%, 98%, 99%, or 100%) identity to SEQ ID NO: 51.

In an embodiment, the MPV vector has codon pair optimized sequence for L with at least 85% (i.e., 86%, 87%, 88%, 89%, 90%, 91%, 92%, 93%, 94%, 95%, 96%, 97%, 98%, 99%, or 100%) identity to SEQ ID NO: 52.

In an embodiment, the MPV vector allows a cell to produce protein L with at least 85% (i.e., 86%, 87%, 88%, 89%, 90%, 91%, 92%, 93%, 94%, 95%, 96%, 97%, 98%, 99%, or 100%) identity to SEQ ID NO: 53.

In some embodiment, the "Kozak" sequence (GCCGCCACC (SEQ ID NO: 63)) is upstream of the AUG start codon. The "Kozak" sequence can provide efficient context for translation initiation. Other sequences are known by one skilled in the art and can be used to increase translation efficiency.

Human Pathogens

The vectors of the present invention can express proteins from any human pathogen. As used herein, a "human pathogen" is a pathogen which can cause an infection in a human. Human pathogens can include viruses, bacteria, protozoa, prions, and fungi.

Pathogen bacteria include those from the following species: *Actinomyces israelii, Bacillus anthracis, Bacteroides fragilis, Bordetella pertussis, Borrelia, Brucella, Campylobacter jejuni, Chlamydia, Chlamydophila psittaci, Clostridium, Corynebacterium diphtheriae, Ehrlichia, Enterococcus, Escherichia, Francisella tularensis, Haemophilus influenzae, Helicobacter pylori, Klebsiella pneumoniae, Legionella pneumophila, Leptospira, Listeria monocytogenes, Mycobacterium, Mycoplasma pneumoniae, Neisseria, Pseudomonas aeruginosa, Nocardia asteroides, Rickettsia rickettsii, Salmonella, Shigella, Staphylococcus, Streptococcus, Treponema pallidum, Vibrio cholerae*, and *Yersinia pestis*

Pathogenic fungi include those from the following species: *Candida, Aspergillus, Cryptococcus, Histoplasma, Pneumocystis*, and Stachybotrys.

Pathogenic protozoa include those which cause the following illnesses: malaria (by *Plasmodium*), amoebiasis, giardiasis, toxoplasmosis, cryptosporidiosis, trichomoniasis, Chagas disease, leishmaniasis, African trypanosomiasis, amoebic dysentery, *acanthamoeba keratitis*, and primary amoebic meningoencephalitis (naegleriasis).

Pathogenic prions include those which cause the following illnesses: Creutzfeldt-Jakob disease, Iatrogenic Creutzfeldt-Jakob disease, Variant Creutzfeldt-Jakob disease, Familial Creutzfeldt-Jakob disease, Sporadic Creutzfeldt-Jakob disease, Gerstmann-Sträussler-Scheinker syndrome, Fatal familial insomnia, Kuru, Familial spongiform encephalopathy, and Multiple System Atrophy.

Pathogenic viruses include those from the following families (or orders): family Paramyxoviridae which include Human Parainfluenza Virus serotypes 1, 2, and 3 (HPIV1, 2, 3) and Measles virus; family Henipaviridae, which include Hendra virus and Nipah virus; family Orthomyxoviridae which include the avian influenza A viruses; family Coronaviridae, which include Severe Acute Respiratory Syndrome (SARS), Coronavirus and Middle East Respiratory Syndrome (MERS) Coronavirus; family Filoviridae which include Ebola virus and Marburg virus; family Arenaviridae which include Lassa Virus; order Bunyavirales (previously known as family Bunyaviridae), which include Crimean-Congo Hemorrhagic Fever Virus, Rift Valley Fever Virus, and Hantavirus; Flaviviridae and Togaviridae families, which include West Nile virus, Dengue virus, Zika virus, and Chikungunya virus; and Pneumoviridae, which include human respiratory syncytial virus (RSV) and human metapneumovirus.

Preferably, the human pathogen is a virus. Preferably, the human pathogen is a Pneumoviridae virus.

Preferably, the human pathogen is RSV. RSV is an enveloped, single stranded negative sense RNA virus. RSV possesses 10 genes that encode 11 proteins. The fusion F ("F protein") and the attachment G ("G protein") surface glycoproteins are the two viral neutralization antigens and are the major protective antigens. RSV F is a type I transmembrane envelope glycoprotein that mediates fusion of the virion envelope with the host cell membrane during entry.

Proteins from Human Pathogens

The at least one protein from at least one human pathogen, expressed by the cells infected by the vectors of the present invention, can include any protein which would allow the host to develop an immune response to the human pathogen.

In an embodiment, the protein is the Fusion (F) and Hemagglutinin (H) or Hemagglutinin-Neuraminidase (HN) proteins of family Paramyxoviridae, as exemplified by Human Parainfluenza Virus serotypes 1, 2, and 3 (HPIV1, 2, 3) and Measles virus.

In an embodiment, the protein is the Fusion (F) and attachment (G) proteins of family Henipaviridae, as exemplified by Hendra virus and Nipah virus.

In an embodiment, the protein is the Hemagglutinin (HA) and Neuraminidase (NA) proteins of family Orthomyxoviridae, as exemplified by highly pathogenic avian influenza A viruses.

In an embodiment, the protein is the Spike (S) protein of members of family Coronaviridae, as exemplified by Severe Acute Respiratory Syndrome (SARS), Coronavirus and Middle East Respiratory Syndrome (MERS) Coronavirus.

In an embodiment, the protein is the GP protein of members of family Filoviridae, as exemplified by Ebola virus and Marburg virus.

In an embodiment, the protein is the GP1 and GP2 proteins (expressed as a precursor GPC) of family Arenaviridae, as exemplified by Lassa Virus.

In an embodiment, the protein is the Gn (GP1) and Gc (GP2) proteins of members of Order Bunyavirales (previously known as family Bunyaviridae), as exemplified by Crimean-Congo Hemorrhagic Fever Virus, Rift Valley Fever Virus, and Hantavirus.

In an embodiment, the protein is the E glycoprotein species of members of the Flaviviridae and Togaviridae Families, as exemplified by West Nile virus, Dengue virus, Zika virus, and Chikungunya virus.

Preferably, the protein is the Fusion protein (F) or Glycoprotein (G) of family Pneumoviridae, as exemplified by respiratory syncytial virus (RSV) and metapneumovirus (MPV).

Fusion Protein (F) of Family Pneumoviridae

There are two wild types of this protein (A and B, or A1 and B2) and many natural variants thereof. Further, the open reading frame of the nucleotide sequence can be modified by codon optimization to enhance expression of the protein. In addition, the nucleotide sequence can be modified to contain two HEK amino acid assignments (66E and 101P, see SEQ ID NO: 54) identical to those present in the wild type. Also the sequences can have mutations, deletions, and insertions as long as they do not significantly impact the ability of the expressed protein to elicit the desired immune response.

In an embodiment, the non-human Mononegavirales vector has sequence for F protein (from RSV A2) with at least 85% (i.e., 86%, 87%, 88%, 89%, 90%, 91%, 92%, 93%, 94%, 95%, 96%, 97%, 98%, 99%, or 100%) identity to SEQ ID NO: 54.

In an embodiment, the non-human Mononegavirales vector allows a cell to produce F protein (from RSV A2) with at least 85% (i.e., 86%, 87%, 88%, 89%, 90%, 91%, 92%, 93%, 94%, 95%, 96%, 97%, 98%, 99%, or 100%) identity to SEQ ID NO: 55.

In an embodiment, the non-human Mononegavirales vector has sequence for F protein (from RSV A2) with at least 85% (i.e., 86%, 87%, 88%, 89%, 90%, 91%, 92%, 93%, 94%, 95%, 96%, 97%, 98%, 99%, or 100%) identity to SEQ ID NO: 56.

In an embodiment, the non-human Mononegavirales vector allows a cell to produce F protein (from RSV A2) with at least 85% (i.e., 86%, 87%, 88%, 89%, 90%, 91%, 92%, 93%, 94%, 95%, 96%, 97%, 98%, 99%, or 100%) identity to SEQ ID NO: 57.

In an embodiment, the non-human Mononegavirales vector has sequence for F protein (from RSV B1) with at least 85% (i.e., 86%, 87%, 88%, 89%, 90%, 91%, 92%, 93%, 94%, 95%, 96%, 97%, 98%, 99%, or 100%) identity to SEQ ID NO: 58.

In an embodiment, the non-human Mononegavirales vector allows a cell to produce F protein (from RSV B1) with at least 85% (i.e., 86%, 87%, 88%, 89%, 90%, 91%, 92%, 93%, 94%, 95%, 96%, 97%, 98%, 99%, or 100%) identity to SEQ ID NO: 59.

Preferably, RSV F protein is maintained in its prefusion form which allows for an increased immune response as compared to its fusion form. RSV F protein can be stabilized in the prefusion form by introducing mutations which result in disulfide bond formation or cavity filling mutations in its globular head. Stabilized RSV F protein is less likely to unfold (which is especially desirable when it comes in contact with a host cell) (see Mclellan, et al., Science, 340: 1113-1117 (2013); Mclellan, et al., Science, 342: 592-598 (2013); and Joyce, et al., Nature Structural and Molecular Biology, doi:10.1038/nsmb.3267 (2016); each of which is incorporated herein in its entirety by reference).

In an embodiment, the non-human Mononegavirales vector is a MPV vector and allows the cell to express F protein (of family Pneumoviridae). The sequence encoding F protein can be in any suitable place in the MPV vector genome such that F protein is expressed and provided it does not disrupt a vector gene. For example, the sequence encoding F protein can be inserted as illustrated in FIG. 1. The sequence encoding F protein should be flanked by vector gene start and gene end sequences. There can be a few or up to 200 nucleotides on either side of the open reading frame. Preferably, there about 10-20 nucleotides before the sequence encoding F protein begins to allow for ribosomes to load up thereby have efficient expression of the protein.

In an embodiment, the non-human Mononegavirales vector is a MPV vector and allows a cell to express F protein (of family Pneumoviridae) and comprises a sequence with at least 85% (i.e., 86%, 87%, 88%, 89%, 90%, 91%, 92%, 93%, 94%, 95%, 96%, 97%, 98%, 99%, or 100%) identity to SEQ ID NO: 60 (rMPV-F1).

In an embodiment, the non-human Mononegavirales vector is a MPV vector and allows a cell to express F protein (of family Pneumoviridae) and comprises a sequence with at least 85% (i.e., 86%, 87%, 88%, 89%, 90%, 91%, 92%, 93%, 94%, 95%, 96%, 97%, 98%, 99%, or 100%) identity to SEQ ID NO: 61 (rMPV-F3).

In an embodiment, the non-human Mononegavirales vector is a MPV vector and allows a cell to express F protein (of family Pneumoviridae) and comprises a sequence with at least 85% (i.e., 86%, 87%, 88%, 89%, 90%, 91%, 92%, 93%, 94%, 95%, 96%, 97%, 98%, 99%, or 100%) identity to SEQ ID NO: 62 (rMPV-F4).

In an embodiment, the cell that expresses at least one protein from at least one human pathogen is a human cell.

Vector Compositions

An embodiment of the invention provides compositions comprising the vector of an embodiment of the invention and a pharmaceutically acceptable carrier.

The composition may be suitable for administration to a subject in need thereof. In an embodiment, the vector composition is suitable for administration to a mammal. In an embodiment, the vector is substantially free of either endotoxins or exotoxins. Endotoxins may include pyrogens, such as lipopolysaccharide ("LPS") molecules. The vector may also be substantially free of inactive protein fragments which may cause a fever or other side effects. In embodiments, the composition contains less than about 1%, less than about 0.1%, less than about 0.01%, less than about 0.001%, or less than about 0.0001% of endotoxins, exotoxins, and/or inactive protein fragments. In some embodiments, the vector composition has lower levels of pyrogens than industrial water, tap water, or distilled water. Other vector composition components may be purified using methods known in the art, such as ion-exchange chromatography, ultrafiltration, or distillation. In other embodiments, the pyrogens may be inactivated or destroyed prior to administration to a patient. Raw materials for vector composition, such as water, buffers, salts and other chemicals may also be screened and depyrogenated. All materials in the vector composition may be sterile, and each lot of the vector composition may be tested for sterility.

In embodiments, the vector composition comprises less than about 50%, less than about 20%, less than about 10%, or less than about 5% (by dry weight) contaminating protein. In embodiments, polysaccharide capsule protein is present in the substantial absence of other biological macromolecules, such as other proteins (particularly other proteins which may substantially mask, diminish, confuse or alter the characteristics of the component proteins either as purified preparations or in their function in the subject reconstituted mixture). In some embodiments, the vector composition comprising purified subunit proteins contains less than about 5%, less than about 2%, less than about 1%, less than about 0.5%, less than about 0.2%, less than about 0.1% of protein from host cells in which the subunit proteins were expressed, relative to the amount of purified subunit.

In some embodiments, the vector has low or no toxicity to the host. In certain embodiments, the vector composition comprises ingredients at concentrations that are less than $LD_{50}$ measurements for the animal being vaccinated. $LD_{50}$ measurements may be obtained in mice or other experimental model systems, and extrapolated to humans and other animals. Methods for estimating the $LD_{50}$ of compounds in humans and other animals are well-known in the art. A vector composition may contain any component within it, might have an $LD_{50}$ value in rats of greater than about 100 g/kg, greater than about 50 g/kg, greater than about 20 g/kg, greater than about 10 g/kg, greater than about 5 g/kg, greater than about 2 g/kg, greater than about 1 g/kg, greater than about 500 mg/kg, greater than about 200 mg/kg, greater than about 100 mg/kg, greater than about 50 mg/kg, greater than about 20 mg/kg, or greater than about 10 mg/kg.

The compositions suitable for introduction of the vector vary according to route of administration. Compositions suitable for intranasal administration, such as, for example, aerosol solutions (e.g., they can be "nebulized") and drop solutions, both of which can include sugar(s), suspending agent(s), solubilizer(s), thickening agent(s), stabilizer(s), salt buffer(s), and preservative(s).

In an embodiment, a composition comprising the vector of an embodiment of the invention comprises a monosaccharide and/or disaccharide sugar. In another embodiment, a composition comprising the vector of an embodiment of the invention comprises glucose, sucrose, and/or fructose as the sugar.

In an embodiment, a composition comprising the vector of an embodiment of the invention comprises a pharmaceutically acceptable buffer sufficient to adjust and maintain the pH of the compositions of an embodiment in the range of about 4.0 to about 8.0, preferably about 5.5 to about 7.0. Suitable buffers may include citrate, phosphate and glycine.

The vectors, alone or in combination with other suitable components, can be made into aerosol formulations to be administered via inhalation. Aerosol formulations can be placed into pressurized acceptable propellants, such as dichlorodifluoromethane, propane, nitrogen, and the like. Aerosol formulations can be delivered into the nasal passage or into the mouth.

Compositions suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain anti-oxidants, buffers, bacteriostats, and solutes that render the formulation isotonic with the blood of the intended recipient, and general aqueous and non-aqueous sterile suspensions that can include suspending agents, solubilizers, thickening agents, stabilizers, and preservatives. The compositions can be presented in unit-dose or multi-dose sealed containers, such as ampoules and vials.

Solutions and suspensions for injection may be prepared from sterile powders, granules, and tablets. Compositions suitable for oral administration can consist of (a) liquid solutions, such as an effective amount of the polysaccharide capsule suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the vector in a flavor, usually sucrose and acacia or tragacanth, as well as pastilles comprising the vector in an inert base, such as gelatin and glycerin or sucrose and acacia emulsions, gels, and the like containing, in addition to the vectors, carriers known in the art. The vector compositions can be encapsulated, e.g., in liposomes, or in a composition that provides for slow release of the vectors.

Vector Administration

The vectors in accordance with embodiments of the invention may be delivered by administration to an individual, typically by systemic administration (e.g., intranasal, intravenous, intraperitoneal, intramuscular, intradermal, subcutaneous, subdermal, transdermal, intracranial, mucosal, anal, vaginal, oral, buccal route or they can be inhaled) or they can be administered by topical application. In an embodiment, the route of administration is intranasal (e.g., nasal sprays or drops). In an embodiment, the route of administration is intramuscular. In other embodiments, the route of administration is subcutaneous. In yet other embodiments, the route of administration is mucosal. In certain embodiments, the route of administration is transdermal or intradermal.

Methods for Eliciting an Immune Response

An embodiment of the invention provides methods for eliciting an immune response to at least one human pathogen comprising administering a non-human Mononegavirales vector of an embodiment of the invention, or a composition comprising the non-human Mononegavirales vector of an embodiment of the invention, to a human.

An embodiment of the invention provides methods for eliciting an immune response to at least one human pathogen comprising administering a non-human Mononegavirales vector of an embodiment of the invention, or a composition comprising the non-human Mononegavirales vector of an embodiment of the invention, to a human, wherein at the time of administration, the human does not suffer from a Pneumoviridae virus infection. In such a case, the vector of an embodiment of the invention, or a composition comprising the vector of an embodiment of the invention, is administered to a human to induce an immune response that can help protect against the establishment of a human Pneumoviridae virus, for example by protecting against infection, the first and necessary step in disease. Thus, in some aspects, the method inhibits infection by a human Pneumoviridae in an uninfected human. In another aspect, the method may reduce the duration of infection in a human who is already infected.

In certain embodiments, the vectors or compositions containing vectors of the invention confer protective immunity, allowing a vaccinated individual to exhibit delayed onset of symptoms or sequelae, or reduced severity of symptoms or sequelae, as the result of his or her exposure to the vector. In particular embodiments, individuals who have been vaccinated may display no symptoms or sequelae upon contact with a human Pneumoviridae, do not become infected by a human Pneumoviridae, or both. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. Cellular immunity can be achieved through cytotoxic T lymphocytes or through delayed-type hypersensitivity that involves dendritic cells, macrophages and T lymphocytes, as well as other mechanisms involving T cells without a requirement for antibodies. In particular, cellular immunity may be mediated by $T_{H1}$ or $T_{H17}$ cells.

Doses

The dose of a vector of an embodiment of the invention, or composition comprising a vector of an embodiment of the invention, is an effective amount, which induces a prophylactic response, as described above, in either a single dose or over multiple doses. Preferably, the dose is selected to minimize adverse side effects. Such an amount will vary depending upon which specific vector employed. In some embodiments, a dose comprises about $10^{8.0}$ infectious units (PFUs) of vector particles. In some embodiments, a dose of the composition comprises about $10^{7.0}$ infectious units (PFUs) of vector particles. In some embodiments, a single dose of the composition comprises about $10^{60}$ infectious units of vector particles. In some embodiments, a single dose of the composition comprises about $10^{5.0}$ (PFUs) infectious units of vector particles. In some embodiments, a single dose of the composition comprises about $10^{4.0}$ (PFUs) infectious units of vector particles. In some embodiments, a single dose of the composition comprises about $10^{3.0}$ (PFUs) infectious units of vector particles. In some embodiments, a single dose of the composition comprises about 102.0 (PFUs) infectious units of vector particles. In some embodiments, a single dose of the composition comprises about 10, or even fewer, of infectious units (PFUs) of vector particles.

In some embodiments, a dose comprises about $10^{8.0}$ infectious units (50%-tissue-culture-infectious units, $TCID_{50}$) of vector particles. In some embodiments, a dose of the composition comprises about $10^{7.0}$ infectious units ($TCID_{50}$) of vector particles. In some embodiments, a single dose of the composition comprises about $10^{6.0}$ infectious units of vector particles. In some embodiments, a single dose of the composition comprises about $10^{5.0}$ ($TCID_{50}$) infectious units of vector particles. In some embodiments, a single dose of the composition comprises about $10^{4.0}$ ($TCID_{50}$) infectious units of vector particles. In some embodiments, a single dose of the composition comprises about $10^{3.0}$ ($TCID_{50}$) infectious units of vector particles. In some embodiments, a single dose of the composition comprises about $10^{2.0}$ ($TCID_{50}$) infectious units of vector particles. In some embodiments, a single dose of the composition comprises about 10, or even fewer, of infectious units ($TCID_{50}$) of vector particles.

The appropriate amount of vector to be delivered will depend on the age, weight, and health (e.g. immunocompromised status) of a subject. When present, typically an adjuvant will be present in amounts from 1-250 μg per dose, for example 50-150 μg, 75-125 μg or 100 μg.

In embodiments, one dose of a vector of an embodiment of the invention, or a composition comprising a vector of an embodiment of the invention, is administered to achieve the results described above. In other embodiments, following an initial vaccination, subjects receive one or more booster vaccinations, for a total of two, three, four or five vaccinations. A booster vaccination may be administered, for example, about 1 month, 2 months, 4 months, 6 months, or 12 months after the initial vaccination, such that one vaccination regimen involves administration at 0, 0.5-2, 4-8, and 12 months. It may be advantageous to administer split doses of vaccines which may be administered by the same or different routes.

In some embodiments, a vector of an embodiment of the invention, or a composition comprising a vector of any embodiment of the invention, will be administered in a dose escalation manner, such that successive administrations of the vector contain a higher concentration of vector than previous administrations. In embodiments, the vector will be administered in a manner such that successive administrations of the vector contain a lower concentration of vector than previous administrations.

In one embodiment, an effective amount is that which provides infection (as defined by the shedding of vaccine virus) in at least 20%, at least 30%, at least 40%, at least 50%, at least 60%, at least 70%, at least 80%, at least 90%, or even 100% of recipients.

In one embodiment, an effective amount is that which provides infection (as defined by a >4-fold increase in serum antibody titer to the vector) in at least 20%, at least 30%, at least 40%, at least 50%, at least 60%, at least 70%, at least 80%, at least 90%, or even 100% of recipients.

In one embodiment, an effective amount is that which provides infection (as defined by a >4-fold increase in serum antibody titer to the expressed foreign antigen) in at least 20%, at least 30%, at least 40%, at least 50%, at least 60%, at least 70%, at least 80%, at least 90%, or even 100% of recipients.

Preparation and Storage of Vector Compositions

The vectors and compositions described herein may be produced using a variety of techniques. An embodiment of the invention provides methods for making live, chimeric non-human Mononegavirales vectors which allow a cell to express at least one protein from at least one human pathogen, comprising inserting a non-native gene that encodes at least one protein from at least one human pathogen in a non-human Mononegavirales vector. In an embodiment, the gene encoding a non-native protein from at least one human pathogen is downstream of a non-human Mononegavirales vector gene start. In an embodiment, the gene encoding a non-native protein from at least one human pathogen is upstream of a vector gene end. As used herein "downstream of a vector gene start" means that the gene encoding a protein from at least one human pathogen is inserted in a position which is downstream of a non-human Mononegavirales vector gene start such that the gene start allows the viral polymerase L protein to transcribe the gene. As used herein "upstream of a non-human Mononegavirales vector gene end" means that the gene encoding a protein from at least one human pathogen is inserted in a position which is upstream of a non-human Mononegavirales vector gene end such that the gene end allows the non-human Mononegavirales vector polymerase protein to stop transcription of the gene at the appropriate position.

In embodiments, methods for manufacturing the vector may comprise mixing one or more proteins or an immunogenic fragment or variant thereof with a carrier and/or an adjuvant.

Kits and Components

An embodiment of the invention provides a kit for eliciting an immune response. The kit can comprise a composition of an embodiment of the invention and at least one container for holding the composition. The kit optionally, but preferably, contains instructions for using the kit to administer the composition of an embodiment of the invention to a human subject. The kit optionally contains components needed to administer the composition (e.g., syringe, needle, nebulizer, atomizer, or dropper).

Embodiments of the present subject matter described herein may be beneficial alone or in combination, with one or more other embodiments. Without limiting the foregoing description, certain non-limiting embodiments of the disclosure numbered (1)-(25) are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below:

(1) A live, chimeric non-human Mononegavirales vector which allows a cell to express at least one protein from at least one human pathogen.

(2) The non-human Mononegavirales vector of embodiment (1), wherein the natural host of the non-human Mononegavirales vector is a non-human animal.

(3) The non-human Mononegavirales vector of embodiment (1) or (2), wherein the natural host of the non-human Mononegavirales vector is from the order Rodentia.

(4) The non-human Mononegavirales vector of any one of embodiments (1)-(3), wherein the non-human Mononegavirales vector is a murine pneumonia virus (MPV).

(5) The non-human Mononegavirales vector of any one of embodiments (1)-(4), wherein the at least one human pathogen is bacteria or a virus.

(6) The non-human Mononegavirales vector of any one of embodiments (1)-(5), wherein the at least one human pathogen is a virus.

(7) The non-human Mononegavirales vector of any one of embodiments (1)-(6), wherein the at least one human pathogen is a human Pneumoviridae virus.

(8) The non-human Mononegavirales vector of any one of embodiments (1)-(7), wherein the at least one human pathogen is an Orthopneumovirus.

(9) The non-human Mononegavirales vector of any one of embodiments (1)-(8), wherein the at least one pathogen is a human respiratory syncytial virus (RSV).

(10) The non-human Mononegavirales vector of any one of embodiments (1)-(9), wherein the at least one protein is RSV F protein.

(11) The non-human Mononegavirales vector of any one of embodiments (1)-(10), wherein the non-human Mononegavirales vector comprises a sequence with at least 90% sequence identity to SEQ ID NO. 56.

(12) The non-human Mononegavirales vector of any one of embodiments (1)-(10), wherein the non-human Mononegavirales vector comprises a sequence with at least 90% sequence identity to SEQ ID NO. 58.

(13) The non-human Mononegavirales vector of any one of embodiments (1)-(9), wherein the at least one protein is RSV G protein.

(14) The non-human Mononegavirales vector of any one of embodiments (1)-(13), comprising a sequence with at least 90% sequence identity to SEQ ID NO: 60.

(15) The non-human Mononegavirales vector of any one of embodiments (1)-(13), comprising a sequence with at least 90% sequence identity to SEQ ID NO: 61.

(16) The non-human Mononegavirales vector of any one of embodiments (1)-(13), comprising a sequence with at least 90% sequence identity to SEQ ID NO: 62.

(17) A composition comprising the non-human Mononegavirales vector of any one of embodiments (1)-(16), and a pharmaceutically acceptable carrier.

(18) The composition of embodiment (17), wherein the composition is formulated for intranasal administration.

(19) A method of eliciting an immune response to at least one human pathogen comprising administering the non-human Mononegavirales vector of any one of embodiments (1)-(16), or the composition of embodiment (17) or (18), to a human.

(20) The method of embodiment (19), wherein at the time of administration, the human does not suffer from a human Pneumoviridae virus infection.

(21) The method of embodiment (19) or (20), wherein at the time of administration, the human does not suffer from a human respiratory syncytial virus (RSV) infection.

(22) The method of any one of embodiments (19)-(21), wherein the non-human Mononegavirales vector is a murine pneumonia virus (MPV).

(23) A method of making a live, chimeric non-human Mononegavirales vector which allows a cell to express at least one protein from at least one human pathogen, comprising:

(a) inserting a non-native gene that encodes at least one protein from at least one human pathogen in a non-human Mononegavirales vector.

(24) A kit for eliciting an immune response, the kit comprising:

(a) the composition of embodiment (17) or (18); and (b) at least one container for holding the composition.

(25) A live, chimeric non-human Mononegavirales vector which allows a cell to express at least one protein from at least one human pathogen.

(26) The non-human Mononegavirales vector of embodiment (25), wherein the natural host of the non-human Mononegavirales vector is a non-human animal.

(27) The non-human Mononegavirales vector of embodiment (25), wherein the natural host of the non-human Mononegavirales vector is from the order Rodentia.

(28) The non-human Mononegavirales vector of embodiment (25), wherein the non-human Mononegavirales vector is a murine pneumonia virus (MPV).

(29) The non-human Mononegavirales vector of embodiment (25), wherein the at least one human pathogen is bacteria or a virus.

(30) The non-human Mononegavirales vector of embodiment (25), wherein the at least one human pathogen is a virus.

(31) The non-human Mononegavirales vector of embodiment (25), wherein the at least one human pathogen is a human Pneumoviridae virus.

(32) The non-human Mononegavirales vector of embodiment (25), wherein the at least one human pathogen is an Orthopneumovirus.

(33) The non-human Mononegavirales vector of embodiment (25), wherein the at least one pathogen is a human respiratory syncytial virus (RSV).

(34) The non-human Mononegavirales vector of embodiment (25), wherein the at least one protein is RSV F protein.

(35) The non-human Mononegavirales vector of embodiment (25), wherein the non-human Mononegavirales vector comprises a sequence with at least 90% sequence identity to SEQ ID NO. 56.

(36) The non-human Mononegavirales vector of embodiment (25), wherein the non-human Mononegavirales vector comprises a sequence with at least 90% sequence identity to SEQ ID NO. 58.

(37) The non-human Mononegavirales vector of embodiment (25), wherein the at least one protein is RSV G protein.

(38) The non-human Mononegavirales vector of embodiment (25), comprising a sequence with at least 90% sequence identity to SEQ ID NO: 60.

(39) The non-human Mononegavirales vector of embodiment (25), comprising a sequence with at least 90% sequence identity to SEQ ID NO: 61.

(40) The non-human Mononegavirales vector of embodiment (25), comprising a sequence with at least 90% sequence identity to SEQ ID NO: 62.

(41) A composition comprising the non-human Mononegavirales vector of embodiment (25), and a pharmaceutically acceptable carrier.

(42) The composition of embodiment (25), wherein the composition is formulated for intranasal administration.

(43) A method of eliciting an immune response to at least one human pathogen comprising administering the non-human Mononegavirales vector of embodiment (25) to a human.

(44) The method of embodiment (43), wherein at the time of administration, the human does not suffer from a human Pneumoviridae virus infection.

(45) The method of embodiment (43), wherein at the time of administration, the human does not suffer from a human respiratory syncytial virus (RSV) infection.

(46) The method of embodiment (43), wherein the non-human Mononegavirales vector is a murine pneumonia virus (MPV).

(47) A method of making a live, chimeric non-human Mononegavirales vector which allows a cell to express at least one protein from at least one human pathogen, comprising:

(a) inserting a non-native gene that encodes at least one protein from at least one human pathogen in a non-human Mononegavirales vector.

(48) A kit for eliciting an immune response, the kit comprising:

(a) the composition of embodiment (42); and (b) at least one container for holding the composition.

The following examples further illustrate the invention but, of course, should not be construed as in any way limiting its scope.

EXAMPLES

Example 1

This example demonstrates how vectors of an embodiment of the invention can be prepared.

The rMPV-RSV-F vectors were constructed using a reverse genetics system as described by Kremp, et al., ("Identification of a novel virulence factor in recombinant pneumonia virus of mice," J. Virol., (81): 9490-9501 (2007) (incorporated herein in its entirety by reference). The rMPV vector backbone used for expressing RSV F was derived from MPV (previously called PVM) strain 15 cloned in a pBluescript plasmid vector ("pBS") that contained the two introduced restriction sites (Agel and BstBI) that were absent in the parent strain 15 and also contained a partially modified L ORF. The downstream 67% of the L ORF was codon-pair optimized ("CPO") to contain synonymous changes that increased the content of codon pairs associated with efficient expression in humans while preserving both the overall codon usage and the encoded amino acid sequence. The RSV F ORF from strain A2 was codon optimized for human codon usage (Genscript, Piscataway, NJ) to obtain greater protein expression. RSV F also carried the two previously described HEK amino acid assignments of 66E and 101P that make the encoded F protein amino acid sequence identical to that of an early passage of wt strain A2 and the clinical isolates.

Three MPV vector constructs were designed in which the RSV F insert was placed in the first gene position, upstream of the NS1 gene (rMPV-F1), in the third gene position, between the NS2 and N genes (rMPV-F3), or in the fourth gene position, between the N and P genes (rMPV-F4) (see FIG. 1). The RSV F inserts are positioned so that the RSV F ORF was flanked by MPV gene start (GS) and gene end (GE) transcription signals to enable transcription of RSV F as a separate mRNA. The Kozak consensus sequence GCCGCCACC (SEQ ID NO: 63) was placed upstream of the RSV F AUG start codon to provide efficient context for translation initiation as described. The RSV F inserts were synthesized commercially (Genscript) as long genome segments designed for insertion into the rMPV antigenomic plasmid using the XmaI restriction site in the plasmid (pBS) sequence upstream of the leader region and the downstream KpnI site (rMPV-F1 and rMPV-F3) or the KpnI and BmtI sites (rMPV-F4) as indicated (see FIG. 1). The final construct rMPV-F1 contains 1768 additional nucleotides, placed immediately after nucleotide position 67 (upstream of NS1), rMPV-F3 contains 1775 additional nucleotides, placed immediately after nucleotide position 981 (between NS2 and N), and rMPV-F4 contains 1771 additional nucleotides, placed immediately after nucleotide position 2276 (between N and P) of the MPV genome.

The rMPV vectors were recovered from cDNA (for an exemplary method, see Krempl, et al. supra) in BHK BSR-T7/5 cells that constitutively express the T7 RNA polymerase. The cells were transfected with the MPV antigenome plasmid and support plasmids expressing MPV N, P, M2-1, and L proteins. Twenty-four hours later, the cells were scraped, vortexed, and the cell suspension was co-cultured with a Vero cell monolayer for approximately two weeks to create P1 viral stocks. It was confirmed that the P1 virus stocks did not contain any adventitious mutations introduced during recovery. Specifically, viral RNA was isolated and Sanger sequence analysis of the complete viral genomes was performed using uncloned overlapping RT-PCR fragments. Control RT-PCR reactions lacking reverse transcriptase did not yield an amplified product, confirming that the PCR products were amplified from the viral RNA and not from cDNA used for virus rescue. Titers of virus stocks were determined by plaque assay and immunostaining.

Example 2

This example demonstrates the in vitro stability of vectors of an embodiment of the invention.

Vero, human lung epithelial, and baby hamster kidney cells were used in his study. Vero cells (African green monkey kidney cells, CCL-81, ATCC, Manassas, VA) were maintained in OPTIPRO™ medium supplemented with 4 mM L-glutamine (ThermoFisher Scientific, Waltham, MA) and 10% fetal bovine serum ("FBS") (Hyclone, Logan, UT). Human lung epithelial A549 (CCL-185; ATCC, Manassas, VA) cells were maintained in F-12K Medium (ATCC) supplemented with 4 mM L-glutamine. BHK BSR T7/5 cells are BHK-21 (baby hamster kidney 21) cells that were maintained in Glasgow's MEM medium (ThermoFisher Scientific) supplemented with 3% FBS. Geneticin (ThermoFisher Scientific) was included in the media for every other passage to ensure selection of T7 RNA polymerase expressing cells.

Recombinant (r) wt RSV strain A2 was used as a control. All in vitro tissue culture experiments were done at 37° ° C. unless otherwise noted, rMPV and the rMPV—RSV-F vectors were propagated on Vero cells by infecting at a multiplicity of infection ("MOI") of 0.1. Virus stocks were harvested about two weeks post infection, when cytopathic effects disrupted the monolayer, rMPV titers were determined by plaque assay on Vero cells under a 0.8% methylcellulose overlay as described. Plaques were visualized by immunostaining with rabbit hyperimmune serum raised against sucrose gradient purified MPV followed by a horseradish peroxidase labeled goat anti-rabbit IgG secondary antibody (KPL, Gaithersburg, MD). Bound secondary antibodies were detected by incubation with a peroxidase substrate (KPL). Each sample was tested in duplicate and the average was reported.

In order to evaluate the stability of expression of RSV F protein following in vitro replication, four independent viral recoveries of each rMPV—RSV-F construct were analyzed by a dual staining plaque assay to determine the stability of RSV F expression. The plaque assay was set up as previously described by Brock et al. ("Evaluation of pneumonia virus of mice as a possible human pathogen," J. Virol., 86: 5829-5843 (2012) (incorporated herein in its entirety by reference)) and cells were fixed using 80% methanol at day four post infection. To identify MPV proteins, a rabbit anti-rMPV polyclonal primary antibody described above was used at 1: 5,000 and detected by a goat anti-rabbit 680 LT antibody (Li-Cor; Lincoln, NE). RSV F was probed with a mixture of three RSV F specific mouse monoclonal antibodies (1129, 1243, and 1269) each at 1: 200 followed by a goat anti-mouse 800 CW secondary antibody (Li-Cor). Both secondary antibodies were used at a 1:800 dilution. The plates were scanned on an Odyssey infrared imager (Li-Cor) and the images were analyzed to determine the percentage of PFUs co-expressing RSV F and rMPV antigens. Plaque images were pseudocolored to appear red and green for MPV and RSV F antigens, respectively. On merging the two channels, rMPV plaques co-expressing RSV F would appear yellow while those with loss of RSV F expression would appear red. As seen in FIG. 2, rMPV-empty vectors did not have RSV F expression as the plaques were red. In contrast, the rMPV-F1, rMPV-F3, and rMPV-F4, were yellow when the channels were merged.

FIG. 3 shows the multi-cycle growth kinetics of the rMPV—RSV-F vectors in human A549 lung epithelial cells. FIG. 4 shows the multi-cycle growth kinetics of the rMPV—RSV-F vectors in Vero cells.

Example 3

This example demonstrates the in vivo stability of vectors of an embodiment of the invention.

To evaluate the stability of expression of RSV F protein following in vivo replication, nasopharyngeal swab and tracheal lavage samples from the rhesus study described below were analyzed by plaque assay followed by fixation and dual stain plaque assay as described above.

In order to evaluate multi-cycle replication kinetics, replicate monolayer cultures of Vero cells and A549 cells in T25 flasks were inoculated with each virus at an MOI of 0.1 PFU/cell and incubated at 32° C. The virus inoculum was adsorbed for three hours after which monolayers were washed twice and replenished with fresh medium. On days one through six and days eight and ten for A549, and days one through 6 and day 8 for Vero cells, two cell monolayers per virus and per cell type were scraped into the supernatant, vortexed, clarified by centrifugation, and frozen. Viral titers were determined by plaque assay on Vero cells.

Next, the expression of the RSV F and MPV vector proteins was evaluated. Vero cell monolayers in 12-well plates were infected at an MOI of 10 PFU per cell with the rMPV—RSV-F vectors, empty vector, wt rMPV, wt RSV, or were mock-infected. At 96 hours post infection, images of infected cells were acquired and cell lysates were prepared to examine viral protein expression by Western blotting. Cells were washed twice with 1×PBS and lysed with 200 μL of cell lysis buffer containing 1X NUPAGE™ LDS sample buffer (ThermoFisher Scientific), 1X COMPLETE™ ULTRA protease inhibitor (Roche, Basel, Switzerland), and protease free water. Each lysate was spun through a QIAshredder spin column (Qiagen, Valencia, CA) and flash frozen on dry ice. Ninety μL of each lysate was combined with 10 μL of 10X Reducing Agent (ThermoFisher Scientific), and denatured and reduced at 70° ° C. for 10 min. Twenty-five μL was loaded per lane followed by SDS-PAGE and Western blot, rMPV G, N, and P proteins were detected with hyperimmune sera raised against sucrose-gradient-purified MPV virions. The MPV F protein was detected with a rabbit polyclonal antiserum raised against a recombinant vaccinia virus expressing the MPV F protein. NS1 and NS2 were detected with rabbit hyperimmune serum raised individually against the synthetic peptides TNFDRSDLET (SEQ ID NO: 64) and SDSEESGDEA (SEQ ID NO: 65) derived from the corresponding proteins, respectively. RSV F was probed with monoclonal antibodies as described by Liang et al. ("Chimeric bovine/human parainfluenza virus type 3 expressing respiratory syncytial virus (RSV) F protein: effect of insert position on expression, replication, immunogenicity, stability, and protection against RSV infection," J. Virol. (88): 4237-4250 (2014) (incorporated herein in its entirety by reference)). Tubulin was detected as a loading control using mouse monoclonal anti-tubulin antibody (ThermoFisher Scientific, catalog number A-11126). Primary antibodies were detected with the corresponding species specific secondary antibodies conjugated with an infrared dye (Li-Cor). Membranes were scanned on an Odyssey infrared imaging system. Band signal values were obtained and background corrected using IMAGESTUDIO™ Lite, version 5.2.5 (Li-Cor).

As seen in FIG. 5, the wt RSV, rMPV-F1, rMPV-F3, and rMPV-F4 infected cells show clear signs of viral infection. The mock infected and rMPV-empty infected cells do not show any signs of infection.

FIG. 6 shows the Western blot, specifically, it can be seen that rMPV-F1, rMPV-F3, and rMPV-F4 (lanes 1, 2, and 3) all contained RSV F protein (while the rMPV-empty [lane 4] and wt MPV [lane 5] did not). FIG. 7 depicts the level of RSV F protein expression in infected cells. As seen in FIG. 7, rMPV-F1, rMPV-F3, rMPV-F4, and wt rRSV all expressed high levels of RSV F protein. FIG. 8 depicts the level of rMPV G, N, P, F, NS1, and NS2 expression in infected cells. As seen in FIG. 8, the infected cells expressed each tested protein, some of which, were downstream of the F protein insertion. These results indicate a stable insertion.

Example 4

This example demonstrates that vectors of an embodiment of the invention are effective at attenuating MPV in rhesus macaques.

The NIH National Institute of Allergy and Infectious Diseases Animal Care and Use Committee approved the nonhuman primate experiment described herein, which was performed in accordance with recommendations from the Guide for the Care and Use of Laboratory Animals, The National Academies Press, Washington, D.C. (2011). Eight young adult rhesus macaques (*Macaca* mulatta) were tested to confirm that they were seronegative for both RSV and MPV by separate $PRNT_{60}$ assays. Two groups of four macaques each were inoculated through the combined intranasal and intratracheal routes with 1.0 mL of inoculum per site containing 106 PFUs of rMPV-F1 or rMPV-F3 diluted in L-15 medium (ThermoFisher Scientific). In a separate study, four rhesus macaques of the same cohort as those used for rMPV vectors were inoculated with 7.0 $log_{10}$ PFU per site of recombinant wt RSV strain A2. All four animals were pre-screened to be seronegative for RSV. Clinical observations were made daily. Nasopharyngeal ("NP") swabs were collected on days 0-10, 12, 14, 21, and 28. Tracheal lavage ("TL") samples were collected post-infection on days 2, 4, 6, 8, 10, 12, 14, 21, and 28. The NP and TL samples were analyzed by plaque assay as described above to quantify viral shedding. To assess the immunogenicity, sera were collected on days 0, 14, 21, and 28 days post-immunization and were analyzed for RSV- and MPV-neutralizing antibodies by $PRNT_{60}$.

The PRNT 60 (60% plaque reduction neutralization test) were performed as follows. Serum samples were analyzed for RSV- and MPV-neutralizing antibody titers by performing $PRNT_{60}$ assays on Vero cells using RSV-GFP and MPV-GFP, respectively. Sera from all twelve animals immunized with rMPV-F1, -F3, or wt RSV were analyzed side-by-side for RSV neutralizing antibody levels in the same experiment. Prior to use, serum samples were incubated for 30 minutes at 56° ° C. to inactivate the serum complement. Serial dilutions of serum were then mixed with an equal volume of diluted RSV-GFP or MPV-GFP and incubated at 37° C. for 30 min. The RSV neutralization assay was performed in the presence of 10% guinea pig complement (Lonza, Walkersville, MD). Complement was excluded from the MPV neutralization assay as it inactivates the virus. At day 6 post-infection, images of the RSV-GFP and MPV-GFP plaques were obtained by scanning on a Typhoon imager (GE Healthcare, Piscataway, NJ) and $PRNT_{60}$ was calculated. Each sample was tested in duplicate and the average values were reported as $Log_2$ $PRNT_{60}$.

TABLE 2

Viral titers of nasopharyngeal swab samples from the upper respiratory tract of rhesus macaques inoculated with the indicated rMPV-RSV F vectors or with wt RSV

| | | Virus titer ($log_{10}$ PFU/mL) on indicated day | | | | | | | | | | Peak virus | Days of |
|---|---|---|---|---|---|---|---|---|---|---|---|---|---|
| Group | Animal ID | 1 | 2 | 3 | 4 | 5 | 6 | 7 | 8 | 9 | 10 | titer | shedding |
| rMPV-F1 | A | 2.0 | — | 2.2 | 1.6 | 2.6 | — | — | — | — | — | 2.6 | 5 |
| | B | — | — | 1.8 | 1.5 | 1.5 | 1.0 | 1.7 | — | 1.9 | — | 1.9 | 7 |
| | C | — | — | 1.7 | 1.7 | 1.5 | 1.0 | 1.6 | — | 1.2 | — | 1.7 | 7 |
| | D | — | — | — | — | — | — | — | — | — | — | — | 0 |
| | Mean ± SD: | | | | | | | | | | | 1.6 ± 1.1 | 4.8 ± 3.3 |
| rMPV-F3 | E | — | — | — | — | 1.4 | — | — | — | — | — | 1.4 | 1 |
| | F | 1.7 | 1.6 | 2.0 | 1.6 | 1.7 | 1.7 | — | 1.6 | 1.3 | — | 2.0 | 9 |
| | G | — | — | — | — | — | — | — | — | — | — | — | 0 |
| | H | 2.3 | 2.0 | 1.7 | 2.0 | 1.6 | 1.4 | — | 1.3 | 1.7 | — | 2.3 | 9 |
| | Mean ± SD: | | | | | | | | | | | 1.4 ± 1.0 | 4.8 ± 4.9 |
| wt RSV | I | 0.7 | — | 0.7 | 1.8 | 0.7 | 1.0 | 1.0 | 0.7 | — | — | 1.8 | 8 |
| | J | — | 2.4 | 3.6 | 3.3 | 1.9 | 2.2 | 2.2 | — | — | — | 3.6 | 6 |
| | K | — | 2.6 | 2.7 | 3.4 | 1.6 | 1.2 | 1.2 | — | — | — | 3.4 | 6 |
| | L | — | — | 0.7 | 1.9 | 2.0 | 1.0 | 2.2 | 1.3 | — | — | 2.2 | 6 |
| | Mean ± SD: | | | | | | | | | | | 2.8 ± 0.9 | 6.5 ± 1.0 |

Time points after day ten had no detectable virus and are not shown. The lower limit of detection was 0.7 $log_{10}$ PFU/mL. Samples without any detectable virus are represented as "---". "Days of shedding" indicates the time period spanning the first day to the last day on which virus was detected, including negative days (if any) in between.

TABLE 3

Viral titers of tracheal lavage samples from the lower respiratory tract of rhesus macaques inoculated with the indicated rMPV-RSV F vectors or with wt RSV

| | | Virus titer ($log_{10}$ PFU/mL) on indicated day | | | | Peak virus | # of days |
|---|---|---|---|---|---|---|---|
| Group | Animal ID | 2 | 4 | 6 | 8 | titer | shedding |
| rMPV-F1 | A | 1.7 | — | 1.7 | — | 1.7 | 5 |
| | B | 1.0 | 1.5 | — | — | 1.5 | 3 |
| | C | 1.0 | — | 2.0 | — | 2.0 | 5 |
| | D | 2.1 | — | — | — | 2.1 | 1 |
| | Mean ± SD: | | | | | 1.8 ± 0.3 | 3.5 ± 1.9 |
| rMPV-F3 | E | 1.5 | — | 2.0 | — | 2.0 | 5 |
| | F | 2.3 | — | — | — | 2.3 | 1 |
| | G | — | — | — | — | — | 0 |
| | H | 2.6 | — | — | — | 2.6 | 1 |
| | Mean ± SD: | | | | | 1.7 ± 1.2 | 1.8 ± 2.2 |
| wt RSV | I | 3.2 | 2.5 | — | — | 3.2 | 3 |
| | J | 2.2 | 2.1 | 2.7 | — | 2.7 | 5 |
| | K | — | — | — | — | — | 0 |
| | L | 4.1 | 3.0 | 2.6 | 1.5 | 4.1 | 7 |
| | Mean ± SD: | | | | | 2.5 ± 1.8 | 4.0 ± 3.6 |

Time points after day 8 had no detectable virus and are not shown. Samples without any detectable virus are represented as "---". The lower limit of detection was 0.7 $log_{10}$ PFU/mL. "# of days shedding" indicates the time period spanning the first day to the last day on which virus was detected, including negative days (if any) in between.

TABLE 4

Percentage of plaque forming units (PFU) expressing RSV F in samples inoculated collected from the upper and lower respiratory tract of rhesus macaques with rMPV vectors Percent PFU expressing RSV F

| Virus | Monkey ID | Day 1 | Day 2 | Day 3 | Day 4 | Day 5 | Day 6 | Day 7 | Day 8 | Day 9 |
|---|---|---|---|---|---|---|---|---|---|---|
| Nasopharyngeal swabs | | | | | | | | | | |
| rMPV-F1 | A | — | — | 100 | 50 | 80 | — | — | — | — |
| | B | — | — | 100 | 67 | 100 | 100 | 100 | — | 80 |
| | C | — | — | 100 | 100 | 100 | 100 | 100 | — | 50 |
| | D | — | — | — | — | — | — | — | — | — |
| rMPV-F3 | E | — | — | — | — | 100 | — | — | — | — |
| | F | 100 | 83 | 100 | 100 | 100 | 100 | — | 67 | 80 |
| | G | — | — | — | — | — | — | — | — | — |
| | H | 75 | 100 | 100 | 100 | 100 | — | — | 100 | — |
| Tracheal lavage | | | | | | | | | | |
| rMPV-F1 | A | nc | — | nc | — | nc | 75 | nc | — | nc |
| | B | nc | — | nc | 100 | nc | — | nc | — | nc |
| | C | nc | 100 | nc | — | nc | — | nc | — | nc |
| | D | nc | 100 | nc | — | nc | — | nc | — | nc |
| rMPV-F3 | E | nc | 100 | nc | — | nc | 100 | nc | — | nc |
| | F | nc | 100 | nc | — | nc | — | nc | — | nc |
| | G | nc | — | nc | — | nc | — | nc | — | nc |
| | H | nc | 94 | nc | — | nc | — | nc | — | nc |

The nasopharyngeal swabs and tracheal lavage samples collected on the indicated days after intranasal immunization were analyzed by fluorescent dual staining plaque assay on Vero cells to determine the percentage of viral PFU co-expressing RSV F and MPV antigens during in vivo virus replication. These percent values were determined from approximately 100 plaques per sample. Samples without any detectable virus are represented as "---". Days in which samples were not collected are designated by "nc."

TABLE 5

RSV 60% plaque reduction neutralization titers ($PRNT_{60}$) of serum samples from rhesus macaques immunized with the rMPV-RSV-F vectors or with wt RSV RSV PRNT ($log_2$ 60% titer)

| Group | ID | day 0 | day 14 | day 21 | day 28 |
|---|---|---|---|---|---|
| rMPV-F1 | A | <3.3 | 8.2 | 9.8 | 9.6 |
| | B | <3.3 | 5.4 | 6.3 | 7.3 |
| | C | <3.3 | 7.1 | 8.4 | 8.6 |
| | D | <3.3 | 6.9 | 7.9 | 7.4 |
| Mean + SD: | | <3.3 ± 0.0 | 6.9 ± 1.2 | 8.1 ± 1.4 | 8.2 ± 1.1 |
| rMPV-F3 | E | <3.3 | 5.5 | 6.2 | 7.0 |
| | F | <3.3 | 5.0 | 8.3 | 8.2 |
| | G | <3.3 | 7.6 | 8.0 | 7.8 |
| | H | <3.3 | 7.4 | 8.7 | 8.3 |
| Mean ± SD: | | <3.3 ± 0.0 | 6.4 ± 1.3 | 7.8 ± 1.1 | 7.8 ± 0.6 |
| wt RSV | I | <3.3 | 7.8 | 7.9 | 7.4 |
| | J | <3.3 | 7.8 | 8.7 | 8.3 |
| | K | <3.3 | 7.7 | 8.9 | 9.1 |
| | L | <3.3 | 8.1 | 8.7 | 8.8 |
| Mean ± SD: | | <3.3 ± 0.0 | 7.9 ± 0.2 | 8.6 ± 0.4 | 8.4 ± 0.7 |

The lower limit of detection of the RSV $PRNT_{60}$ assay was 3.3 (log 60% titer). An RSV serum sample with a $log_2$ $PRNT_{60}$ value ≥5.3 was considered positive.

TABLE 6

MPV 60% plaque reduction neutralization titers ($PRNT_{60}$) of serum samples from rhesus macaques immunized with the rMPV-RSV F vectors MPV PRNT ($log_2$ 60% titer)

| Group | ID | day 0 | day 14 | day 21 | day 28 |
|---|---|---|---|---|---|
| rMPV-F1 | A | <3.3 | 13.7 | 13.8 | 13.7 |
| | B | <3.3 | 10.9 | 11.0 | 10.4 |
| | C | <3.3 | 10.7 | 11.7 | 12.5 |
| | D | <3.3 | 8.8 | 8.8 | 8.6 |
| Mean ± SD: | | <3.3 ± 0.0 | 11.0 ± 2.0 | 11.3 ± 2.1 | 11.3 ± 2.3 |
| rMPV-F3 | E | <3.3 | 11.6 | 11.2 | 11.5 |
| | F | <3.3 | 10.4 | 10.2 | 11.8 |
| | G | <3.3 | 9.5 | 9.6 | 10.5 |
| | H | <3.3 | 9.5 | 11.5 | 11.7 |
| Mean ± SD: | | <3.3 ± 0.0 | 10.3 ± 1.0 | 10.6 ± 0.9 | 11.4 ± 0.6 |

The lower limit of detection of the ($PRNT_{60}$) assay was 3.3 ($log_2$ 60% titer). An MPV serum sample with a $log_2$ $PRNT_{60}$ value ≥5.3 was considered positive.

As seen in Tables 2-6, both viruses (rMPV-F1 and rMPV-F3) replicated at low levels in the upper and lower respiratory tract, maintained stable RSV F expression, and induced RSV-neutralizing serum antibodies at high levels similar to those induced by wt RSV replicating to a 5- to 25-fold higher titer. This study demonstrates that rMPV provides a highly attenuated yet immunogenic vector for the expression of RSV F protein, with potential application in RSV-naïve and RSV-experienced populations.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims)

are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A live, chimeric murine pneumonia virus (MPV) vector which allows a cell to express at least one protein from at least one human pathogen, wherein the at least one human pathogen is a virus.

2. The MPV vector of claim 1, wherein the at least one human pathogen is a human Pneumoviridae virus.

3. The MPV vector of claim 1, wherein the at least one human pathogen is an Orthopneumovirus.

4. The MPV vector of claim 1, wherein the at least one pathogen is a human respiratory syncytial virus (RSV).

5. The MPV vector of claim 1, wherein the at least one protein is RSV F protein.

6. The MPV vector of claim 1, wherein the at least one protein is RSV G protein.

7. The MPV vector of claim 1, comprising a sequence with at least 90% sequence identity to SEQ ID NO: 60.

8. The MPV vector of claim 1, comprising a sequence with at least 90% sequence identity to SEQ ID NO: 61.

9. The MPV vector of claim 1, comprising a sequence with at least 90% sequence identity to SEQ ID NO: 62.

10. A composition comprising the MPV vector of claim 1, and a pharmaceutically acceptable carrier.

11. The composition of claim 10, wherein the composition is formulated for intranasal administration.

12. A method of making a live, chimeric murine pneumonia virus (MPV) vector which allows a cell to express at least one protein from at least one human pathogen, comprising inserting a non-native gene that encodes at least one protein from at least one human pathogen in a MPV vector, wherein the at least one human pathogen is a virus.

13. A kit for eliciting an immune response, the kit comprising:

(a) the composition of claim 10; and (b) at least one container for holding the composition.

14. A method of eliciting an immune response to at least one human pathogen comprising administering the MPV vector of claim 1 to a human.

15. The MPV vector of claim 1, wherein the MPV vector allows a cell to produce RSV F protein comprising an amino acid sequence with at least 85% identity to SEQ ID NO: 57.

16. The MPV vector of claim 1, wherein the MPV vector allows a cell to produce RSV F protein comprising an amino acid sequence with at least 85% identity to SEQ ID NO: 59.

17. The MPV vector of claim 1, wherein the at least one human pathogen is a human Coronaviridae virus.

18. The MPV vector of claim 1, wherein the at least one pathogen is a Severe Acute Respiratory Synydrome (SARS), Coronavirus, or Middle East Respiratory Syndrome (MERS) Coronavirus.

19. The MPV vector of claim 1, wherein the at least one protein is a Spike protein of family Coronaviridae.

* * * * *